United States Patent
Kawakami et al.

(10) Patent No.: US 7,732,064 B2
(45) Date of Patent: Jun. 8, 2010

(54) ANTHRACENE DERIVATIVE, AND LIGHT-EMITTING ELEMENT, LIGHT-EMITTING DEVICE, AND ELECTRONIC APPLIANCE USING THE SAME

(75) Inventors: Sachiko Kawakami, Kanagawa (JP); Harue Nakashima, Kanagawa (JP); Kumi Kojima, Tokyo (JP); Ryoji Nomura, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 523 days.

(21) Appl. No.: 11/794,052

(22) PCT Filed: Dec. 22, 2005

(86) PCT No.: PCT/JP2005/024166

§ 371 (c)(1),
(2), (4) Date: Jun. 21, 2007

(87) PCT Pub. No.: WO2006/070897

PCT Pub. Date: Jul. 6, 2006

(65) Prior Publication Data

US 2008/0114178 A1    May 15, 2008

(30) Foreign Application Priority Data

Dec. 28, 2004  (JP) .............................. 2004-381201
Jul. 14, 2005  (JP) .............................. 2005-205308

(51) Int. Cl.
*H01L 51/50* (2006.01)
(52) U.S. Cl. ........................................ 428/690; 544/35
(58) Field of Classification Search ........................ None
See application file for complete search history.

(56) References Cited

U.S. PATENT DOCUMENTS

| | | | |
|---|---|---|---|
| 5,811,834 | A | 9/1998 | Tamano et al. |
| 6,743,948 | B1 | 6/2004 | Hosokawa et al. |
| 6,951,693 | B2 | 10/2005 | Hosokawa et al. |
| 2005/0038296 | A1 | 2/2005 | Hosokawa et al. |
| 2005/0260450 | A1* | 11/2005 | Yamagata et al. ............ 428/690 |
| 2006/0068221 | A1 | 3/2006 | Saitoh et al. |
| 2006/0189828 | A1 | 8/2006 | Hosokawa et al. |

FOREIGN PATENT DOCUMENTS

| | | |
|---|---|---|
| EP | 1 061 112 A1 | 12/2000 |
| EP | 0 786 926 B1 | 8/2001 |
| EP | 1 666 561 A1 | 6/2006 |
| EP | 1 775 335 A2 | 4/2007 |
| JP | 9-268283 | 10/1997 |
| JP | 2001-131541 | 5/2001 |
| JP | 2003-31371 | 1/2003 |
| JP | 2004-87363 | 3/2004 |
| WO | WO 2004/020548 A1 | 3/2004 |

OTHER PUBLICATIONS

International search Report re application No. PCT/JP2005/024166, dated Feb. 21, 2006.
Written Opinion re application No. PCT/JP2005/024166, dated Feb. 21, 2006.

* cited by examiner

*Primary Examiner*—D. Lawrence Tarazano
*Assistant Examiner*—Gregory Clark
(74) *Attorney, Agent, or Firm*—Husch Blackwell Sanders LLP

(57) ABSTRACT

It is an object of the present invention to provide a light-emitting substance which is resistant to repetition of an oxidation reaction. It is another object of the invention to provide a light-emitting element which is resistant to repetition of a reduction reaction. An aspect of the present invention is an anthracene derivative represented by a general formula (1). In the general formula (1), R1 represents hydrogen or an alkyl group having 1 to 4 carbon atoms; R2 represents any one of hydrogen, an alkyl group having 1 to 4 carbon atoms, and an aryl group having 6 to 12 carbon atoms, which may have a substituent or no substituent; Ph1 represents a phenyl group, which may have a substituent or no substituent; and X1 represents an arylene group having 6 to 15 carbon atoms.
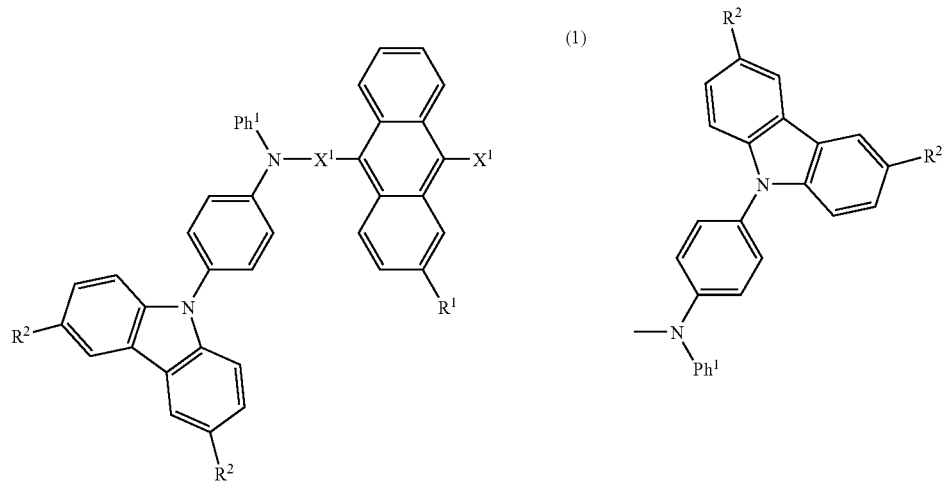
12 Claims, 40 Drawing Sheets

ANTHRACENE DERIVATIVE, AND LIGHT-EMITTING ELEMENT, LIGHT-EMITTING DEVICE, AND ELECTRONIC APPLIANCE USING THE SAME

TECHNICAL FIELD

The present invention relates to an anthracene derivative, and in particular, an anthracene derivative that can be used as a material for manufacturing a light-emitting element.

BACKGROUND ART

In recent years, many of light-emitting elements used for displays and the like have a structure in which a layer containing a light-emitting substance is sandwiched between a pair of electrodes. Such light-emitting elements emit light when excitons which are formed by recombination of electrons injected from one electrodes and holes injected from the other electrodes return to a ground state.

In the field of light-emitting elements, in order to obtain a light-emitting element having high light-emitting efficiency and high chromaticity or a light-emitting element in which optical quenching and the like can be prevented, various researches about substances which become materials for manufacturing such a light-emitting element have been carried out.

For example, Patent Document 1 (Japanese Patent Application Laid-Open No. 2001-131541) discloses a material for an organic EL element having high light-emitting efficiency and long lifetime.

Further, in a light-emitting element, current flows between electrodes by transportation of holes or electrons. In this case, a light-emitting substance which has received holes or electrons or the like, or, a light-emitting substance which has been oxidized or reduced or the like sometimes does not return to a neutral state and is changed into a substance having a different property. When such changes of the property of the light-emitting substance are accumulated, a characteristic of the light-emitting element may also be changed.

Therefore, development has been demanded on a light-emitting substance of which a property is difficult to be changed due to oxidation or reduction.

DISCLOSURE OF INVENTION

It is an object of the present invention to provide a substance which has high resistance to repetition of an oxidation reaction and which can be used as a material for a light-emitting element. Moreover, it is another object of the present invention to provide a light-emitting element and a light-emitting device in each of which deterioration in an operational characteristic of the light-emitting element due to change in a characteristic of a substance caused by repetition of an oxidation reaction is reduced.

An aspect of the present invention is an anthracene derivative represented by a general formula (1).

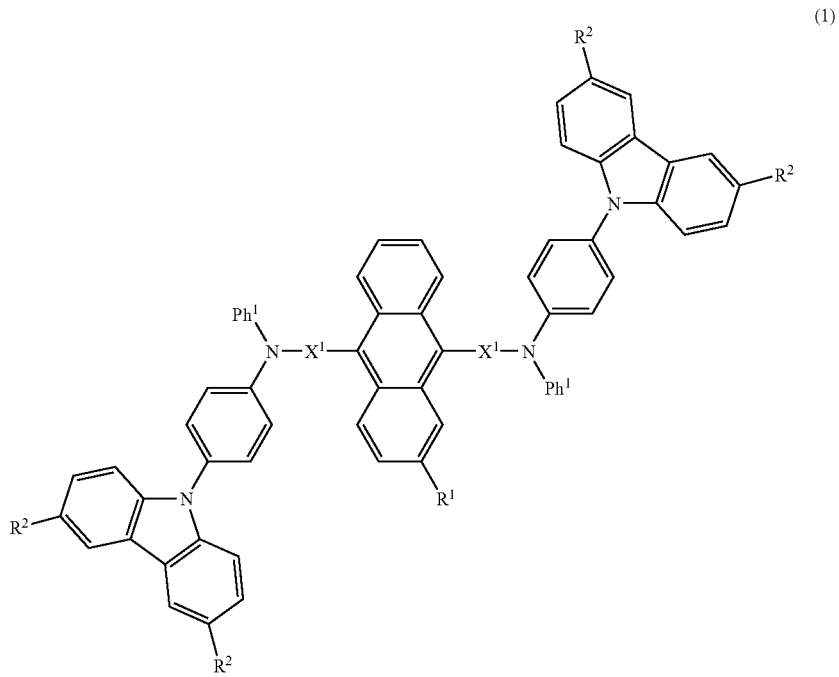

In the general formula (1), $R^1$ represents hydrogen or an alkyl group having 1 to 4 carbon atoms. $R^2$ represents any one of hydrogen, an alkyl group having 1 to 4 carbon atoms, and an aryl group having 6 to 12 carbon atoms. The aryl group may have a substituent or no substituent. $Ph^1$ represents a phenyl group. The phenyl group may have a substituent or no substituent. $X^1$ represents an arylene group having 6 to 15 carbon atoms. The arylene group may have a substituent or no substituent.

Another aspect of the present invention is an anthracene derivative represented by a general formula (2).

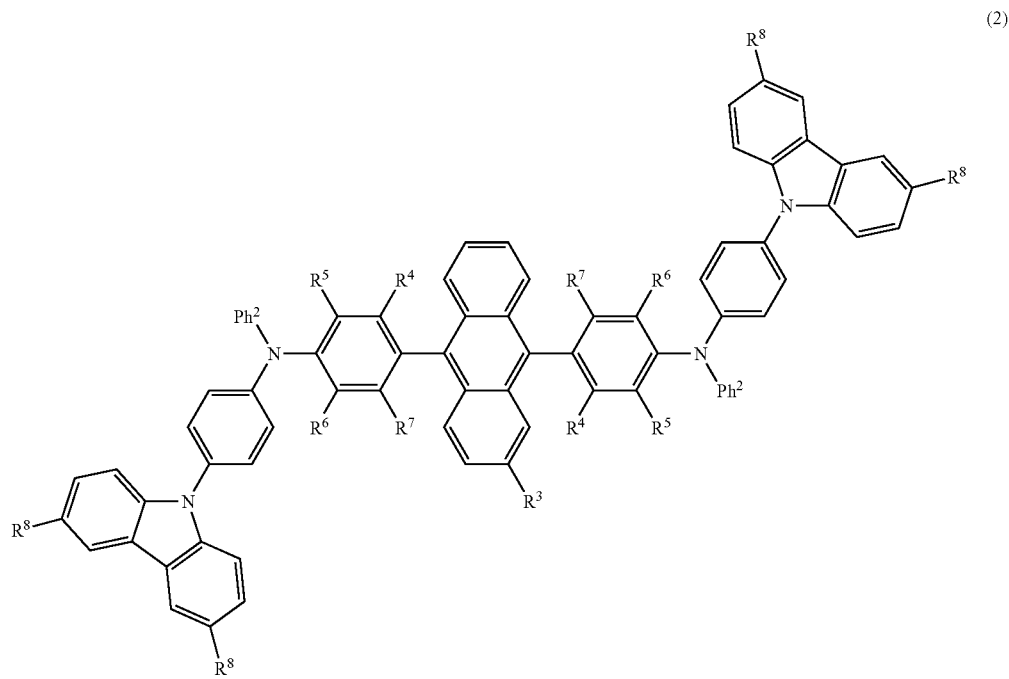

In the general formula (2), $R^3$ represents hydrogen or an alkyl group having 1 to 4 carbon atoms. $R^4$ to $R^7$ independently represent hydrogen, or $R^4$ and $R^5$ represent aromatic rings which are bonded to each other and $R^6$ and $R^7$ respectively represent aromatic rings which are bonded to each other. $R^8$ represents any one of hydrogen, an alkyl group having 1 to 4 carbon atoms, and an aryl group having 6 to 12 carbon atoms. The aryl group may have a substituent or no substituent. $Ph^2$ represents a phenyl group. The phenyl group may have a substituent or no substituent.

Another aspect of the present invention is an anthracene derivative represented by a general formula (3).

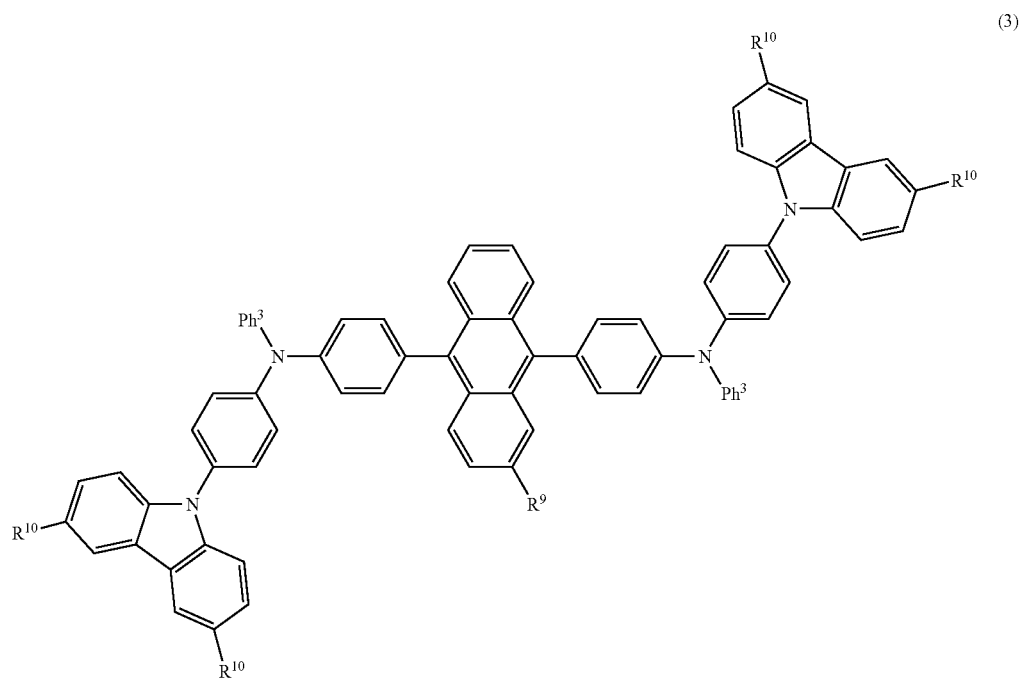

In the general formula (3), $R^9$ represents hydrogen or an alkyl group having 1 to 4 carbon atoms. $R^{10}$ represents any one of hydrogen, an alkyl group having 1 to 4 carbon atoms, and an aryl group having 6 to 12 carbon atoms. The aryl group may have a substituent or no substituent. $Ph^3$ represents a phenyl group. The phenyl group may have a substituent or no substituent.

Another aspect of the present invention is an anthracene derivative represented by a general formula (4).

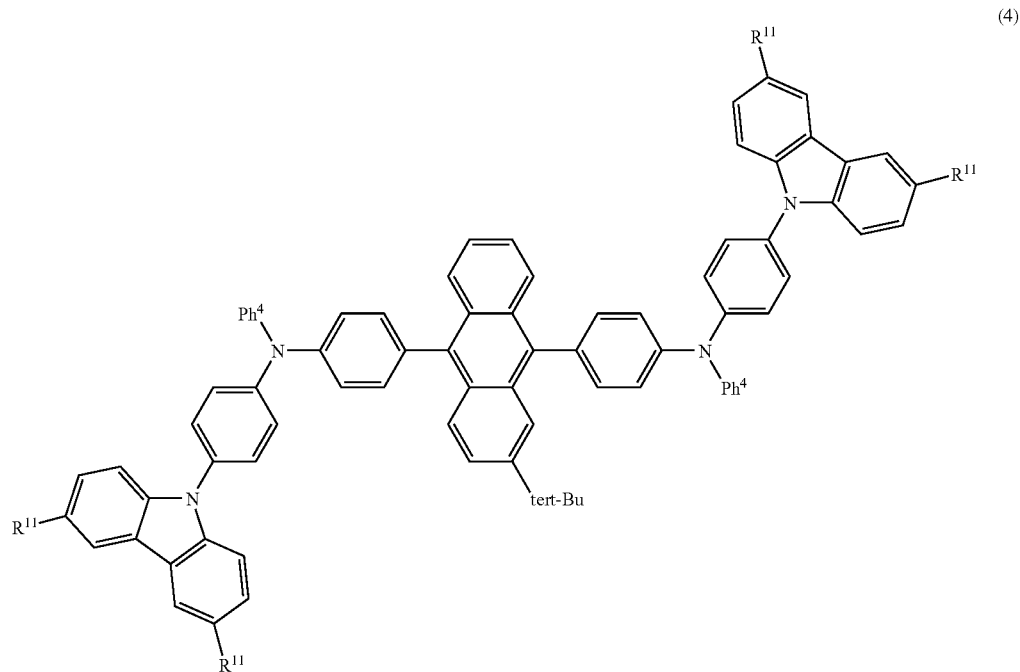

(4)

In the general formula (4), $R^{11}$ represents any one of hydrogen, an alkyl group having 1 to 4 carbon atoms, and an aryl group having 6 to 12 carbon atoms. The aryl group may have a substituent or no substituent. $Ph^4$ represents a phenyl group. The phenyl group may have a substituent or no substituent.

Another aspect of the present invention is an anthracene derivative represented by a general formula (5).

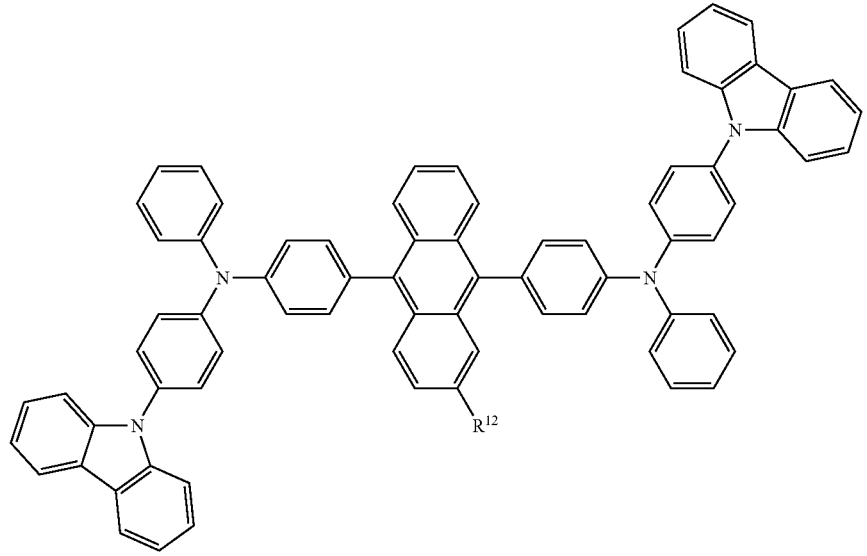

(5)

In the general formula (5), $R^{12}$ represents hydrogen or an alkyl group having 1 to 4 carbon atoms.

Another aspect of the present invention is an anthracene derivative represented by a general formula (6).

In the general formula (7), $R^{13}$ represents any one of hydrogen, an alkyl group having 1 to 4 carbon atoms, and an aryl group having 6 to 12 carbon atoms. The aryl group may have a substituent or no substituent.

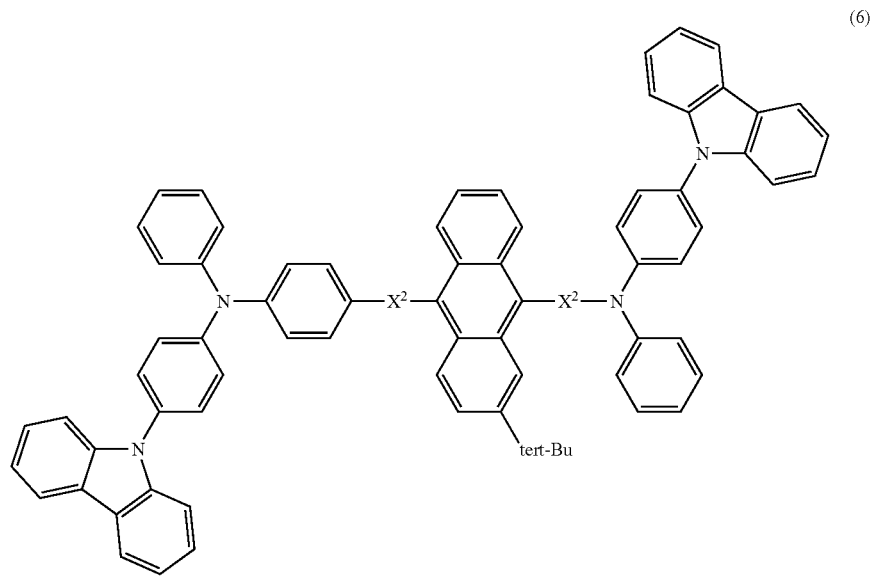

(6)

In the general formula (6), $X^2$ represents an arylene group having 6 to 15 carbon atoms. The arylene group may have a substituent or no substituent.

Another aspect of the present invention is an anthracene derivative represented by a general formula (7).

Another aspect of the present invention is a light-emitting element which has, between electrodes, a layer containing an anthracene derivative represented by any one of the general formulas (1) to (7).

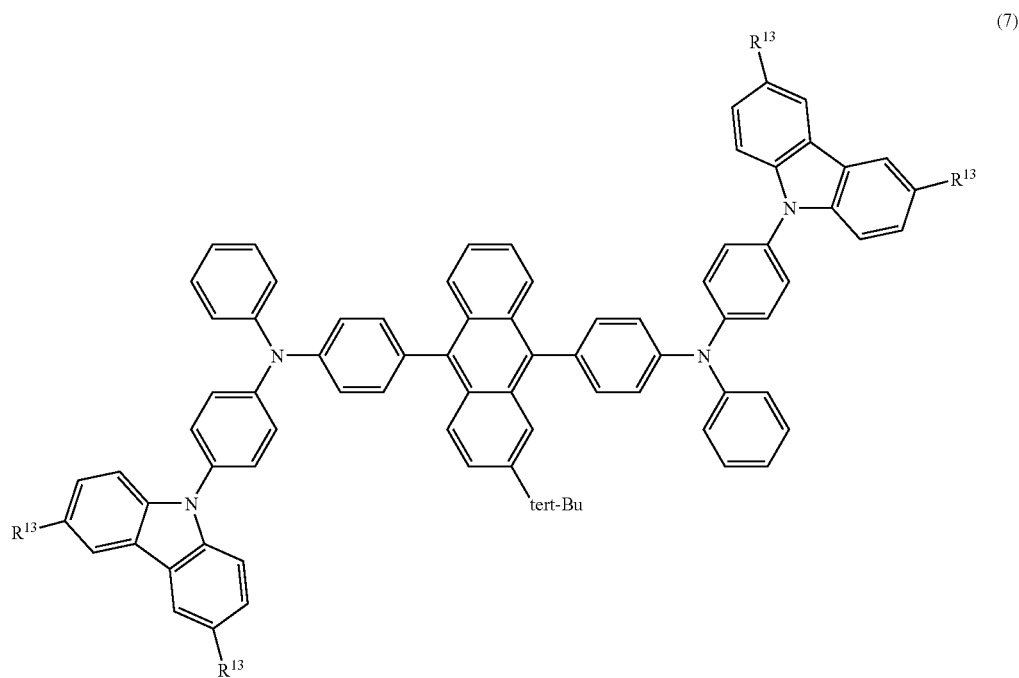

(7)

Another aspect of the present invention is a light-emitting device using a light-emitting element having a layer containing an anthracene derivative represented by any one of the general formulas (1) to (7).

Another aspect of the present invention is a light-emitting device which has, in a pixel portion thereof, a light-emitting element containing an anthracene derivative represented by any one of the general formulas (1) to (7).

Another aspect of the present invention is an electronic appliance in which a light-emitting device which uses a light-emitting element containing an anthracene derivative represented by any one of the general formulas (1) to (7) is mounted in a display portion.

By carrying out the present invention, a substance which is highly resistant to repetition of an oxidation reaction and which can be used as a material for manufacturing a light-emitting element can be obtained. In addition, by carrying out the present invention, it is possible to obtain a substance which is highly resistant to repetition of an oxidation reaction and to repetition of a reduction reaction and which can be used as a material for manufacturing a light-emitting element.

By carrying out the present invention, it is possible to obtain a light-emitting element in which deterioration in an element characteristic caused by repetition of an oxidation reaction of a substance used in a layer provided between electrodes can be reduced. It is also possible to obtain a light-emitting element which can exhibit stable light emission for a long time and has few changes in a characteristic of the light-emitting element caused by a change in a property of a light-emitting substance due to repetition of an oxidation reaction.

BEST MODE FOR CARRYING OUT THE INVENTION

Figure 1:
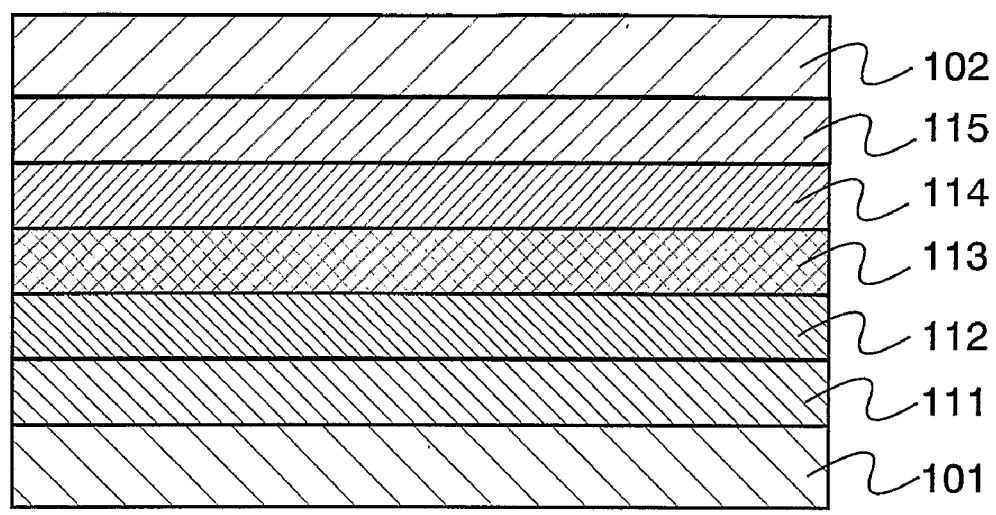
FIG. 1 explains a light-emitting element of the present invention.

Embodiment Modes and Embodiments of the present invention will be hereinafter described. However, it is easily understood by those skilled in the art that the modes and details herein disclosed can be modified in various ways without departing from the purpose and the scope of the invention. Therefore, the present invention should not be interpreted as being limited to the description of Embodiment Modes and Embodiments given below.

Embodiment Mode 1

An embodiment mode of an anthracene derivative of the present invention will be described.

As an anthracene derivative of the present invention, anthracene derivatives represented by structural formulas (1) to (28) can be given.

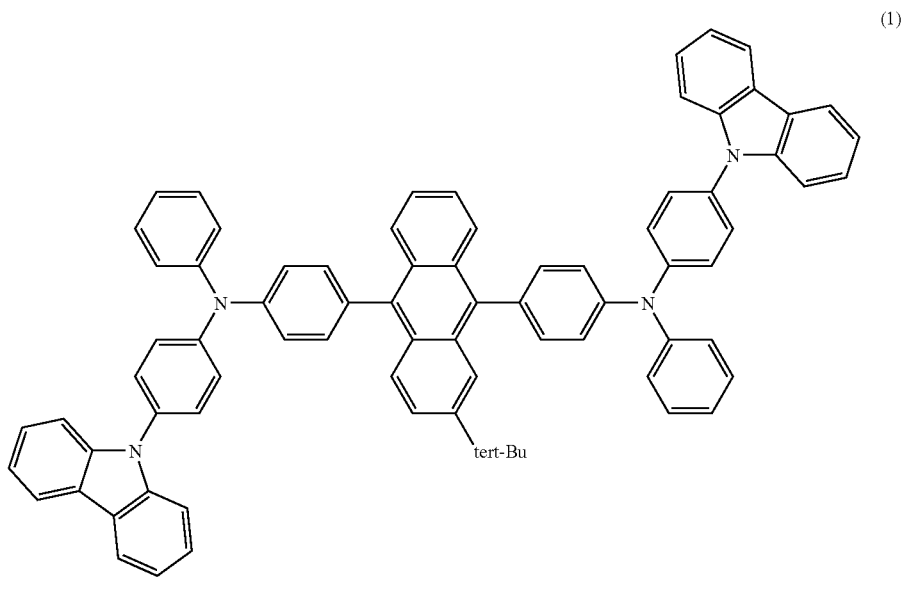

(1)

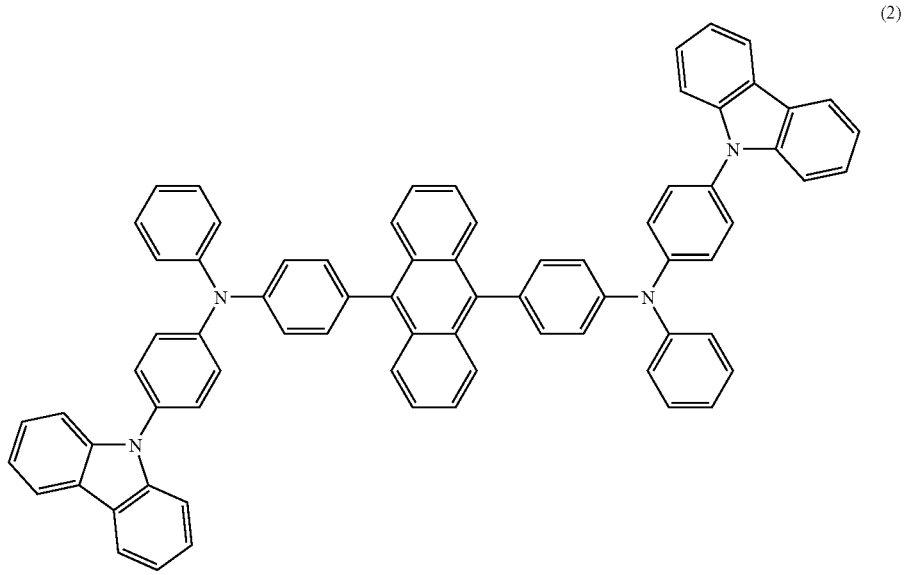

(2)

-continued
(3)
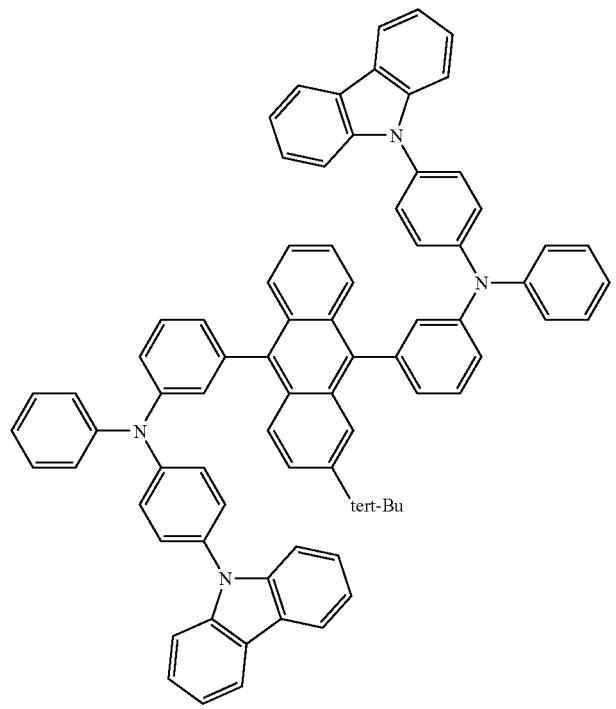
(4)
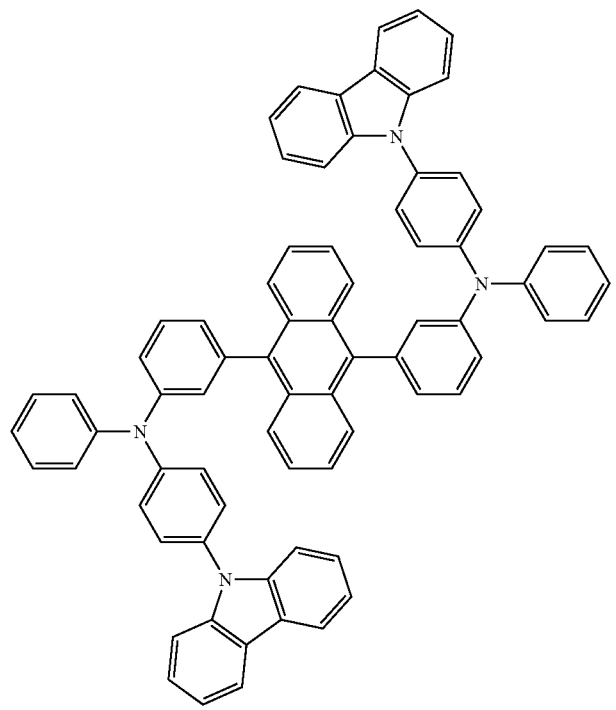

-continued
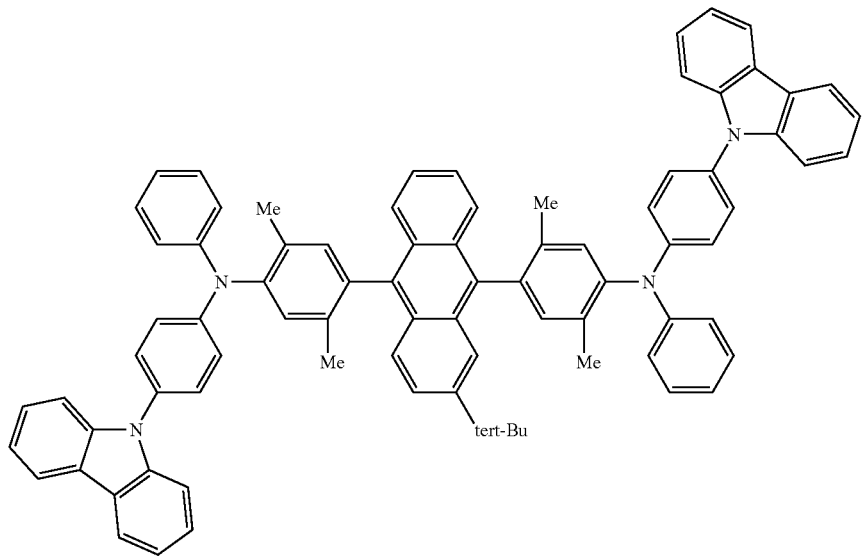
(5)
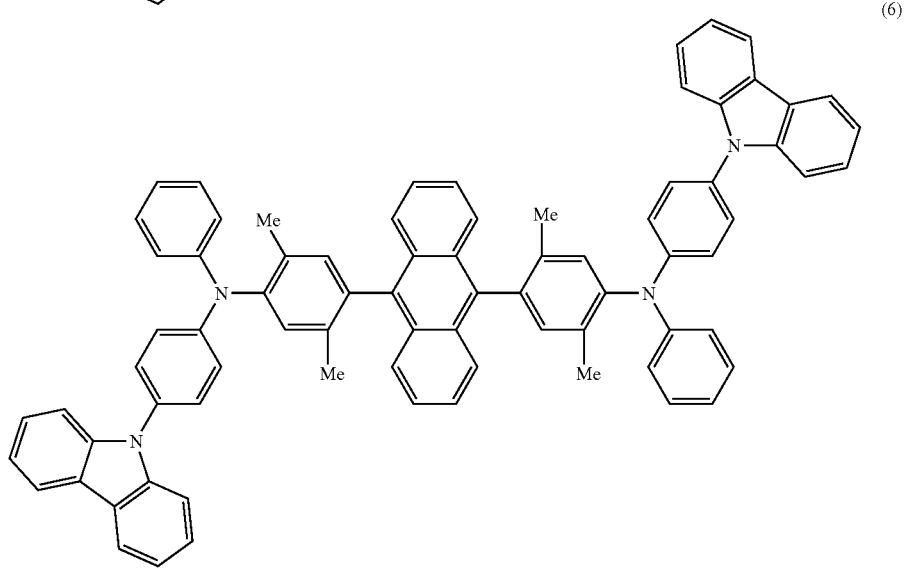
(6)
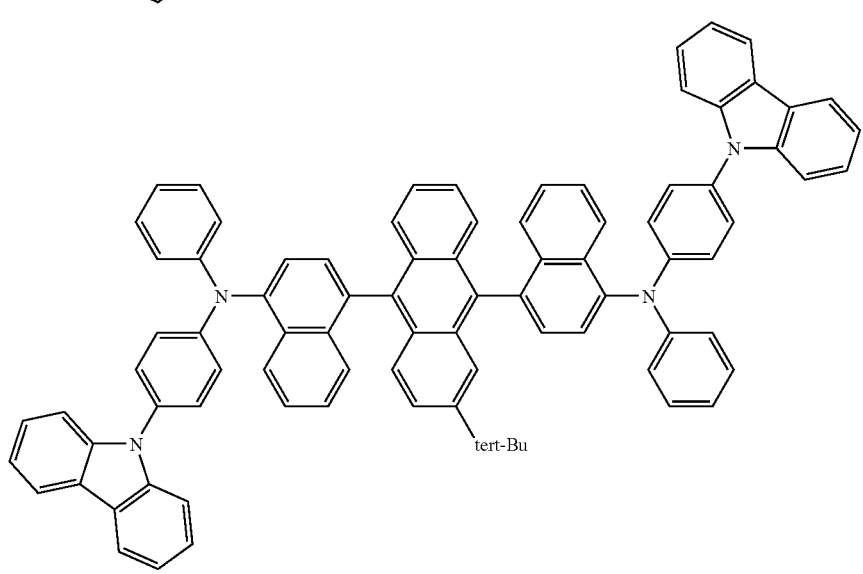
(7)

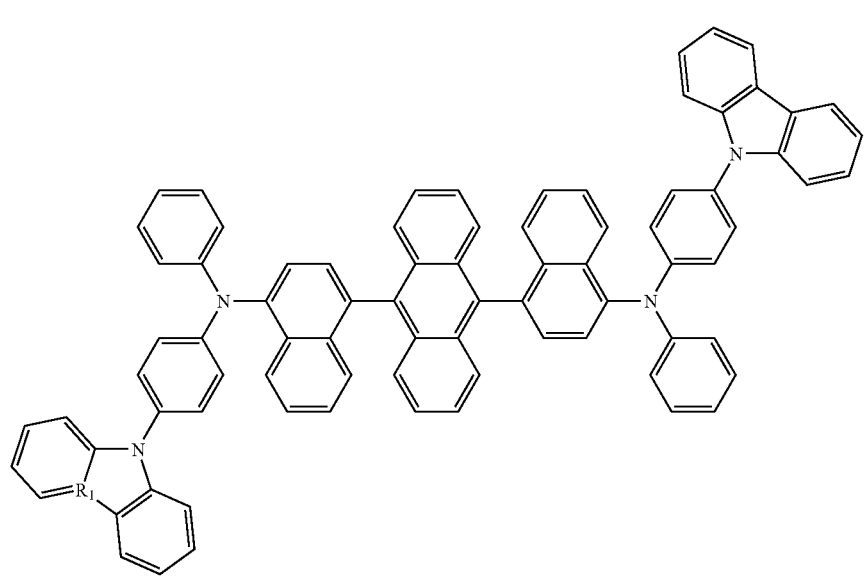
(8)
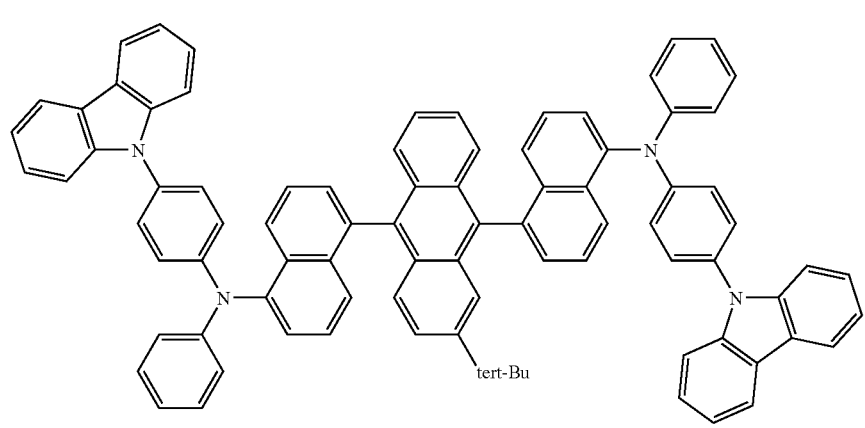
(9)
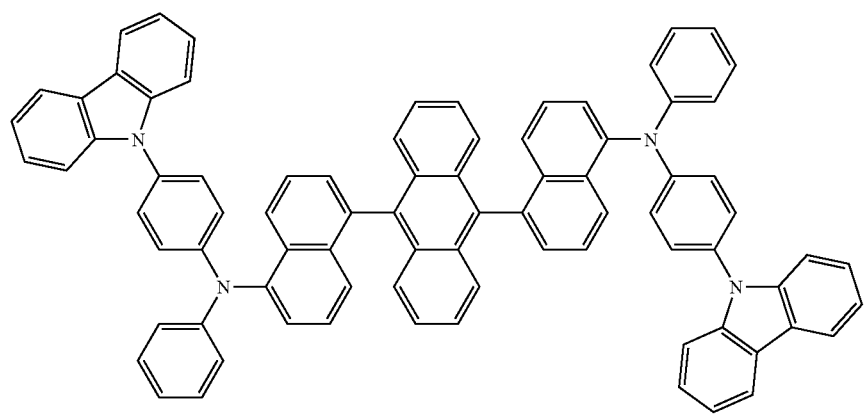
(10)

-continued
(11)
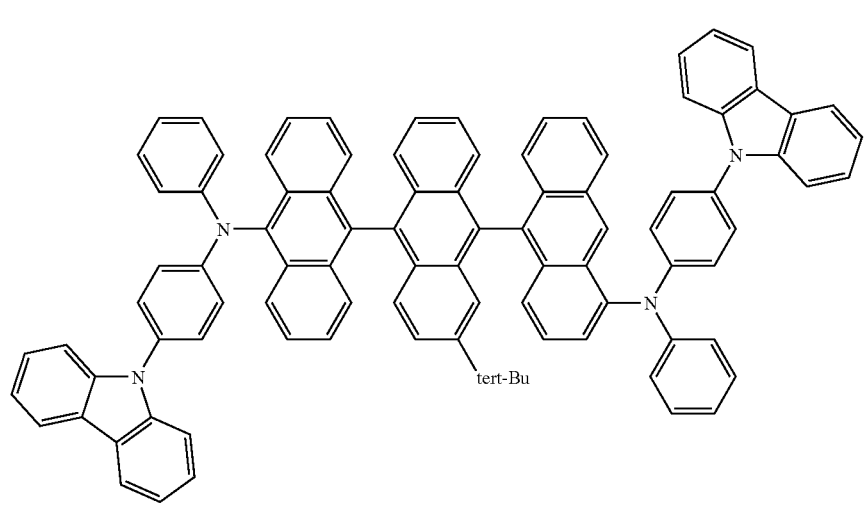
(12)
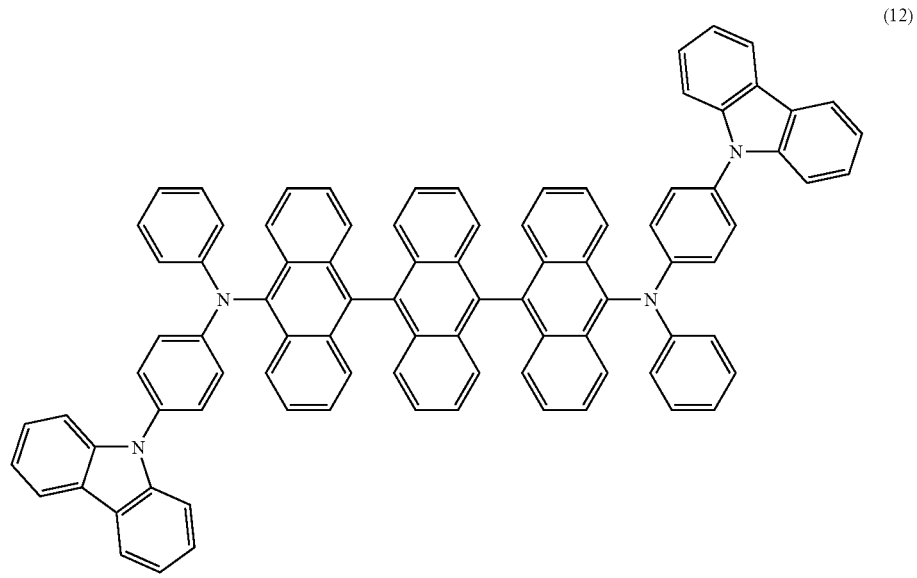
(13)
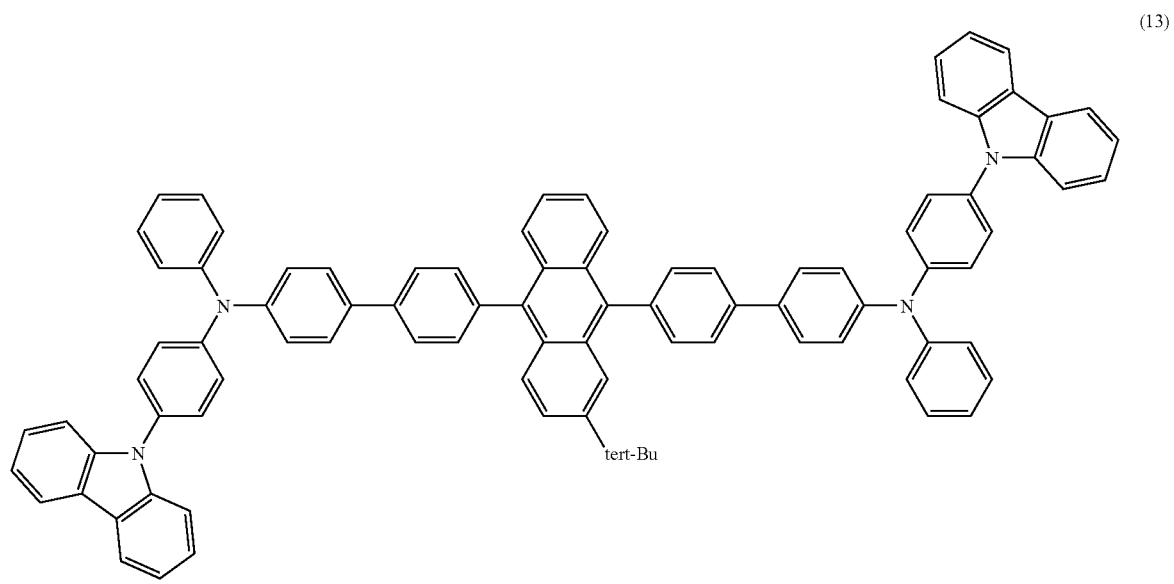

(14)
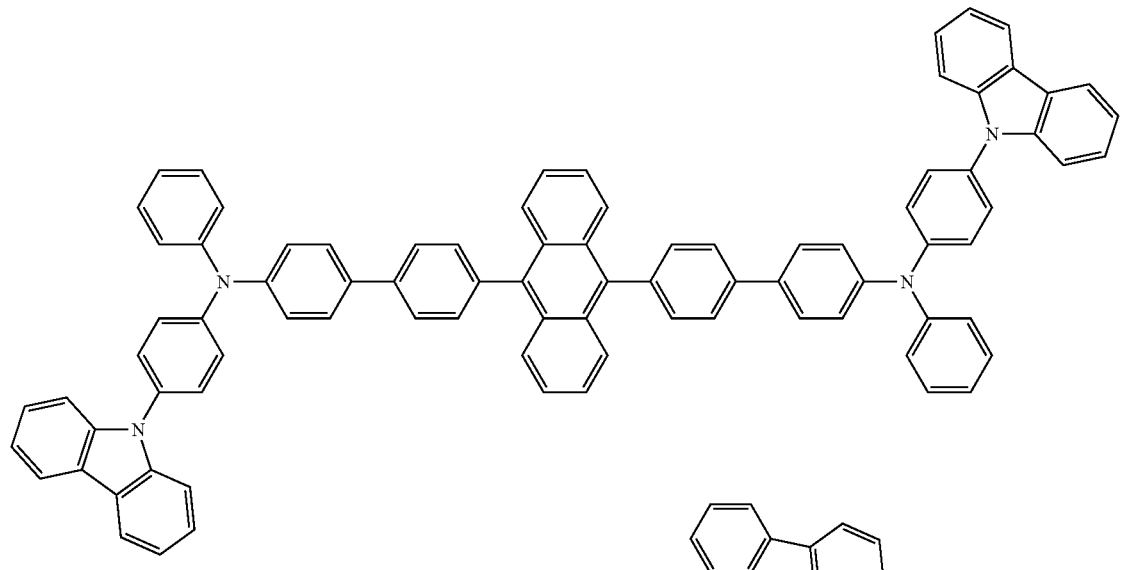
(15)
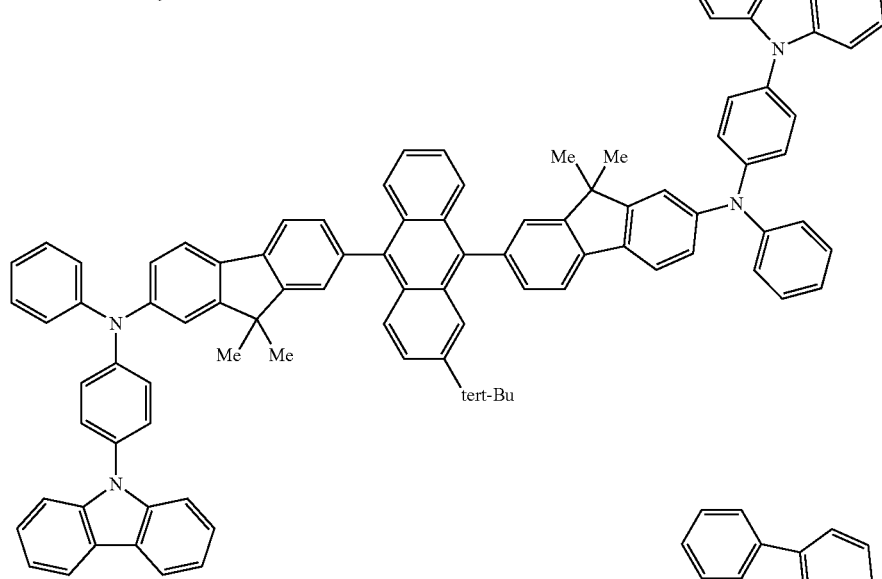
(16)
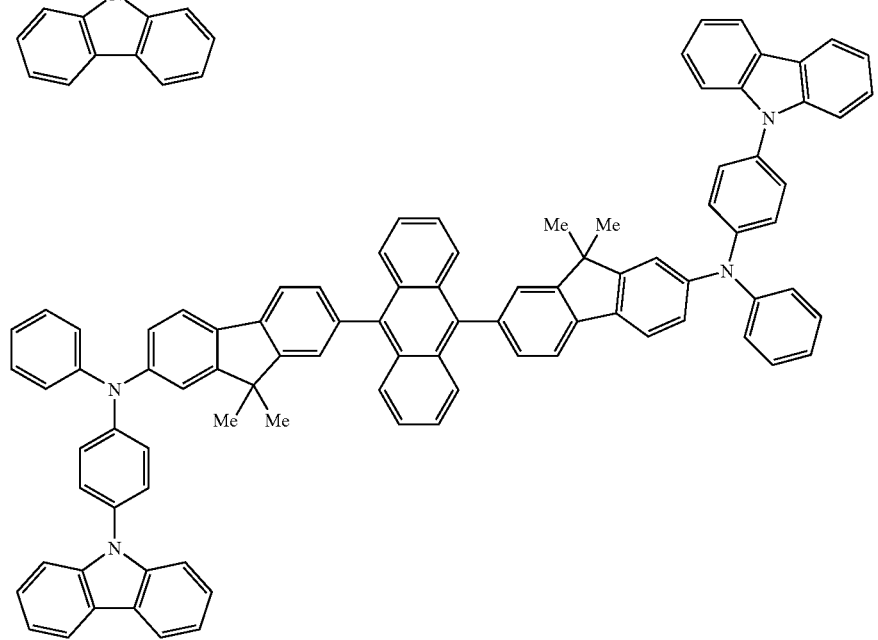

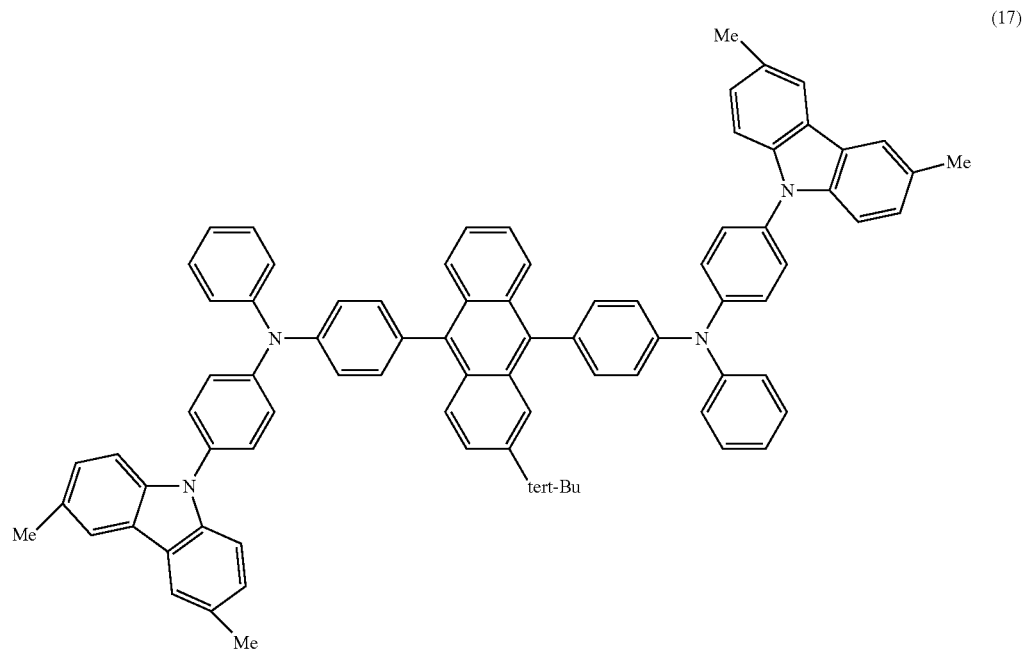
(17)
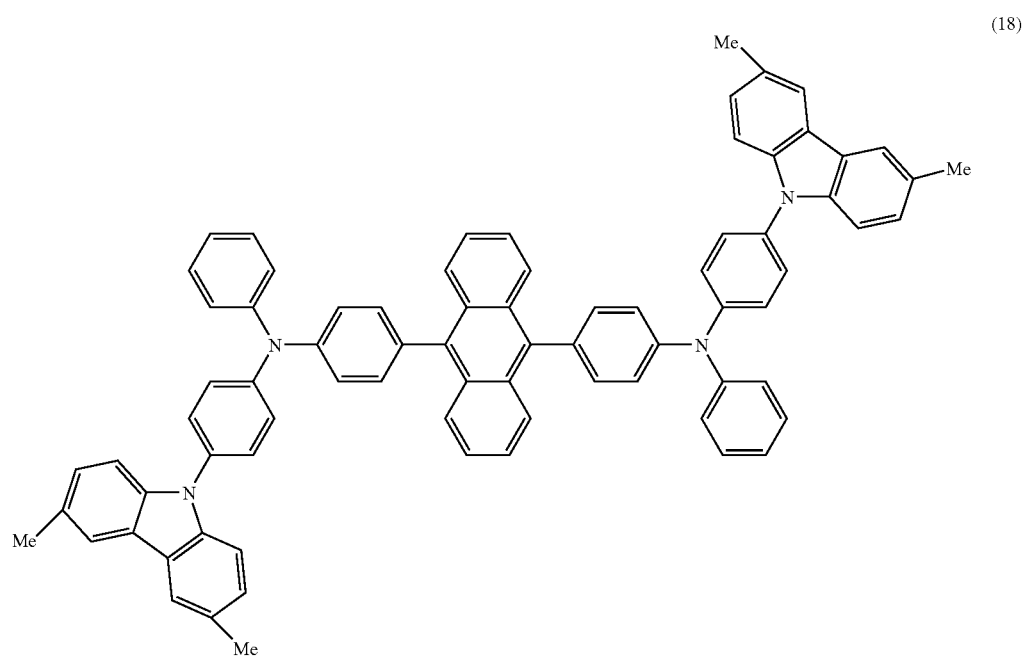
(18)

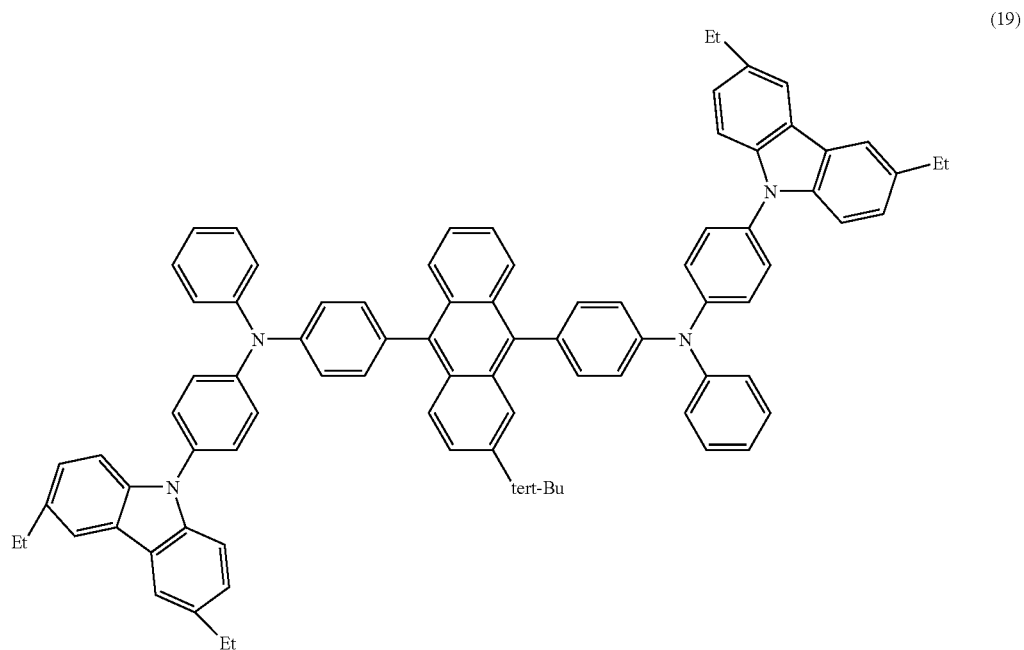
(19)
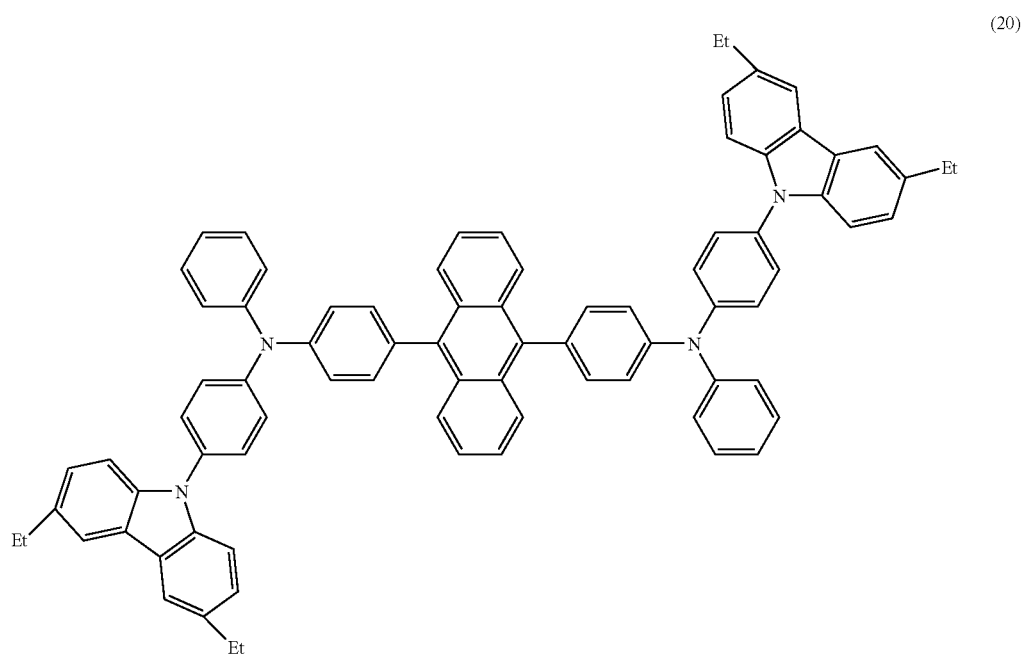
(20)

-continued
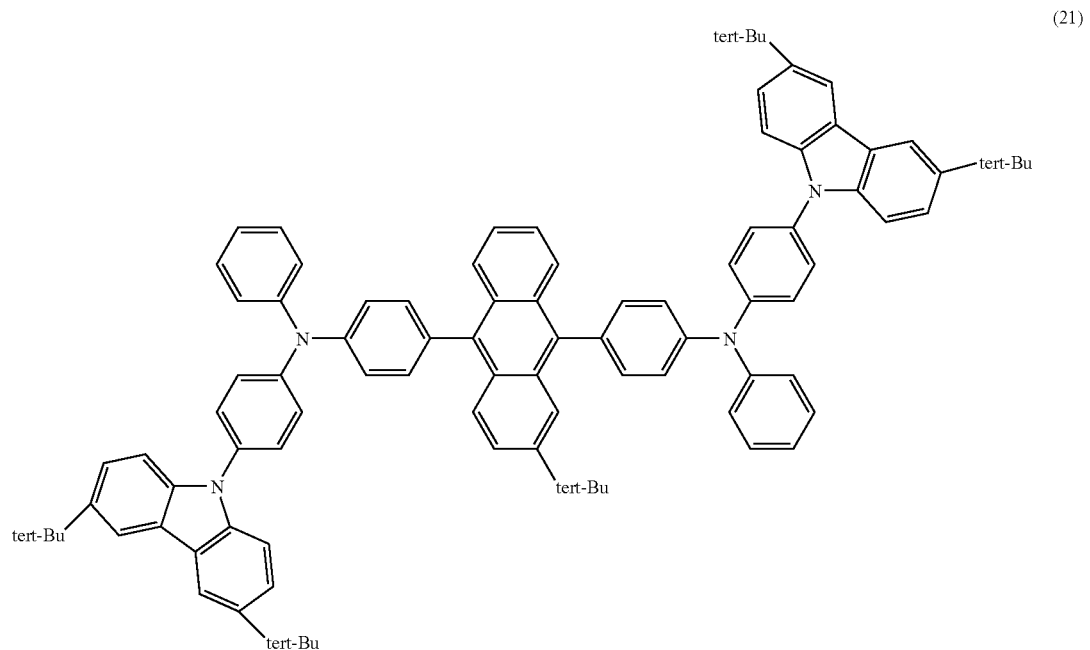
(21)
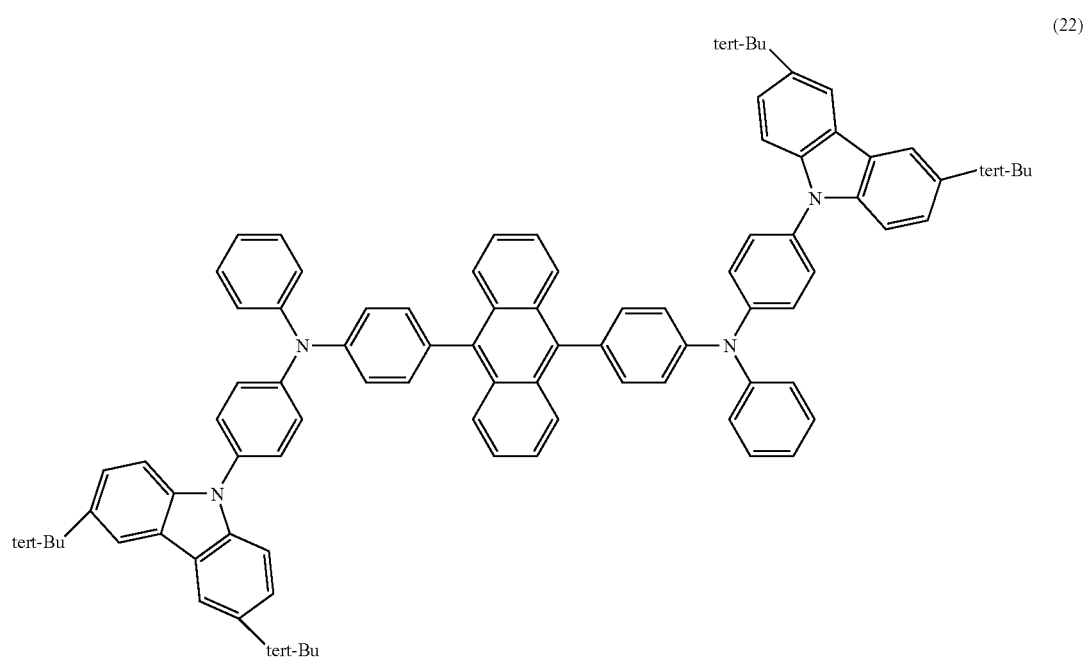
(22)

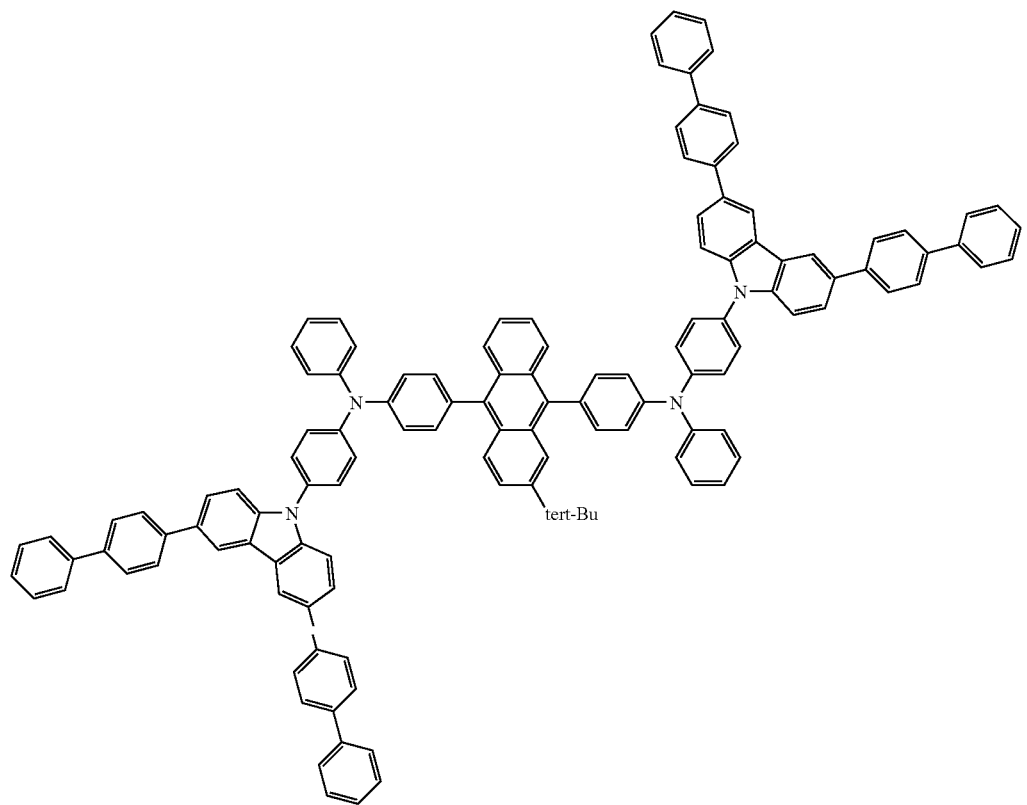
(23)
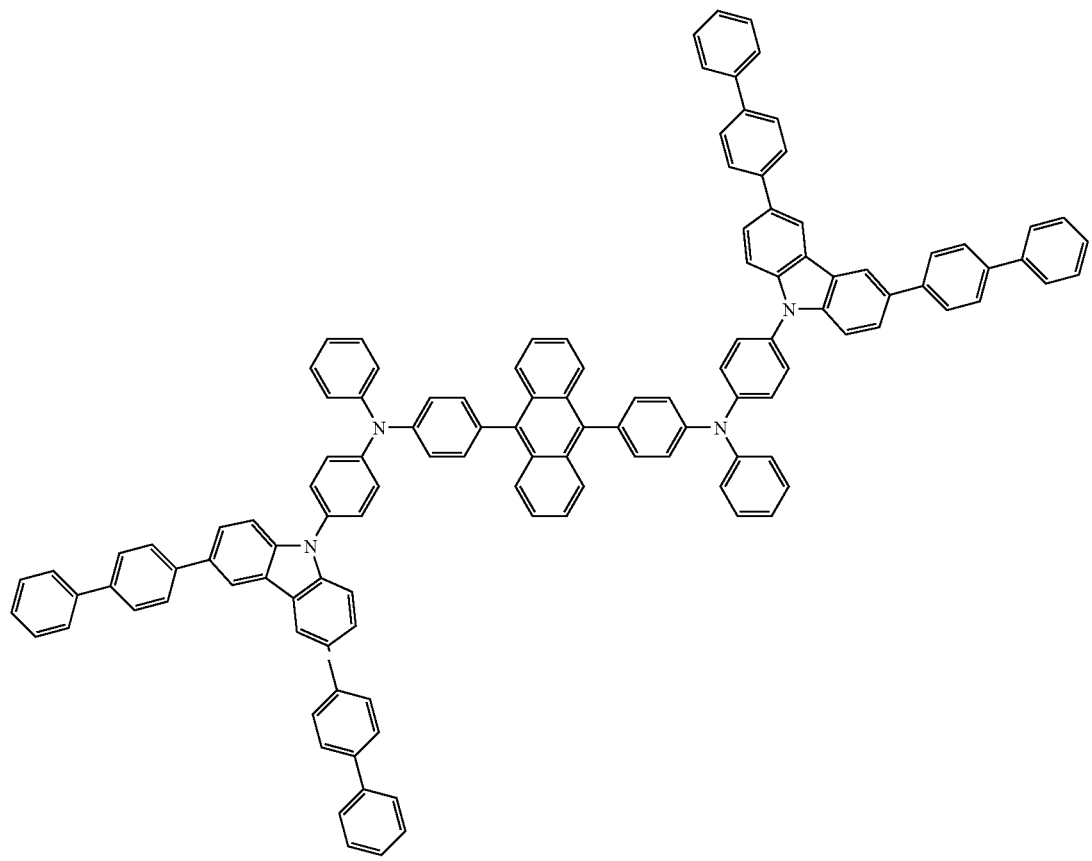
(24)

-continued
(25)
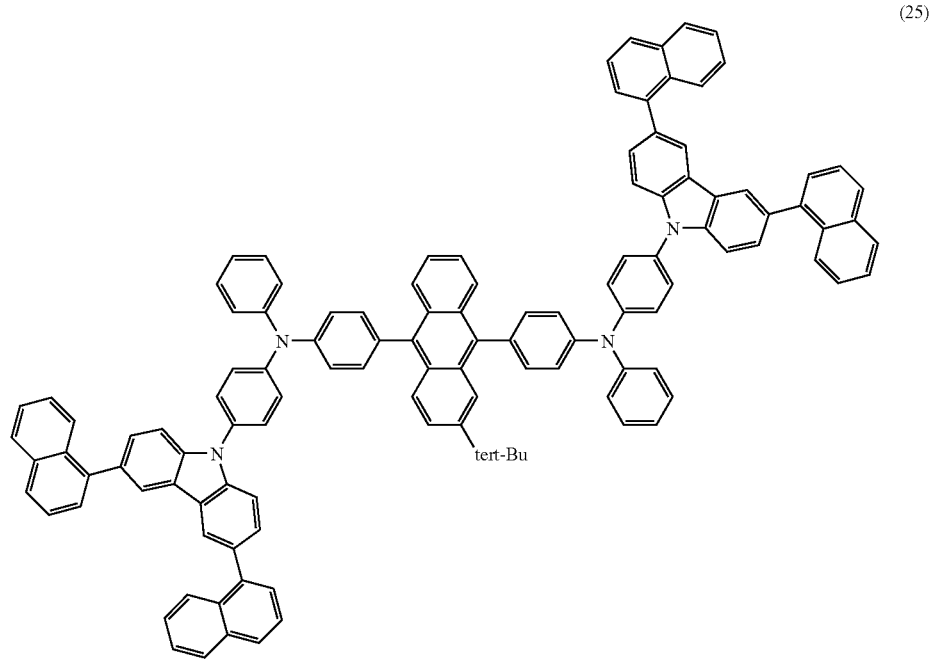
(26)
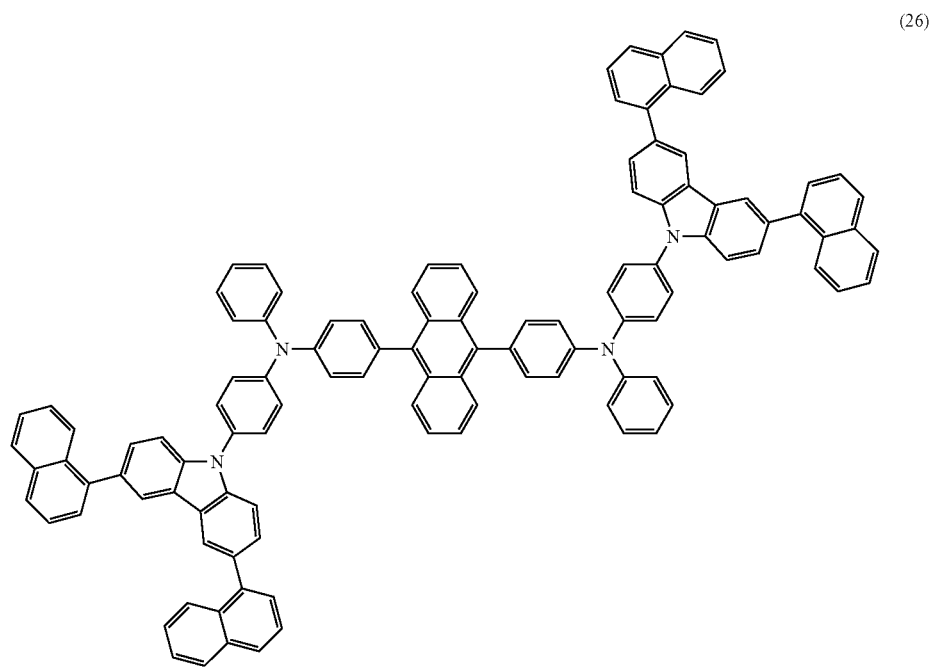

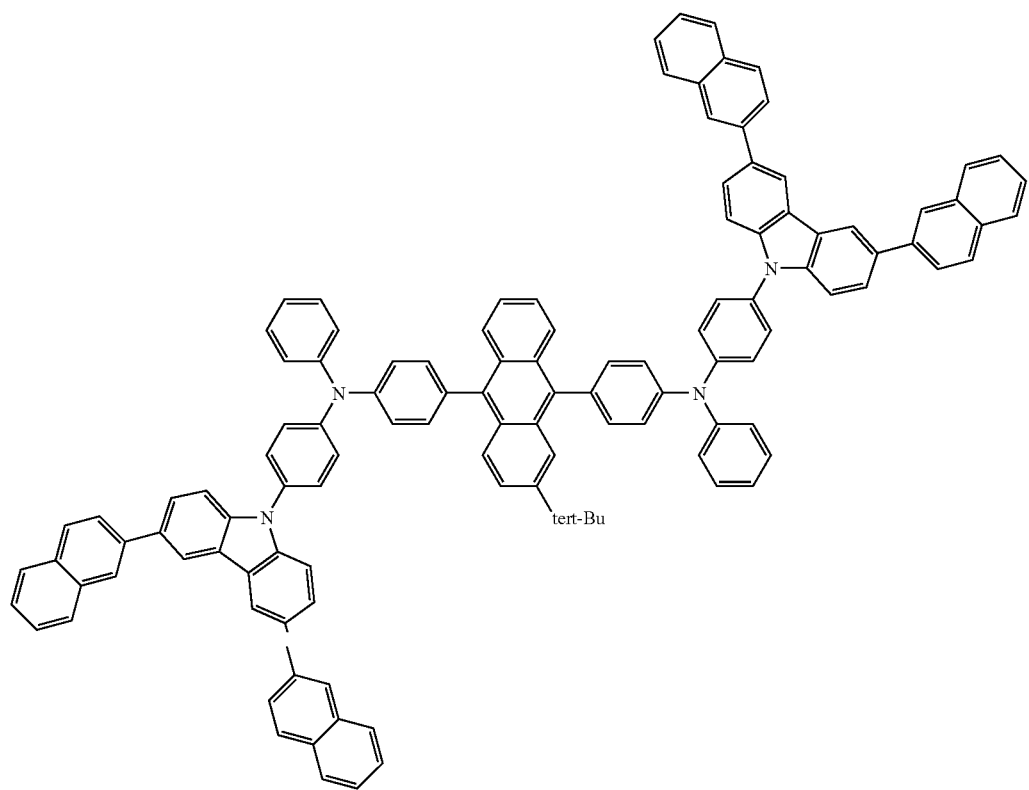
(27)
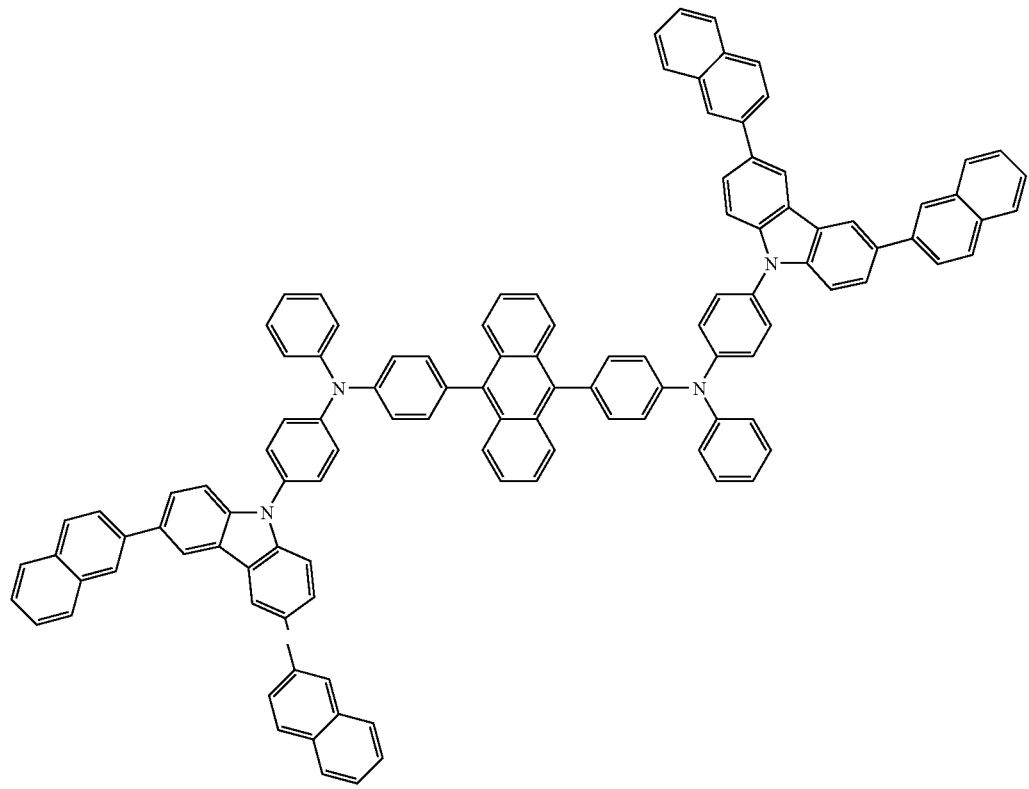
(28)

These anthracene derivatives can be obtained by, for example, performing a coupling reaction using a metal catalyst between a compound A and a compound B as represented by the following synthetic scheme (a-1). The compound A contains anthracene in a skeleton, such as 9,10-bis(dibromoaryl)anthracene, while the compound B contains N-[4-(9-carbazolyl)phenyl]-N-phenylamine in a skeleton. Further, a method for synthesizing an anthracene derivative of the present invention is not limited to the synthetic method described here and the anthracene derivative of the present invention can be synthesized by other synthetic methods.

In the synthetic scheme (a-1), $R^{14}$ represents hydrogen or tert-butyl. $R^{15}$ represents any one group selected from hydrogen, an alkyl group having 1 to 4 carbon atoms such as methyl, ethyl, or tert-butyl, and an aryl group having 1 to 12 carbon atoms such as phenyl, biphenyl, or naphthyl. The aryl group may have a substituent or no substituent. $X^3$ represents an arylene group having 6 to 15 carbon atoms such as phenylene, naphthylene, anthrylene, or 9,9-dimethylfluorene-2,7-diyl.

The compound A can be obtained by using dibromoarene (a compound C) and a compound containing anthraquinone in a skeleton as raw materials, as represented by a synthetic scheme (a-2). Also, the compound B can be obtained by conducting a coupling reaction using aniline and palladium catalyst after reacting a compound containing carbazole in a skeleton and 1,4-dibromobenzene to synthesize a compound containing N-(4-bromophenyl) carbazole in a skeleton, as represented by a synthetic scheme (a-3).

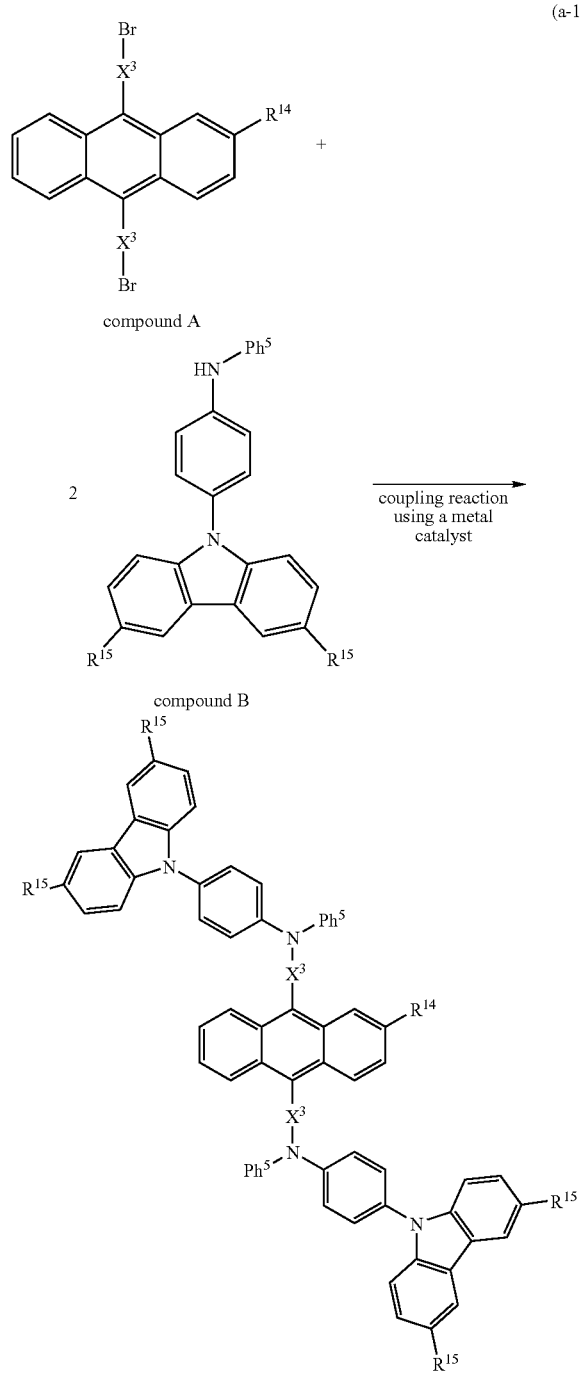

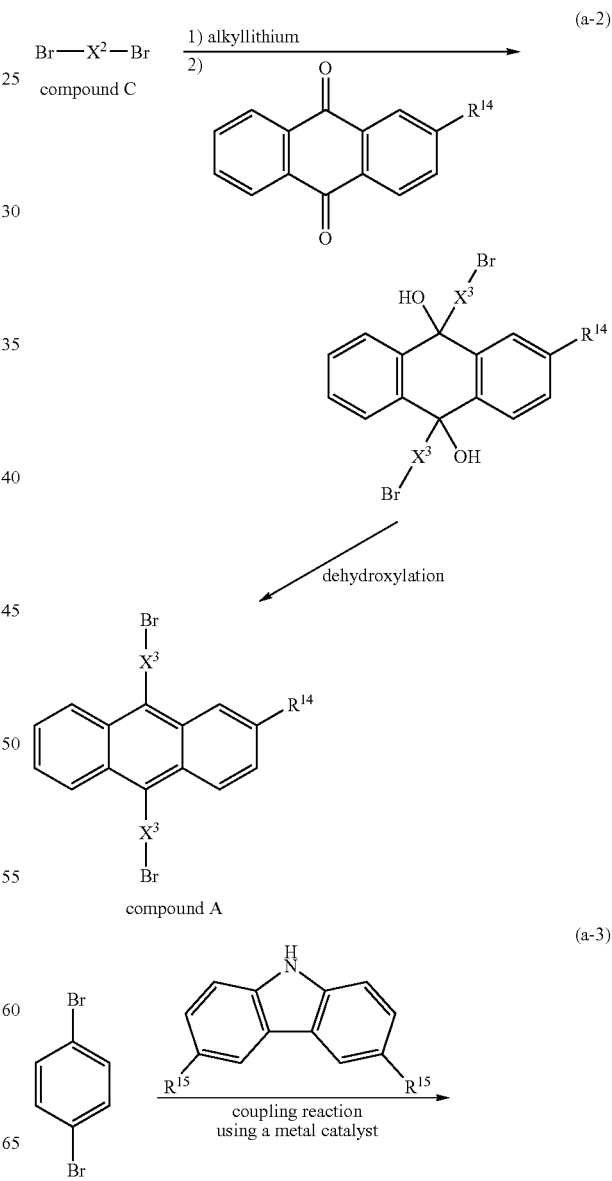

-continued

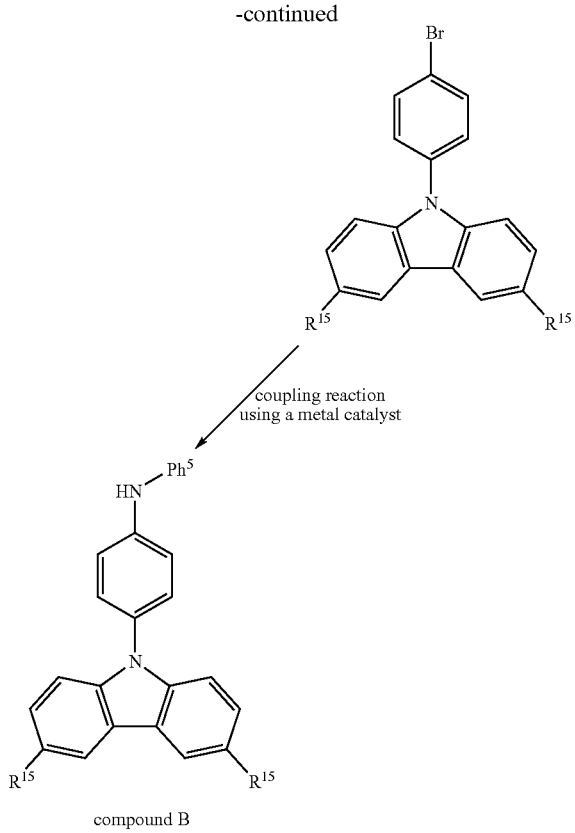

compound B

Although 9,10-bis(bromaryl) anthracene is used as the compound A which has an anthracene skeleton in this embodiment mode, 9,10-bis(iodoaryl) anthracene or the like may also be used. In the synthetic scheme (a-2), the 9,10-bis(iodoaryl) anthracene can be obtained by using diiodoarene such as 1,5-diiodonaphthalene or 2,7-diiodo-9,9-dimethylfluorene instead of the compound C. Furthermore, the 1,5-diiodonaphthalene, the 2,7-diiodo-9,9-dimethylfluorene, and the like can be obtained by performing synthesis in the following manner. Firstly, the 1,5-diiodonaphthalene can be obtained as follows: an amino group contained in 1,5-diaminonaphthalene is changed into diazonium salt using sodium nitrite and concentrated sulfuric acid and the diazonium salt is substituted for iodine using potassium iodide. The 2,7-diiodo-9,9-dimethylfluorene can be obtained as follows: a second position and a seventh position of fluorene are iodized by using orthoperiodic acid, and then a ninth position of the iodized fluorene is dimethylized by adding a sodium hydroxide solution, benzyltrimethylammonium chloride, and iodomethane in dimethylsulfoxide (abbreviation: DMSO).

As set forth above, an anthracene derivative of the present invention is resistant to repetition of an oxidation reaction. In some cases, the anthracene derivative is also resistant to repetition of a reduction reaction as well as the repetition of an oxidation reaction. In addition, the anthracene derivative of the present invention described above can emit blue light. Therefore, the anthracene derivative can be used as a light-emitting substance for manufacturing a blue light-emitting element. Since the anthracene derivative of the present invention described above has a large energy gap between the HOMO level and the LUMO level, the anthracene derivative of the present invention can be used as a substance for dispersing a light-emitting substance which emits red light to blue light, or, a so-called host material. Utilizing the anthracene derivative of the present invention as a light-emitting substance or a host material makes it possible to obtain a light-emitting element having fewer changes in a property of the host material due to the repetition of an oxidation reaction, wherein the increase in driving voltage due to accumulation of light-emitting periods and the like are suppressed.

Embodiment Mode 2

One mode of a light-emitting element using an anthracene derivative of the present invention as a light-emitting substance will be described with reference to FIG. 1.

A light-emitting element having a light-emitting layer 113 between a first electrode 101 and a second electrode 102 is shown in FIG. 1. The light-emitting layer 113 contains an anthracene derivative of the present invention represented by any one, of the general formulas (1) to (7) and the structural formulas (1) to (28).

In such a light-emitting element, a hole injected from the first electrode 101 side and an electron injected from the second electrode 102 side are recombined at the light-emitting layer 113, which makes the anthracene derivative of the present invention excited. The anthracene derivative of the present invention in the excited state emits light when returning to a ground state. Thus, the anthracene derivative of the present invention serves as a light-emitting substance.

The light-emitting layer 113 is preferably a layer in which an anthracene derivative of the present invention is dispersed in a layer including a substance having a larger energy gap than that of the anthracene derivative of the present invention. This can prevent light emitted from the anthracene derivative of the present invention from going out depending on the concentration. It is to be noted that the energy gap indicates an energy gap between the LUMO level and the HOMO level.

Although the substance used for dispersing the anthracene derivative of the present invention is not particularly limited, a metal complex such as bis[2-(2-hydroxyphenyl)pyridinato] zinc (abbreviation: $Znpp_2$) and bis[2-(2-hydroxyphenyl)benzoxazolato] zinc ($Zn(BOX)_2$), and the like are preferable in addition to an anthracene derivative such as 2-tert-butyl-9,10-di(2-naphthyl) anthracene (abbreviation: t-BuDNA) and a carbazole derivative such as 4,4'-di(N-carbazolyl) biphenyl (abbreviation: CBP). One or more substances may be selected from the above mentioned substances and mixed with an anthracene derivative of the present invention so as to disperse the anthracene derivative of the present invention in the one or more substances. Such a layer in which a plurality of compounds are mixed can be formed by using a co-evaporation method. The co-evaporation is an evaporation method in which raw materials are vaporized from a plurality of evaporation sources provided in one processing chamber and the vaporized raw materials are mixed in a gaseous state so as to be deposited onto an object.

Also, the first electrode 101 and the second electrode 102 are not particularly limited. They can be formed by using gold (Au), platinum (Pt), nickel (Ni), tungsten (W), chromium (Cr), molybdenum (Mo), iron (Fe), cobalt (Co), copper (Cu), palladium (Pd) or the like, in addition to indium tin oxide (ITO), indium tin oxide containing silicon oxide, or indium oxide containing 2 to 20 wt % of zinc oxide. The first electrode 101 can also be formed using an alloy of magnesium and silver, an alloy of aluminum and lithium, or the like, in addition to aluminum. Further, a method for forming the first electrode 101 and the second electrode 102 is not particularly limited. For example, the first electrode 101 and the second electrode 102 can be formed by using a sputtering method, an evaporation method, or the like. To take out light to the outside, one or both of the first electrode 101 and the second electrode 102 is/are preferably formed by using indium tin oxide or the like, or using silver, aluminum, or the like to have a thickness of several nm to several tens nm such that visible light passes therethrough.

As shown in FIG. 1, a hole-transporting layer 112 may be provided between the first electrode 101 and the light-emitting layer 113. The hole-transporting layer is a layer having a function of transporting holes injected from the first electrode 101 side to the light-emitting layer 113. Thus, providing the hole-transporting layer 112 makes it possible to isolate the first electrode 101 from the light-emitting layer 113. Consequently, it is possible to prevent light emission from going out due to a metal contained in the first electrode 101 and the like. The hole-transporting layer, is preferably formed using a substance having a high hole-transporting property. In particular, a substance having a hole mobility of $1 \times 10^{-6}$ cm$^2$/Vs or more is preferably used for forming the hole-transporting layer. The substance having a high hole-transporting property is a substance of which the hole mobility is higher than the electron mobility and a ratio of the hole mobility to the electron mobility (i.e., the hole mobility/the electron mobility) is more than 100. As a specific example of a substance that can be used for forming the hole-transporting layer 112, 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4',4''-tris(N,N-diphenylamino) triphenylamine (abbreviation: TDATA), 4,4',4''-tris[N-(3-methylphenyl)-N-phenylamino]triphenylamine (abbreviation: MTDATA), 4,4'-bis{N-[4-(N,N-di-m-tolylamino)phenyl]-N-phenylamino}biphenyl (abbreviation: DNTPD), 1,3,5-tris[N,N-di(m-tolyl)amino]benzene (abbreviation: m-MTDAB), 4,4',4''-tris(N-carbazolyl)triphenylamine (abbreviation: TCTA), phthalocyanine (abbreviation: H$_2$Pc), copper phthalocyanine (abbreviation: CuPc), vanadyl phthalocyanine (abbreviation: VOPc), and the like can be given. Further, the hole-transporting layer 112 may be a layer having a multilayer structure that is formed by combining two or more layers including the above mentioned substances.

Moreover, as shown in FIG. 1, an electron-transporting layer 114 may be provided between the second electrode 102 and the light-emitting layer 113. The electron-transporting layer is a layer having a function of transporting electrons injected from the second electrode 102 to the light-emitting layer 113. Thus, providing the electron-transporting layer 114 makes it possible to isolate the second electrode 102 from the light-emitting layer 113. Consequently, it is possible to prevent light emission from going out due to a metal contained in the second electrode 102 and the like. The electron-transporting layer is preferably formed using a substance having a high electron-transporting property. In particular, a substance having an electron mobility of $1 \times 10^{-6}$ cm$^2$/Vs or more is preferably used for forming the electron-transporting layer. The substance having a high electron-transporting property is a substance of which the electron mobility is higher than the hole mobility and a ratio of the electron mobility to the hole mobility (i.e., the electron mobility/the hole mobility) is more than 100. As a specific example of a substance that can be used for forming the electron-transporting layer 114, a metal complex such as tris(8-quinolinolato) aluminum (abbreviation: Alq$_3$), tris(4-methyl-8-quinolinolato) aluminum (abbreviation: Almq$_3$), bis(10-hydroxybenzo [h]-quinolinato) beryllium (abbreviation: BeBq$_2$), bis(2-methyl-8-quinolinolato)-4-phenylphenolato-aluminum (abbreviation: BAlq), bis[2-(2-hydroxyphenyl)benzoxazolato] zinc (abbreviation: Zn(BOX)$_2$), and bis[2-(2-hydroxyphenyl)benzothiazolato] zinc (abbreviation: Zn(BTZ)$_2$) can be given. In addition, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), 4,4-bis(5-methylbenzoxazole-2-yl) stilbene (abbreviation: BzOs), and the like can be given. Further, the electron-transporting layer 114 may be a layer having a multilayer structure that is formed by combining two or more layers including the above mentioned substances.

Each of the hole-transporting layer 112 and the electron-transporting layer 114 may be formed using a bipolar substance, in addition to the above mentioned substances. The bipolar substance is a substance of which when comparing electron mobility and hole mobility, a ratio of the mobility of one carrier to the mobility of the other carrier is 100 or less, preferably 10 or less. As the bipolar substance, for example, 2,3-bis(4-diphenylaminophenyl) quinoxaline (abbreviation: TPAQn) and the like can be given. Among bipolar substances, in particular, a substance having a hole and electron mobility of $1 \times 10^{-6}$ cm$^2$/Vs or more is preferably used. Also, the hole-transporting layer 112 and the electron-transporting layer 114 may be formed using the same bipolar substance.

As shown in FIG. 1, a hole-injecting layer 111 may also be provided between the first electrode 101 and the hole-transporting layer 112. The hole-injecting layer 111 is a layer having a function of helping injection of holes into the hole-transporting layer 112 from the first electrode 101. Providing the hole-injecting layer 111 makes it possible to reduce the difference in ionizing potential between the first electrode 101 and the hole-transporting layer 112 so that holes are easily injected. The hole-injecting layer 111 is preferably formed by using a substance of which the ionizing potential is lower than that of a substance which forms the hole-transporting layer 112 and higher than that of a substance which forms the first electrode 101, or a substance in which an energy band is bent when being provided as a thin film with a thickness of 1 to 2 nm between the hole-transporting layer 112 and the first electrode 101. As a specific example of a substance that can be used for forming the hole-injecting layer 111, phthalocyanine (abbreviation: H$_2$Pc) and a phthalocyanine compound such as copper phthalocyanine (abbreviation: CuPc), a polymer such as a poly(ethylene dioxythiophene)/poly(styrene sulfonate) aqueous solution (abbreviation: PEDOT/PSS), or the like can be given. That is, the hole-injecting layer 111 can be formed by selecting a substance by which the ionizing potential of the hole-injecting layer 111 is relatively lower than the ionizing potential of the hole-transporting layer 112 from among substances having hole-transporting properties. Further, in the case of providing the hole-injecting layer 111, the first electrode 101 is preferably formed using a substance having a high work function such as indium tin oxide.

An electron-injecting layer 115 may also be provided between the second electrode 102 and the electron-transporting layer 114 as shown in FIG. 1. The electron-injecting layer 115 is a layer having a function of helping injection of electrons into the electron-transporting layer 114 from the second electrode 102. Providing the electron-injecting layer 115 makes it possible to reduce the difference in electron affinity between the second electrode 102 and the electron-transporting layer 114 so that electrons are easily injected. The electron-injecting layer 115 is preferably formed using a substance of which the electron affinity is higher than a substance which forms the electron-transporting layer 114 and lower than a substance which forms the second electrode 102, or a substance of which an energy band is bent when being provided as a thin film with a thickness of 1 to 2 nm between the electron-transporting layer 114 and the second electrode 102. As a specific example of a substance that can be used for forming the electron-injecting layer 115, an inorganic material such as alkali metal, alkali earth metal, fluoride of alkali metal, fluoride of alkali earth metal, alkali metal oxide, or alkali earth metal oxide can be given. In addition to the inorganic material, the substances which can be used for forming the electron-transporting layer 114 such as BPhen, BCP, p-EtTAZ, TAZ, and BzOs can also be used as a substance for forming the electron-injecting layer 115, by selecting from among these substances a substance having higher electron affinity than a substance used for forming the electron-transporting layer 114. That is to say, a substance where electron affinity of the electron-injecting layer 115 is relatively higher than that of the electron-transporting layer 114 is selected from substances having electron-transporting properties, so that the electron-injecting layer 115 can be formed. Further, in the case of providing the electron-injecting layer 115, the first electrode 101 is preferably formed using a substance having a low work function such as aluminum.

In the light-emitting element of the present invention as described above, the hole-injecting layer 111, the hole-transporting layer 112, the light-emitting layer 113, the electron-transporting layer 114, and the electron-injecting layer 115 may be formed by any method such as an evaporation method, an ink-jet method, or a coating method, respectively. Further, the first electrode 101 and the second electrode 102 may be formed by any method such as a sputtering method or an evaporation method.

Moreover, a hole-generating layer may be provided instead of the hole-injecting layer 111. An electron-generating layer may be provided instead of the electron-injecting layer 115.

The hole-generating layer is a layer generating holes. The hole-generating layer can be formed by mixing a substance of which the hole mobility is higher than the electron mobility and a substance exhibiting an electron-accepting property with respect to the substance of which the hole mobility is higher than the electron mobility. The hole-generating layer can also be formed by mixing at least one substance selected from bipolar substances and a substance exhibiting an electron-accepting property with respect to the selected bipolar substance. As the substance of which the hole mobility is higher than the electron mobility, the similar substance to the substance that can be used for forming the hole-transporting layer 112 can be used. As the bipolar substance, a bipolar substance such as TPAQn can be used. Moreover, among substances having higher hole mobility than electron mobility and bipolar substances, in particular, a substance containing triphenylamine in skeleton is preferably used. Using the substance containing triphenylamine in the skeleton makes it possible to generate holes easily. As the substance exhibiting the electron-accepting property, metal oxide such as molybdenum oxide, vanadium oxide, ruthenium oxide, or rhenium oxide is preferably used.

Further, the electron-generating layer is a layer generating electrons. The electron-generating layer can be formed by mixing a substance of which the electron mobility is higher than the hole mobility and a substance exhibiting an electron-donating property with respect to the substance of which the electron mobility is higher than the hole mobility. The electron-generating layer can also be formed by mixing at least one substance selected from bipolar substances and a substance exhibiting an electron-donating property with respect to the selected bipolar substance. Here, as the substance of which the electron mobility is higher than the hole mobility, the similar substance to a substance that can be used for forming the electron-transporting layer 114 can be used. As the bipolar substance, the above mentioned bipolar substances such as TPAQn can be used. As the substance exhibiting an electron-donating property, a substance selected from alkali metal and alkali earth metal, specifically lithium (Li), calcium (Ca), sodium (Na), kalium (Ka), magnesium (Mg), or the like can be used. Moreover, at least one substance selected from lithium oxide ($Li_2O$), calcium oxide (CaO), sodium oxide ($Na_2O$), kalium oxide ($K_2O$), and magnesium oxide (MgO) can be used as the substance exhibiting an electron-donating property. In addition, alkali metal fluoride or alkali earth metal fluoride, or specifically, at least one substance selected from lithium fluoride (LiF), cesium fluoride (CsF) and calcium fluoride ($CaF_2$) can be used as the substance exhibiting an electron-donating property. Further, alkali metal nitride, alkali earth metal nitride, and the like, or specifically, at least one substance selected from calcium nitride and magnesium nitride can be used as the substance exhibiting an electron donating property.

Since the light-emitting element of the present invention having the above described structure uses an anthracene derivative of the present invention, there are few changes in a characteristic of the light-emitting element due to changes in properties of a light-emitting substance caused by repetition of an oxidation reaction. As a result, the light-emitting element can emit light stably for a long time.

Embodiment Mode 3

When an anthracene derivative of the present invention is included in a light-emitting layer along with a light-emitting substance, the anthracene derivative can be used as a substance for dispersing the light-emitting substance, or, a so-called host material. In Embodiment Mode 3, a mode of a light-emitting element using an anthracene derivative of the present invention as a host material will be described with reference to FIG. 2.

Figure 2:
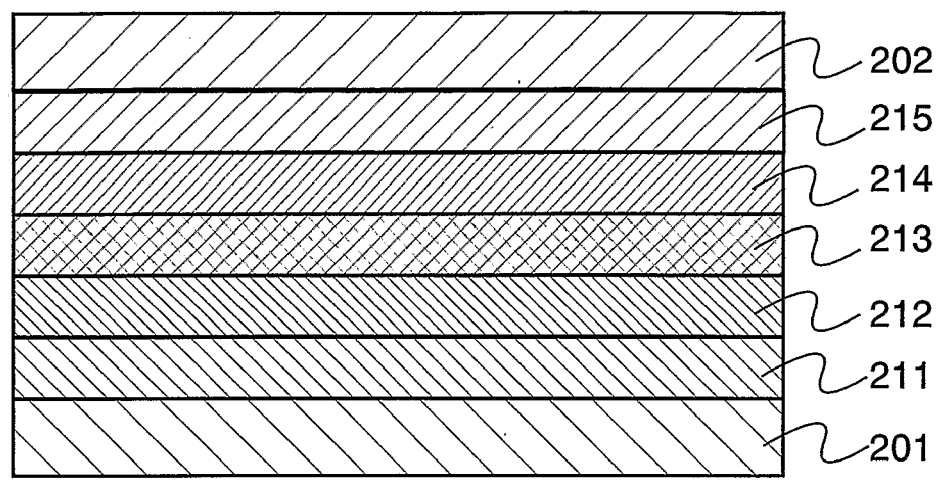
FIG. 2 explains a light-emitting element of the present invention.

FIG. 2 shows a light-emitting element having a light-emitting layer 213 between a first electrode 201 and a second electrode 202. A hole-injecting layer 211 and a hole-transporting layer 212 are provided between the first electrode 201 and the light-emitting layer 213 while an electron-transporting layer 214 and an electron-injecting layer 215 are provided between the second electrode 202 and the light-emitting layer 213. Further, a laminated-layer structure of the light-emitting element is not particularly limited. Whether the hole-injecting layer 211, the hole-transporting layer 212, the electron-transporting layer 214, the electron-injecting layer 215, and a layer other than these layers are provided or not may be selected appropriately. Furthermore, the hole-injecting layer 211, the hole-transporting layer 212, the electron-transporting layer 214, and the electron-injecting layer 215 may be the same as the hole-injecting layer 111, the hole-transporting layer 112, the electron-transporting layer 114, and the electron-injecting layer 115 described in Embodiment Mode 2, and therefore these layers will not be further described in this embodiment mode. Similarly, since the first electrode 201 and the second electrode 202 may be the same as the first electrode 101 and the second electrode 102 shown in Embodiment Mode 1, they will not be further described here.

In the light-emitting element of this embodiment mode, the light-emitting layer 213 contains an anthracene derivative of the present invention represented by any one of the general formulas (1) to (7) and the structural formulas (1) to (28) and a light-emitting substance having a spectrum peak in a range of 450 to 700 nm, preferably 480 nm to 600 nm. More specifically, the light-emitting substance is dispersed in a layer including the anthracene derivative of the present invention. By using a combination of such a substance having a spectrum peak in a range of 450 to 700 nm, preferably 480 nm to 600 nm, and the anthracene derivative of the present invention, a light-emitting element in which light generated in a host material is difficult to be mixed and light generated in a light-emitting substance can be selectively taken out can be obtained.

In addition, the anthracene derivative of the present invention is resistant to repetition of an oxidation reaction. In some cases, the anthracene derivative of the present invention is resistant to repetition of a reduction reaction as well as the repetition of an oxidation reaction. Therefore, in the case of a light-emitting element in which a host material is excited and light is emitted by moving the thus excited energy to a light-emitting substance, a light-emitting element can be obtained in which changes in a characteristic of the host material due to repetition of an oxidation reaction are few and in which the increase in driving voltage due to accumulation of light-emitting periods and the like are reduced.

Embodiment Mode 4

Since the light-emitting elements of the present invention described in Embodiment Modes 2 and 3 are resistant to repetition of an oxidation reaction (which are also sometimes resistant to repetition of a reduction reaction) and can emit light for a long time in a favorable state, a light-emitting device that can display favorable images for a long time can be obtained by using the light-emitting elements of the present invention.

In this embodiment mode, circuit structures and driving methods of a light-emitting device having a display function will be described with reference to FIGS. 3, 4, 5 and 6.

Figure 3:
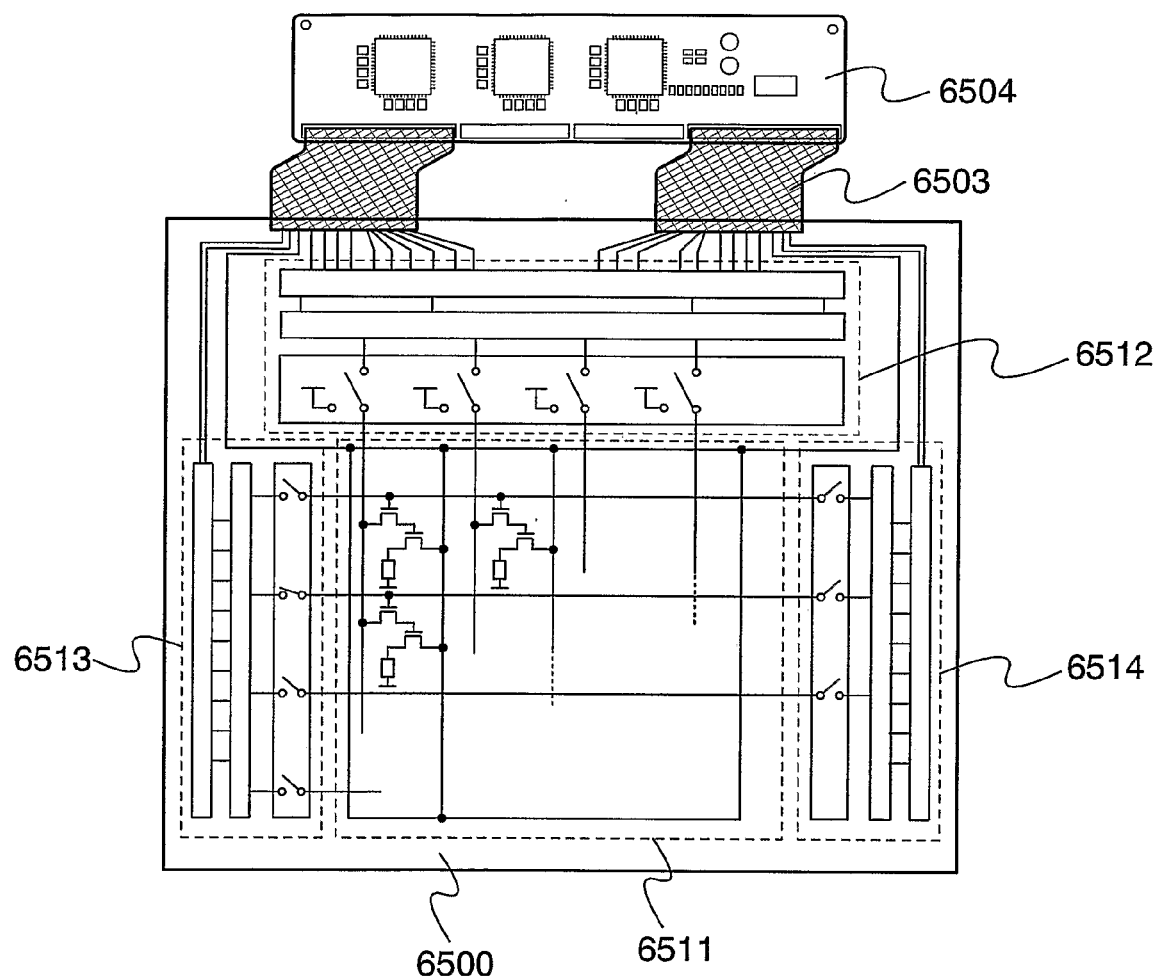
FIG. 3 explains a mode of a light-emitting device of the present invention.

FIG. 3 is a schematic top view of a light-emitting device to which the present invention has been applied. In FIG. 3, a pixel portion 6511, a source signal line driver circuit 6512, a writing gate signal line driver circuit 6513, and an erasing gate signal line driver circuit 6514 are provided over a substrate 6500. The source signal line driver circuit 6512, the writing gate signal line driver circuit 6513, and the erasing gate signal line driver circuit 6514 are connected to FPCs (flexible printed circuits) 6503, which are external input terminals, through wiring groups, respectively. The source signal line driver circuit 6512, the writing gate signal line driver circuit 6513, and the erasing gate signal line driver circuit 6514 receive video signals, clock signals, start signals, reset signals and the like from the FPCs 6503, respectively. The FPCs 6503 have printed wiring boards (PWBs) 6504 attached thereto. Further, the driver circuit portion is not necessarily formed over the same substrate as the pixel portion 6511. For example, the driver circuit portion may be provided outside of the substrate by utilizing a TCP where an IC chip is mounted over an FPC having a wiring pattern, or the like.

A plurality of source signal lines extending in columns are aligned in rows in the pixel portion 6511. Moreover, power supply lines are aligned in rows. A plurality of gate signal lines extending in rows are aligned in columns in the pixel portion 6511. In addition, a plurality of sets of circuits each including a light-emitting element are aligned in the pixel portion 6511.

Figure 4:
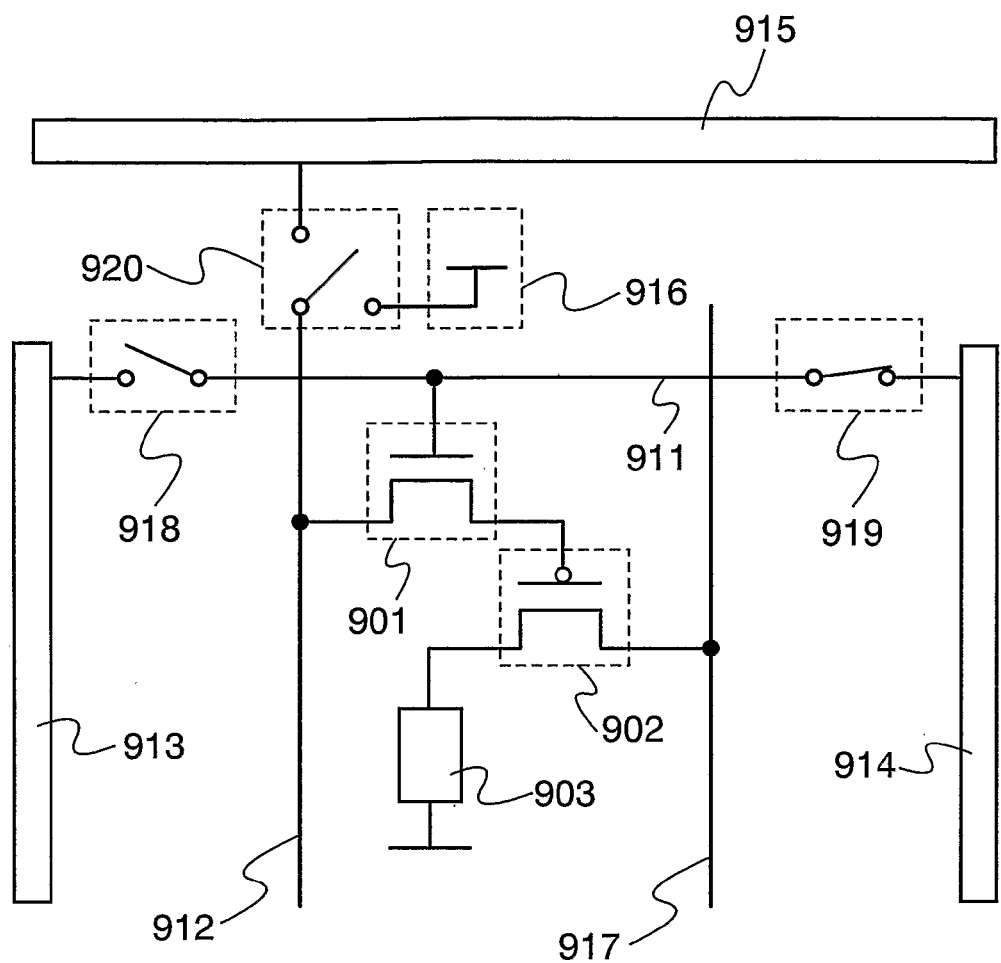
FIG. 4 explains a mode of a circuit included in a light-emitting device of the present invention.

FIG. 4 is a diagram showing a circuit for operating one pixel. The circuit shown in FIG. 4 comprises a first transistor 901, a second transistor 902, and a light-emitting element 903.

Each of the first transistor 901 and the second transistor 902 is a three-terminal element including a gate electrode, a drain region, and a source region. A channel region is interposed between the drain region and the source region. The region serving as the source region and the region serving as the drain region are changed depending on a structure of a transistor, an operational condition, and the like; therefore, it is difficult to determine which region serves as the source region or the drain region. Therefore, in this embodiment mode, the regions serving as the source or the drain are denoted as a first electrode and a second electrode, respectively.

A gate signal line 911 and a writing gate signal line driver circuit 913 are provided to be electrically connected or disconnected to each other by a switch 918. The gate signal line 911 and an erasing gate signal line driver circuit 914 are provided to be electrically connected or disconnected to each other by a switch 919. A source signal line 912 is provided to be electrically connected to either a source signal line driver circuit 915 or a power source 916 by a switch 920. A gate of the first transistor 901 is electrically connected to the gate signal line 911. The first electrode of the first transistor is electrically connected to the source signal line 912 while the second electrode thereof is electrically connected to a gate electrode of the second transistor 902. The first electrode of the second transistor 902 is electrically connected to a current supply line 917 while the second electrode thereof is electrically connected to one electrode included in the light-emitting element 903. Further, the switch 918 may be included in the writing gate signal line driver circuit 913. The switch 919 may also be included in the erasing gate signal line driver circuit 914. In addition, the switch 920 may be included in the source signal line driver circuit 915.

Figure 5:
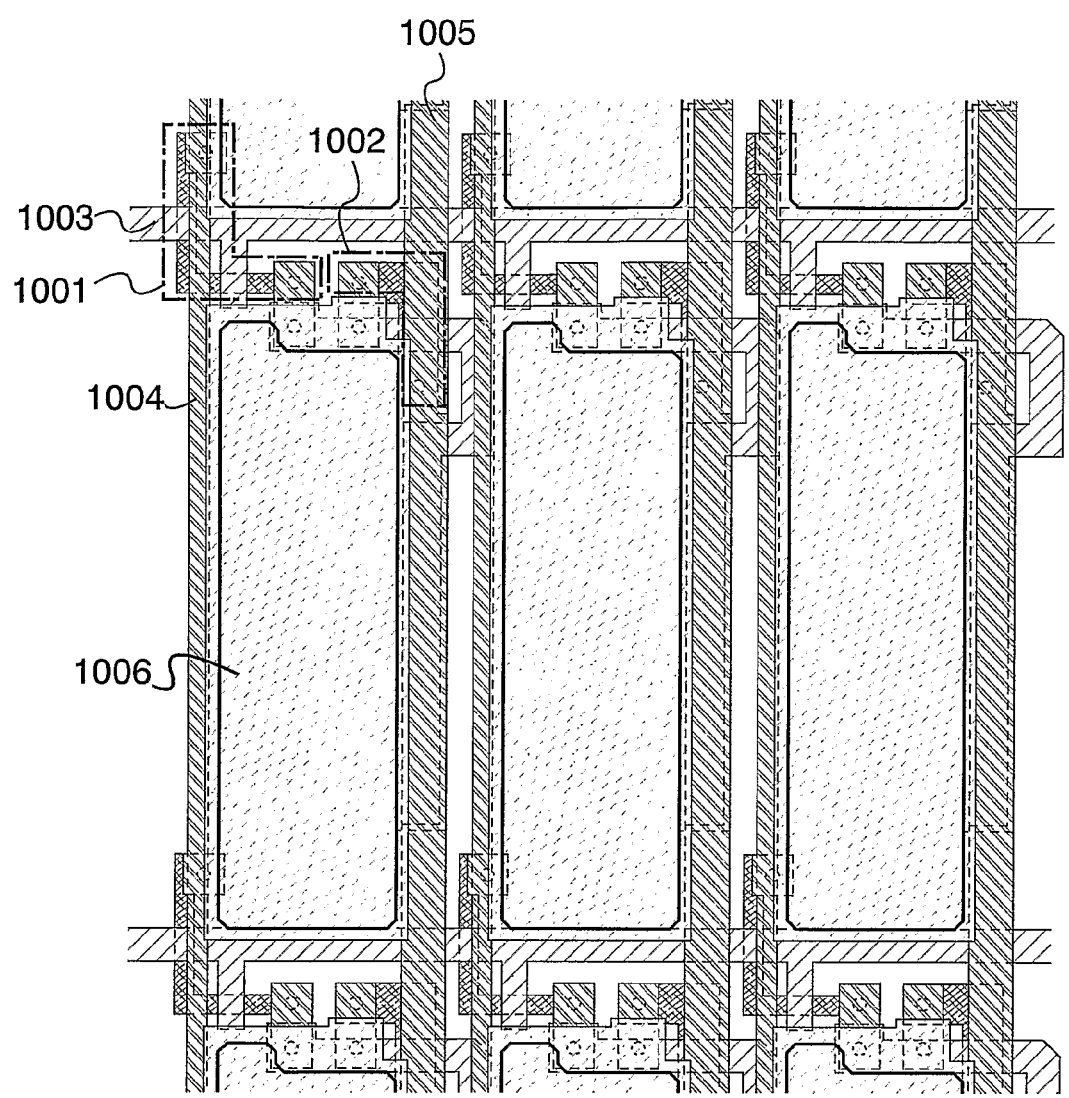
FIG. 5 is a top view explaining a mode of a light-emitting device of the present invention.

The arrangement of the transistors, the light-emitting elements, and the like in the pixel portion is not particularly limited. For example, the arrangement shown in a top view of FIG. 5 can be employed. In FIG. 5, a first electrode of a first transistor 1001 is connected to a source signal line 1004 while a second electrode of the first transistor is connected to a gate electrode of a second transistor 1002. A first electrode of the second transistor is connected to a current supply line 1005 and a second electrode of the second transistor is connected to an electrode 1006 of a light-emitting element. A part of the gate signal line 1003 functions as a gate electrode of the first transistor 1001.

Figure 6:
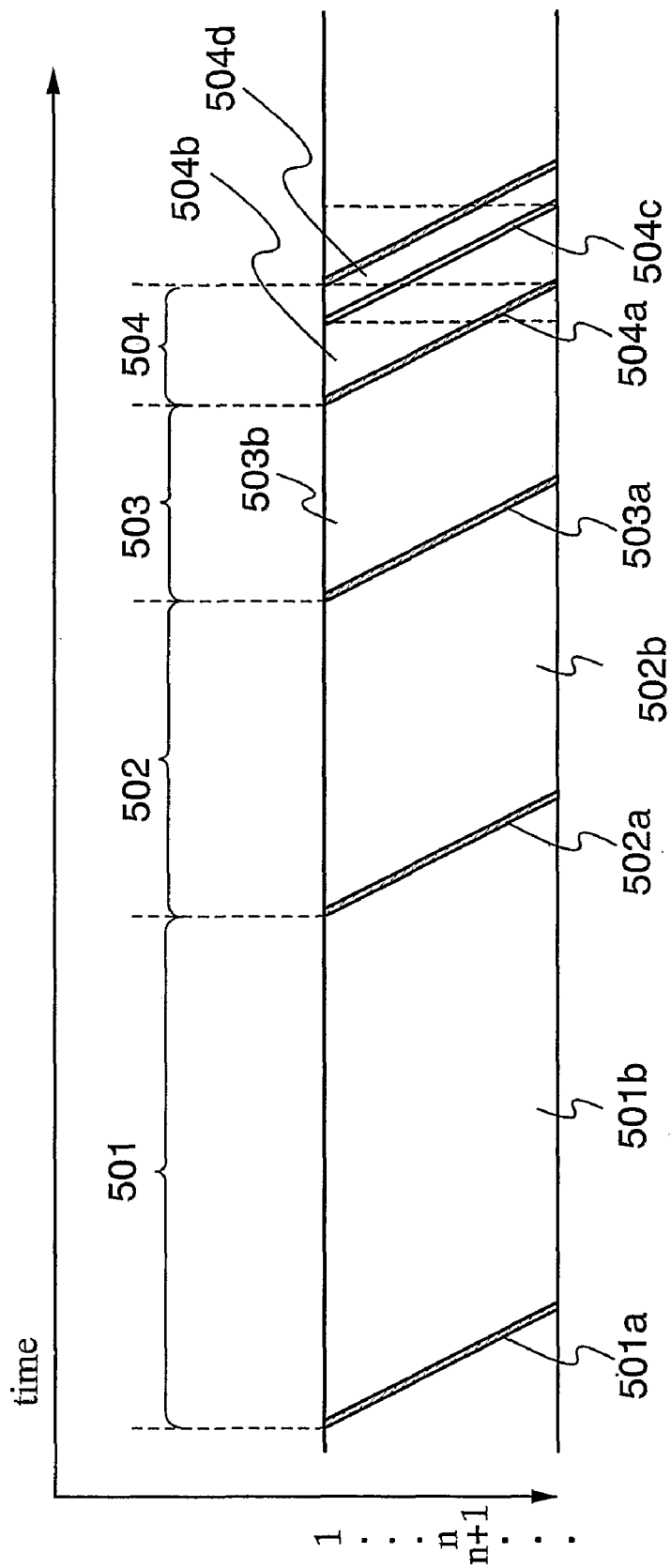
FIG. 6 explains a mode of frame operation of a light-emitting device of the present invention.

Next, the driving method will be described. FIG. 6 is a diagram explaining an operation of a frame with time. In FIG. 6, a horizontal direction indicates time passage while a vertical direction indicates the number of scanning stages of a gate signal line.

When an image is displayed using the light-emitting device of the present invention, a rewriting operation of a screen is carried out repeatedly during a displaying period. The number of the rewriting operations is not particularly limited. However, the rewriting operation is preferably performed at least about 60 times a second such that a person who watches a displayed image does not detect flicker. A period of performing the rewriting operation of one image (one frame) is herein referred to as one frame period.

As shown in FIG. 6, one frame is divided into four sub-frames 501, 502, 503, and 504 including writing periods 501a, 502a, 503a, and 504a and holding periods 501b, 502b, 503b, and 504b. The light-emitting element to which a signal for emitting light has been applied emits light during the holding periods. The length ratio of the holding periods in the respective sub-frames satisfies the first sub-frame 501: the second sub-frame 502: the third sub-frame 503: the fourth sub-frame 504=$2^3:2^2:2^1:2^0$=8:4:2:1. This allows the light-emitting device to exhibit 4-bit gray scale. Further, the number of bits and the number of gray scales are not limited to those shown in this embodiment mode. For instance, one frame may be divided into eight sub-frames so as to achieve 8-bit gray scale.

The operation in one frame will be described. In the sub-frame 501, the writing operation is first performed in first to last rows, sequentially. Therefore, the starting time of the writing period is different for each row. The holding period 501b sequentially starts in the row in which the writing period 501a has been terminated. In the holding period 501b, a light-emitting element to which a signal for emitting light has been applied remains in a light-emitting state. The sub-frame 501 is changed to the next sub-frame 502 sequentially in the row in which the holding period 501b has been terminated. In the sub-frame 502, a writing operation is sequentially performed in the first to last rows in the same manner as the sub-frame 501. The above-mentioned operations are carried out repeatedly up to the holding period 504b of the sub-frame 504. After terminating the operation in the sub-frame 504, an operation in the next frame starts. Accordingly, the sum of the light-emitting periods in the respective sub-frames corresponds to the light-emitting period of each light-emitting element in one frame. By changing the light-emitting period for each light-emitting element and combining such light-emitting elements variously within one pixel, various display colors with different brightness and different chromaticity can be obtained.

When the holding period is intended to be forcibly terminated in the row in which the writing period has already been terminated and the holding period has started prior to terminating the writing operation up to the last row as shown in the sub-frame 504, an erasing period 504c is preferably provided after the holding period 504b so as to stop light emission forcibly. The row where light emission is forcibly stopped does not emit light for a certain period (this period is referred to as a non light-emitting period 504d). Upon terminating the writing period in the last row, a writing period of a next sub-frame (or, a next frame) starts sequentially from a first row. This can prevent the writing period in the sub-frame 504 from superposing with the writing period in the next sub-frame.

Although the sub-frames 501 to 504 are arranged in order from the longer holding period in this embodiment mode, they are not necessarily arranged in this order. For example, the sub-frames may be arranged in order from the shorter holding period. Alternatively, the sub-frames may be arranged in random order. In addition, these sub-frames may further be divided into a plurality of frames. That is, scanning of gate signal lines may be performed several times during a period of applying the same video signals.

The operations of the circuits shown in FIG. 4 in the writing period and the erasing period will be described below.

The operation in the writing period is described first. In the writing period, the gate signal line 911 in the n-th row (n is a natural number) is electrically connected to the writing gate signal line driver circuit 913 via the switch 918. The gate signal line 911 in the n-th row is electrically disconnected to the erasing gate signal line driver circuit 914. The source signal line 912 is electrically connected to the source signal line driver circuit 915 via the switch 920. In this case, a signal is inputted in a gate of the first transistor 901 connected to the gate signal line 911 in the n-th row (n is a natural number), thereby turning on the first transistor 901. At this moment, video signals are simultaneously inputted in the source signal lines in the first to last columns. Further, the video signals inputted from the source signal line 912 in the respective columns are independent from each other. The video signals inputted from the source signal line 912 are inputted in a gate electrode of the second transistor 902 via the first transistor 901 connected to the respective source signal lines. At this time, the amount of current supplied to the light-emitting element 903 from the current supply line 917 is decided by the signals inputted in the second transistor 902. Moreover, whether the light-emitting element 903 emits light or not is decided depending on the amount of current. For instance, when the second transistor 902 is a P-channel type, the light-emitting element 903 emits light by inputting a low level signal in the gate electrode of the second transistor 902. On the other hand, when the second transistor 902 is an N-channel type, the light-emitting element 903 emits light by inputting a high level signal in the gate electrode of the second transistor 902.

Next, the operation in the erasing period is described. In the erasing period, the gate signal line 911 in the n-th row (n is a natural number) is electrically connected to the erasing gate signal line driver circuit 914 via the switch 919. The gate signal line 911 in the n-th row is electrically disconnected to the writing gate signal line deriver circuit 913. The source signal line 912 is electrically connected to the power source 916 via the switch 920. In this case, a signal is inputted in the gate of the first transistor 901 which is connected to the gate signal line 911 in the n-th row, whereby the first transistor 901 is turned on. At this time, erasing signals are simultaneously inputted in the source signal lines of the first to last columns. The erasing signals inputted from the source signal line 912 are inputted in the gate electrode of the second transistor 902 via the first transistor 901 which is connected to each source signal line. A supply of current flowing through the light-emitting element 903 from the current supply line 917 is interrupted by the signals inputted in the second transistor 902. This makes the light-emitting element 903 emit no light forcibly. For example, when the second transistor 902 is a P-channel type, the light-emitting element 903 emits no light by inputting a high level signal in the gate electrode of the second transistor 902. On the other hand, when the second transistor 902 is an N-channel type, the light-emitting element 903 emits no light by inputting a low level signal in the gate electrode of the second transistor 902.

Further, in the erasing period, a signal for erasing is inputted in the n-th row (n is a natural number) by the above-mentioned operation. However, as mentioned above, the n-th row sometimes remains in the erasing period while another row (e.g., an m-th row (m is a natural number)) remains in the writing period. In this case, since a signal for erasing is necessary to be inputted in the n-th row and a signal for writing is necessary to be inputted in the m-th row by utilizing the source signal line in the same column, the after-mentioned operation is preferably carried out.

After the light-emitting element 903 in the n-th row becomes a non-light-emitting state by the above-described operation in the erasing period, the gate signal line 911 and the erasing gate signal line driver circuit 914 are immediately disconnected to each other and the source signal line 912 is connected to the source signal line driver circuit 915 by turning on/off the switch 920. The gate signal line 911 and the writing gate signal line driver circuit 913 are connected to each other while the source signal line and the source signal line driver circuit 915 are connected to each other. A signal is selectively inputted in the signal line in the m-th row from the writing gate signal line driver circuit 913 and the first transistor is turned on while signals for writing are inputted in the source signal lines in the first to last columns from the source signal line driver circuit 915. By inputting these signals, the light-emitting element in the m-th row emits light or no light.

After terminating the writing period in the m-th row as mentioned above, the erasing period immediately starts in the (n+1)-th row. Therefore, the gate signal line 911 and the writing gate signal line driver circuit 913 are disconnected to each other while the source signal line is connected to the power source 916 by turning on/off the switch 920. Moreover, the gate signal line 911 and the writing gate signal line driver circuit 913 are disconnected to each other while the gate signal line 911 is connected to the erasing gate signal line driver circuit 914. A signal is selectively inputted in the gate signal line in the (n+1)-th row from the erasing gate signal line driver circuit 914 to input the signal for turning on the transistor while an erasing signal is inputted therein from the power source 916. Upon terminating the erasing period in the (n+1)-th row in this manner, the writing period immediately starts in the (m+1)-th row. The erasing period and the writing period may be repeated until the erasing period of the last row in the same manner.

Although the writing period in the m-th row is provided between the erasing period in the n-th row and the erasing period of the (n+1)-th row in this embodiment mode, the present invention is not limited thereto. The writing period of the m-th row may be provided between the erasing period in the (n−1)-th row and the erasing period in the n-th row.

Furthermore, in this embodiment mode, when the non-light-emitting period 504*d* is provided like the sub-frame 504, the operation of disconnecting the erasing gate signal line driver circuit 914 from one gate signal line while connecting the writing gate signal line driver circuit 913 to another gate signal line is carried out repeatedly. This operation may be performed in a frame in which a non-light-emitting period is not particularly provided.

Embodiment Mode 5

A circuit having a function of controlling light emission or non light emission of a light-emitting element is not limited to the one shown in FIG. 4. For example, a circuit shown in FIG. 7 may be used.

Figure 7:
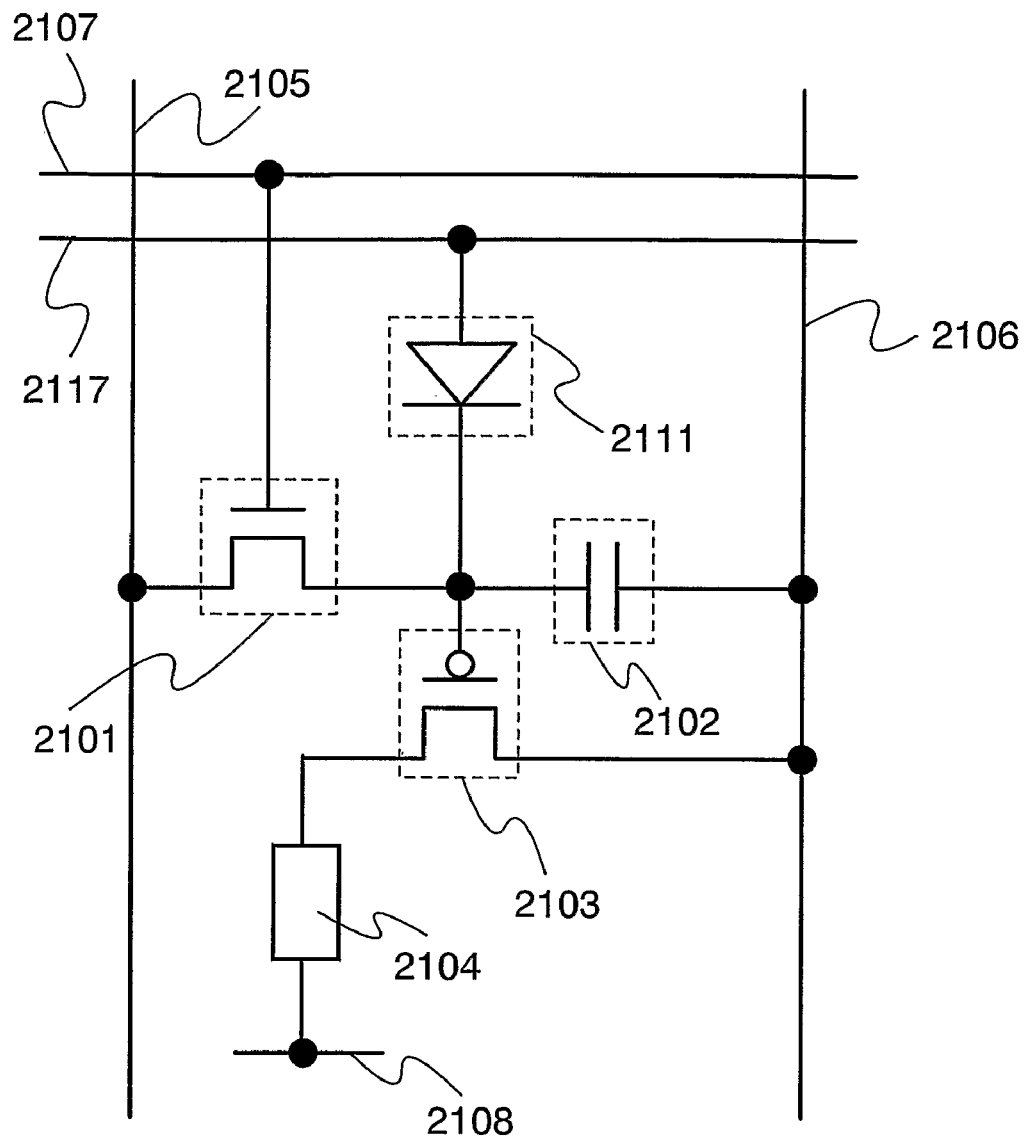
FIG. 7 explains a mode of a circuit included in a light-emitting device of the present invention.

In FIG. 7, a first transistor 2101, a second transistor 2103, an erasing diode 2111, and a light-emitting element 2104 are arranged. A source and a drain of the first transistor 2101 are independently connected to a signal line 2105 and a gate of the second transistor 2103. A gate of the first transistor 2101 is connected to a first gate line 2107. A source and a drain of the second transistor 2103 are independently connected to a power source line 2106 and the light-emitting element 2104. The erasing diode 2111 is connected to both the gate of the second transistor 2103 and a second gate line 2117.

A holding capacitor 2102 has a function of holding a gate potential of the second transistor 2103. Therefore, the holding capacitor 2102 is connected between the gate of the second transistor 2103 and the power source line 2106. However, the position of the holding capacitor 2102 is not limited thereto as long as the holding capacitor can hold the gate potential of the second transistor 2103. If the gate potential of the second transistor 2103 can be held by using a gate capacitor of the second transistor 2103 or the like, the holding capacitor 2102 may be eliminated.

A driving method is as follows. The first gate line 2107 is selected to turn on the first transistor 2101, and then a signal is inputted in the holding capacitor 2102 from the signal line 2105. Then, current of the second transistor 2103 is controlled in accordance with the signal, and current flows to a second power source line 2108 through the light-emitting element 2104 from the first power source line 2106.

In order to erase the signal, the second gate line 2117 is selected (in this case, an electric potential of the second gate line 2117 is increased) and the erasing diode 2111 is turned on to feed current to the gate of the second transistor 2103 from the second gate line 2117. Consequently, the second transistor 2103 becomes an off-state. light-emitting element 2104 from the first power source line 2106. As a result, a Then, current does not flow to the second power source line 2108 through the non-lighting period can be made and the length of a lighting period can be freely controlled.

In order to hold the signal, the second gate line 2117 is not selected (in this case, an electric potential of the second gate line 2117 is decreased). Then, since the erasing diode 2111 is turned off, a gate potential of the second transistor 2103 is held.

Further, the erasing diode 2111 is not particularly limited as long as it is an element having a rectifying property. Either a PN-type diode or a PIN-type diode may be used. Alternatively, either a Schottky diode or a zener diode may be used. Further, diode connection (i.e., a gate and a drain are connected to each other) may be carried out using transistors. Moreover, a P-channel type transistor may be used.

Embodiment Mode 6

An example of a light-emitting device including a light-emitting element of the present invention will be described referring to cross-sectional views of FIGS. 8A to 8C.

Figure 8A:
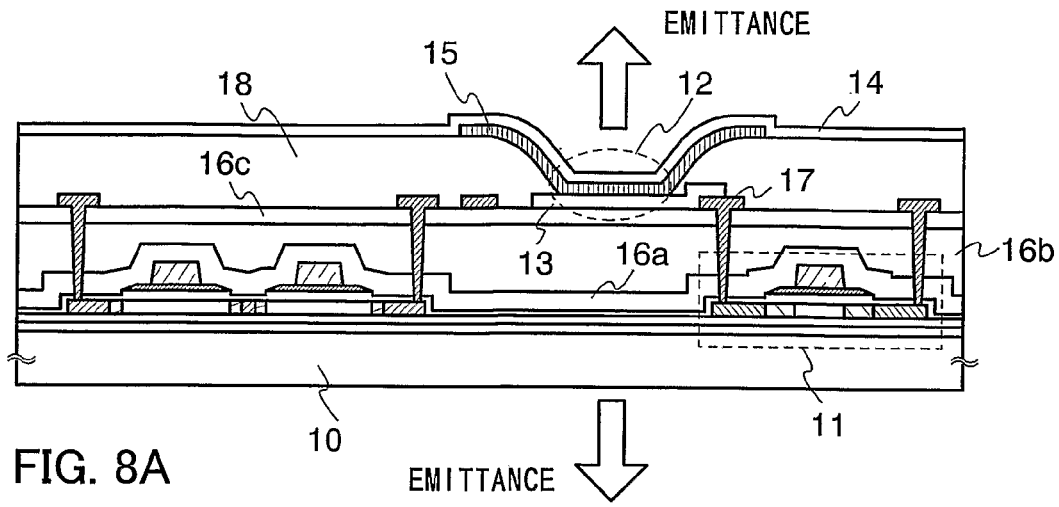
FIGS. 8A to 8C are cross sectional views explaining a mode of a light-emitting device of the present invention.
Figure 8B:
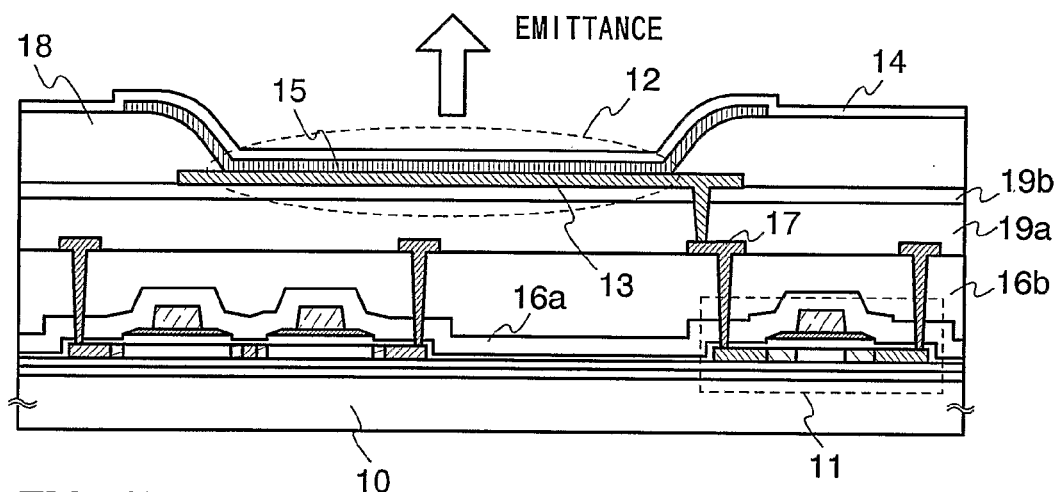
Figure 8C:
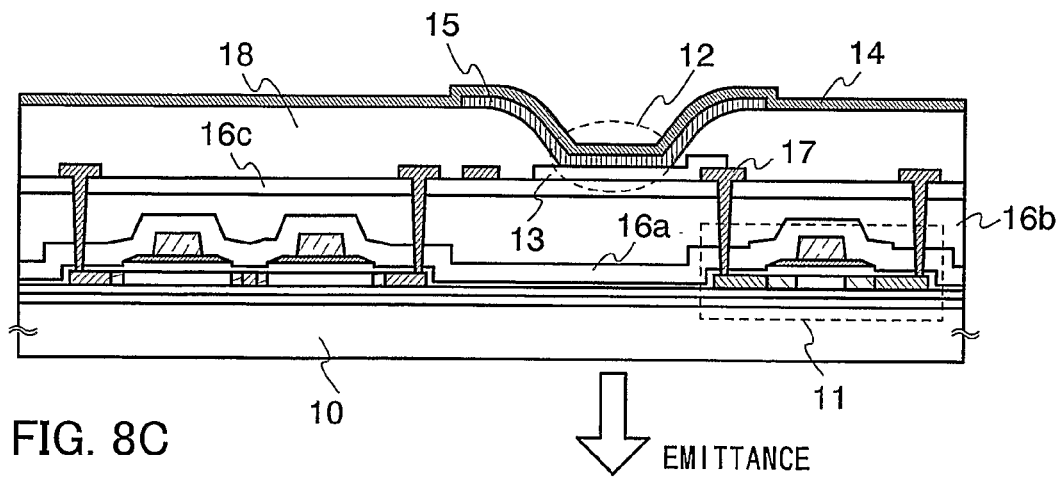

In each of FIGS. 8A to 8C, a transistor 11 provided for driving a light-emitting element 12 of the present invention is surrounded by a dotted line. The light-emitting element 12 of the present invention comprises a light-emitting layer 15 between a first electrode 13 and a second electrode 14. A drain of the transistor 11 and the first electrode 13 are electrically connected to each other via a wiring 17 that passes through first interlayer insulating films 16*a*, 16*b*, and 16*c*. The light-emitting element 12 is isolated from another light-emitting element provided adjacently. A light-emitting device having such a structure is provided over a substrate 10 in this embodiment mode.

The transistor 11 shown in each of FIGS. 8A to 8C is a top-gate type in which a gate electrode is provided over the substrate with a semiconductor layer interposed therebetween. However, the structure of the transistor 11 is not particularly limited thereto, and for example, a bottom-gate type structure may be employed. In the case of the bottom-gate type, either a structure in which a protection film is formed over a semiconductor layer forming a channel (a channel protection type) or a structure in which a semiconductor layer forming a channel is partly concave (a channel-etched type) may be used.

Furthermore, a semiconductor layer included in the transistor 11 may be formed using any one of a crystalline semiconductor, an amorphous semiconductor, a semiamorphous semiconductor, and the like.

The semiamorphous semiconductor has an intermediate structure between an amorphous structure and a crystalline structure (including a single crystal structure and a polycrystalline structure), and a third condition that is stable in terms of free energy. The semiamorphous semiconductor further includes a crystalline region having a short range order along with lattice distortion. A crystal grain with a size of 0.5 to 20 nm is included in at least a part of the semiamorphous semiconductor film. Raman spectrum is shifted lower wavenumbers than 520 cm$^{-1}$. The diffraction peaks of (111) and (220), which are believed to be derived from Si crystal lattice, are observed in the semiamorphous semiconductor by X-ray diffraction. The semiamorphous semiconductor contains hydrogen or halogen of at least 1 atom % or more for terminating dangling bonds. The semiamorphous semiconductor is also referred to as a microcrystalline semiconductor. The semiamorphous semiconductor is formed by glow discharge decomposition of silicide gas (plasma CVD). As for the silicide gas, $SiH_4$, $Si_2H_6$, $SiH_2Cl_2$, $SiHCl_3$, $SiCl_4$, $SiF_4$ or the like can be used. The silicide gas may also be diluted with $H_2$, or a mixture of $H_2$ and one or more of rare gas elements selected from He, Ar, Kr, and Ne. The dilution ratio is set to be in the range of 1:2 to 1:1,000. The pressure is set to be in the range of approximately 0.1 to 133 Pa. The power frequency is set to be 1 to 120 MHz, preferably 13 to 60 MHz. The substrate heating temperature may be set to be 300° C. or less, more preferably 100 to 250° C. With respect to impurity elements contained in the film, each concentration of impurities in atmospheric constituents such as oxygen, nitrogen, and carbon is preferably set to be $1\times10^{20}$/cm$^3$ or less. In particular, the oxygen concentration is set to be $5\times10^{19}$/cm$^3$ or less, preferably $1\times10^{19}$/cm$^3$ or less.

As a specific example of a crystalline semiconductor layer, a semiconductor layer made from single-crystal silicon, polycrystalline silicon, silicon germanium, or the like can be given. The crystalline semiconductor layer may be formed by laser crystallization. For example, the crystalline semiconductor layer may be formed by crystallization with use of a solid phase growth method using nickel or the like.

When a semiconductor layer is formed using an amorphous substance, e.g., amorphous silicon, it is preferable that a light-emitting device have circuits including only N-channel transistors as the transistor 11 and other transistors (transistors included in a circuit for driving a light-emitting element). In another case, a light-emitting device with circuits including either N-channel transistors or P-channel transistors may be employed. Moreover, a light-emitting device with circuits including both, an N-channel transistor and a P-channel transistor may be used.

The first interlayer insulating film 16 may include plural layers (16a, 16b, and 16c) as shown in FIGS. 8A and 8C or a single layer. Specifically, the first interlayer insulating film 16a is formed using an inorganic material such as silicon oxide or silicon nitride. The first interlayer insulating film 16b is formed using acrylic, siloxane (which is a compound that has a skeleton structure formed by a silicon (Si)-oxygen (O) bond and includes hydrogen or an alkyl group such as a methyl group as its substituent), or a substance with a self-planarizing property that can be formed by applying a liquid, such as silicon oxide. Moreover, the first interlayer insulating film 16c is formed with a silicon nitride film containing argon (Ar). The substances constituting the respective layers are not particularly limited thereto. Therefore, substances other than the above-mentioned substances may be employed. Alternatively, a layer formed using a substance other than the above mentioned substances may be provided in combination with the first interlayer insulating films 16a, 16b, and 16c. Accordingly, the first interlayer insulating films 16a, 16b, and 16c may be formed by using both an inorganic material and an organic material or by using either an inorganic material or an organic material.

An edge portion of a partition wall layer 18 preferably has a shape in which the radius of curvature is continuously varied. This partition wall layer 18 is formed by using acrylic, siloxane, resist, silicon oxide, or the like. Further, the partition wall layer 18 may be formed using any one or both of an inorganic film and an organic film.

FIGS. 8A and 8C show the structures in which only the first interlayer insulating films 16a, 16b, and 16c are sandwiched between the transistors 11 and the light-emitting elements 12. However, as shown in FIG. 8B, the first interlayer insulating film 16 (16a and 16b) and a second interlayer insulting film 19 (19a and 19b) may be provided between the transistor 11 and the light-emitting element 12. In the light-emitting device shown in FIG. 8B, the first electrode 13 passes through the second interlayer insulating film 19 to be connected to the wiring 17.

The second interlayer insulating film 19 may include plural layers (19a and 19b) like the first interlayer insulating films 16a, 16b, and 16c or may be a single layer. The second interlayer insulating film 19a is formed using acrylic, siloxane, or a substance with a self-planarizing property that can be formed by applying a liquid, such as silicon oxide. The second interlayer insulating film 19b is formed using a silicon nitride film containing argon (Ar). The substances constituting the respective layers of the second interlayer insulating film are not particularly limited thereto. Therefore, substances other than the above-mentioned substances may be employed. Alternatively, a layer made from a substance other than the above-mentioned substances may be provided in combination with the second interlayer insulating films 19a and 19b. Accordingly, the second interlayer insulating films 19a and 19b may be formed by using both an inorganic material and an organic material or by using either an inorganic material or an organic material.

When the first electrode and the second electrode are both formed using a substance with a light-transmitting property in the light-emitting element 12, light generated in the light-emitting element can be taken out through both the first electrode 13 and the second electrode 14 as shown with white arrows in FIG. 8A. When only the second electrode 14 is formed using a substance with a light-transmitting property, light generated in the light-emitting element 12 can be taken out only through the second electrode 14 as shown with a white arrow of FIG. 8B. In this case, the first electrode 13 is preferably formed using a material with high reflectance, or a film (reflection film) formed using a material with high reflectance is preferably provided under the first electrode 13. When only the first electrode 13 is formed using a substance with a light-transmitting property, light generated in the light-emitting element 12 can be taken out only through the first electrode 13 as shown with a white arrow of FIG. 8C. In this case, the second electrode 14 is preferably formed using a material with high reflectance or a reflection film is preferably provided over the second electrode 14.

Moreover, the light-emitting element 12 may have a structure in which the first electrode 13 serves as an anode and the second electrode 14 serves as a cathode, or a structure in which the first electrode 13 serves as a cathode and the second electrode 14 serves as an anode. In the former case, the transistor 11 is a P-channel transistor. In the latter case, the transistor 11 is an N-channel transistor.

It is to be noted that the light-emitting element of the present invention may be connected to a transistor and be used as a pixel of an active matrix light-emitting device which emits light or no light by receiving a signal from the transistor as described in Embodiment Modes 4 to 6. Alternatively, as shown in FIG. 37, the light-emitting element of the present invention may be used in a passive light-emitting device in which a light-emitting element is driven without particularly providing an element for driving such as a transistor.

Figure 37:
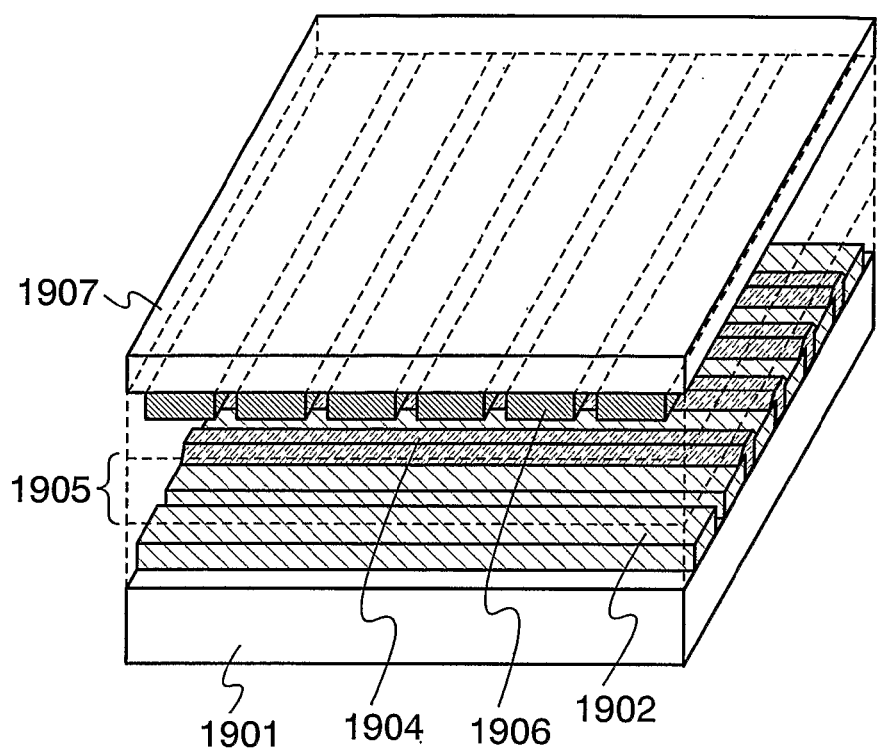
FIG. 37 explains a mode of a light-emitting device of the present invention.

FIG. 37 is a perspective view showing a passive light-emitting device manufactured by applying the present invention. In FIG. 37, an electrode 1902 and an electrode 1906 are provided between a substrate 1901 and a substrate 1907. The electrode 1902 and the electrode 1906 are provided so as to intersect with each other. Moreover, a light-emitting layer 1905 (shown with a dashed line so that the electrode 1902, a partition wall layer 1904, and the like can be seen) is provided between the electrode 1902 and the electrode 1906. Moreover, a hole-transporting layer, an electron-transporting layer, and the like may be provided between the light-emitting layer 1905 and the electrode 1902 or between the light-emitting layer 1905 and the electrode 1906. An end portion of the electrode 1902 is provided with the partition wall layer 1904. In this manner, the end portion of the electrode 1902 is covered with the partition wall layer 1904. Further, even a passive light-emitting device can be driven with lower power consumption by including the light-emitting element of the present invention which operates at lower drive voltage.

Embodiment Mode 7

By mounting a light-emitting device of the present invention, favorable display can be performed for a long time, whereby an electronic appliance with less false recognition of information due to disturbance of a displayed image can be obtained.

Figure 9A:
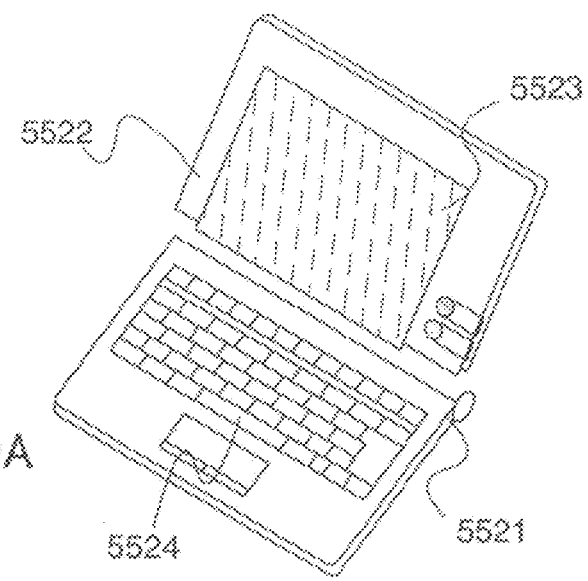
FIGS. 9A to 9C explain electronic appliances in which light-emitting devices of the present invention are used in their display portions.
Figure 9B:
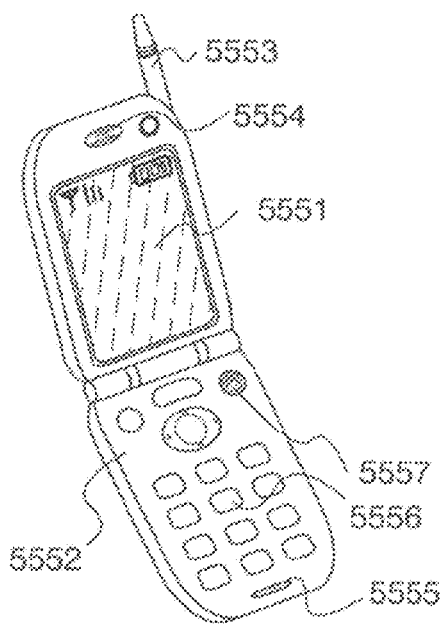
Figure 9C:
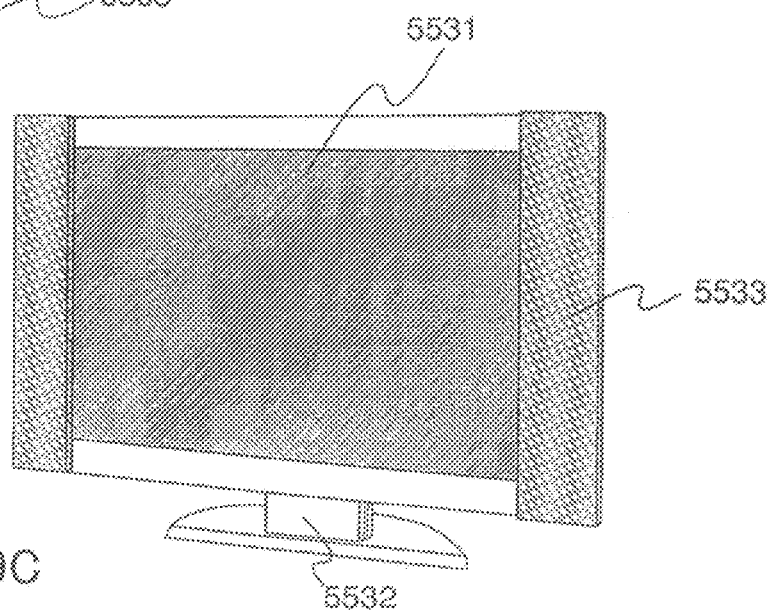

Examples of electronic appliances each having a light-emitting device of the present invention mounted will be shown in FIGS. 9A to 9C.

FIG. 9A shows a laptop personal computer manufactured in accordance with the present invention, comprising a main body 5521, a housing 5522, a display portion 5523, a keyboard 5524, and the like. By incorporating a light-emitting device having a light-emitting element of the present invention into the display portion, the personal computer can be completed.

FIG. 9B shows a portable phone manufactured in accordance with the present invention, comprising a main body 5552, a display portion 5551, an audio output portion 5554, an audio input portion 5555, operation switches 5556 and 5557, an antenna 5553, and the like. By incorporating a light-emitting device having a light-emitting element of the present invention into the display portion, the portable phone can be completed.

FIG. 9C shows a television receiver manufactured in accordance with the present invention, comprising a display portion 5531, a housing 5532, speakers 5533, and the like. By incorporating a light-emitting device having a light-emitting element of the present invention into the display portion, the television receiver can be completed.

As set forth above, a light-emitting device of the present invention is suitable to be used as a display portion of various kinds of electronic appliances.

Although the laptop personal computer, the portable phone, and the television receiver are described in the present embodiment mode, light-emitting devices having light-emitting elements of the present invention may be mounted on a car navigation system, a camera, a lighting apparatus, and the like.

Embodiment 1

Synthetic Example 1

A method for synthesizing an anthracene derivative represented by the structural formula (1) will be described in this synthetic example.

[Step 1]

A method for synthesizing 9,10-bis(4-bromophenyl)-2-tert-butylanthracene will be described.

Under nitrogen gas stream, 1.58 mol/L (13.4 ml) of a butyllithium hexane solution was dripped in 5.0 g of a dried ether solution containing 1,4-dibromobenzene at temperature of −78° C. After dripping the butyllithium hexane solution, the mixture was stirred for one hour at the same temperature. At a temperature of −78° C., a dried ether solution (40 ml) containing 2-tert-butyl anthraquinone (2.80 g) was dripped in the mixture, and then the reaction solution was heated slowly up to room temperature. After the reaction solution was stirred for overnight at the room temperature, water was added thereto, and an organic layer was extracted with ethyl acetate. The organic layer was washed with saturated saline and dried with magnesium sulfate. The dried matter was filtered and concentrated. Then, the residue was purified by silica gel chromatography (developing solvent, hexane-ethyl acetate) to obtain 5.5 g of a compound.

When the thus obtained compound was measured by a nuclear magnetic resonance spectrometry ($^1$H-NMR), it was confirmed that the compound was 9,10-bis(4-bromophenyl)-2-tert-butyl-9,10-dihydroxy-9,10-dihydroanthracene.

The $^1$H-NMR of the compound was shown as follows. The $^1$H-NMR (300 MHz, CDCl$_3$): δ=1.31 (s, 9H), 2.81 (s, 1H), 2.86 (s, 1H), 6.82-6.86 (m, 4H), 7.13-7.16 (m, 4H), 7.36-7.43 (m, 3H), and 7.53-7.70 (m, 4H).

Moreover, a synthetic scheme (b-1) of the 9,10-bis(4-bromophenyl)-2-tert-butyl-9,10-dihydroxy-9,10-dihydroanthracene is shown below.

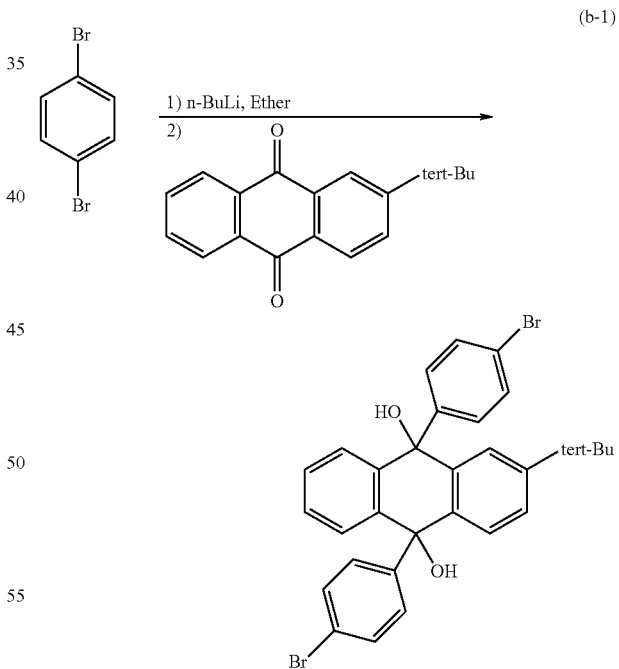

Under atmospheric air, 987 mg (1.55 mmol) of the thus obtained 9,10-bis(4-bromophenyl)-2-tert-butyl-9,10-dihydroxy-9,10-dihydroanthracene, 664 mg (4 mmol) potassium iodide, and 1.48 g (14 mmol) of sodium phosphate acid monohydrate were suspended with 12 ml of glacial acetic acid. The mixture was heated to reflux and stirred for two hours. The reaction mixture was cooled down to the room temperature and the thus generated precipitate was filtered and washed with about 50 ml of methanol to obtain a filtrate. The filtrate was dried to obtain 700 mg of a compound which was a light yellow powder. The yield was 82%. When this compound was measured by a nuclear magnetic resonance spectrometry ($^1$H-NMR, $^{13}$C-NMR), it was confirmed that the compound was 9,10-bis(4-bromophenyl)-2-tert-butylanthracene.

The $^1$H-NMR and the $^{13}$C-NMR of this compound are shown below. $^1$H-NMR (300 MHz, CDCl$_3$): δ=1.28 (s, 9H), 7.25-7.37 (m, 6H), 7.44-7.48 (m, 1H), 7.56-7.65 (m, 4H), and 7.71-7.76 (m, 4H).

$^{13}$C-NMR (74 MHz, CDCl$_3$): δ=30.8, 35.0, 120.8, 121.7, 121.7, 124.9, 125.0, 125.2, 126.4, 126.6, 126.6, 128.3, 129.4, 129.7, 129.9, 131.6, 131.6, 133.0, 133.0, 135.5, 135.7, 138.0, 138.1, and 147.8.

Further, a synthetic scheme (b-2) of 9,10-bis(4-bromophenyl)-2-tert-butylanthracene is shown below.

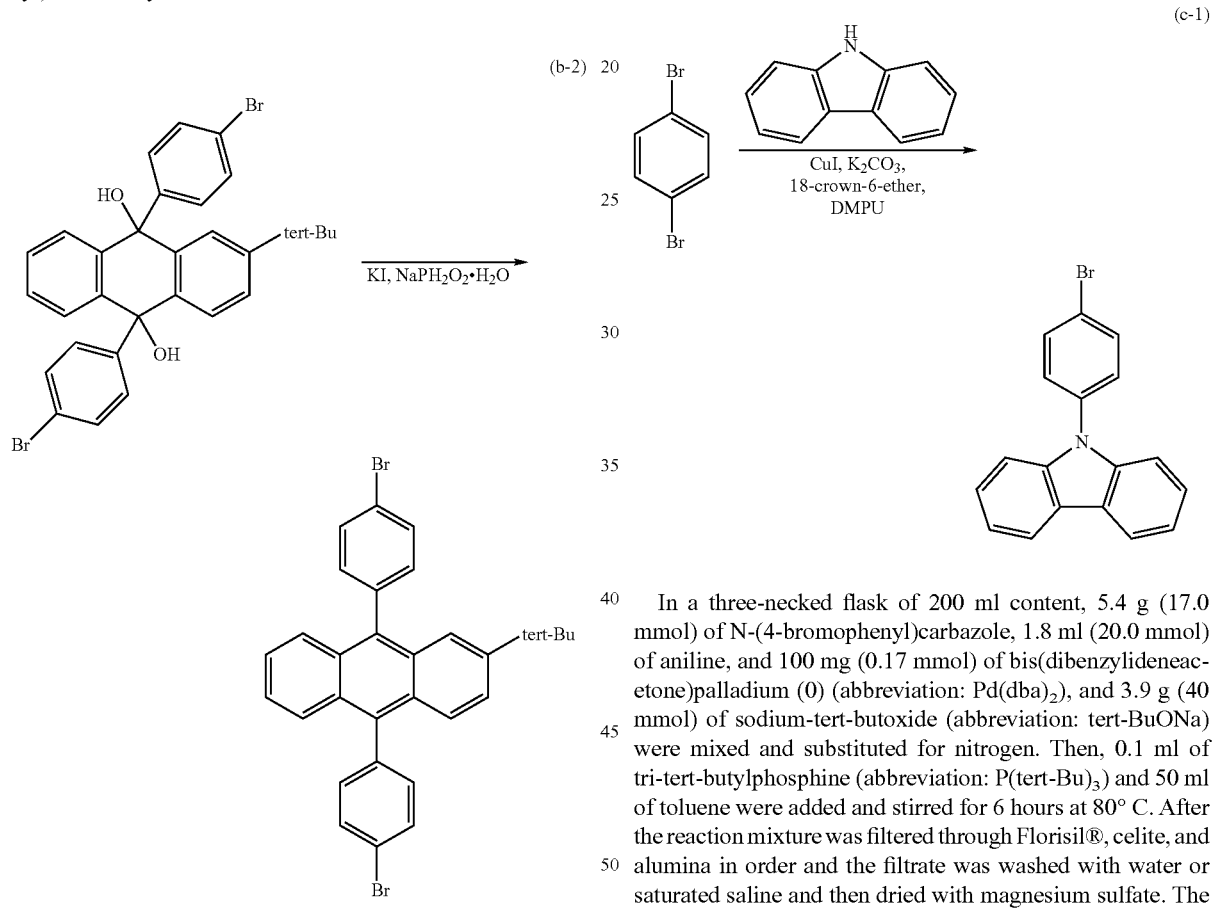

[Step 2]

A method for synthesizing N-(4-bromophenyl)carbazole will be described.

In a three-necked flask of 300 ml content, 56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were mixed and substituted for nitrogen. Then, 8 mL of DMPU was added and stirred for 6 hours at 180° C. After the reaction mixture was cooled down to room temperature, the sediment was removed by suction filtration. The filtrate was washed with diluted hydrochloric acid, a saturated sodium hydrogen carbonate aqueous solution, and saturated saline in this order and then dried with magnesium sulfate. After the drying, the reaction mixture is naturally filtered and concentrated, and then the obtained oil-like substance is purified by silica gel column chromatography (hexane:ethyl acetate=9:1) and recrystallized by a solution including chloroform and hexane. Then, it was confirmed that the intended object, or, a light-brown plate-like crystal is obtained for 20.7 g with a yield of 35%.

The $^1$H-NMR of the compound is shown below.

The $^1$H-NMR (300 MHz, DMSO-d$_6$) δ ppm: 8.14 (d, δ=7.8 Hz, 2H), 7.73 (d, δ=8.7 Hz, 2H), 7.46 (d, δ=8.4 Hz, 2H), and 7.42-7.26 (m, 6H).

Further, a synthetic scheme (c-1) of N-(4-bromophenyl) carbazole is shown below.

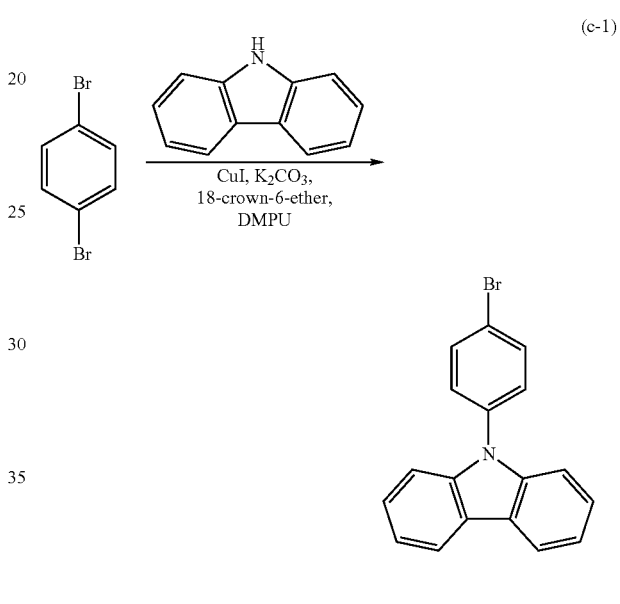

In a three-necked flask of 200 ml content, 5.4 g (17.0 mmol) of N-(4-bromophenyl)carbazole, 1.8 ml (20.0 mmol) of aniline, and 100 mg (0.17 mmol) of bis(dibenzylideneacetone)palladium (0) (abbreviation: Pd(dba)$_2$), and 3.9 g (40 mmol) of sodium-tert-butoxide (abbreviation: tert-BuONa) were mixed and substituted for nitrogen. Then, 0.1 ml of tri-tert-butylphosphine (abbreviation: P(tert-Bu)$_3$) and 50 ml of toluene were added and stirred for 6 hours at 80° C. After the reaction mixture was filtered through Florisil®, celite, and alumina in order and the filtrate was washed with water or saturated saline and then dried with magnesium sulfate. The reaction mixture is naturally filtered and concentrated, and then the obtained oil-like substance is purified by silica gel column chromatography (hexane:ethyl acetate=9:1), whereby the intended object is obtained for 4.1 g with a yield of 73%. By using a nuclear magnetic resonance spectrometry ($^1$H-NMR), it was confirmed that this compound was 9-[4-(N-phenylamino)phenyl]carbazole (abbreviation: YGA).

Figure 13A:
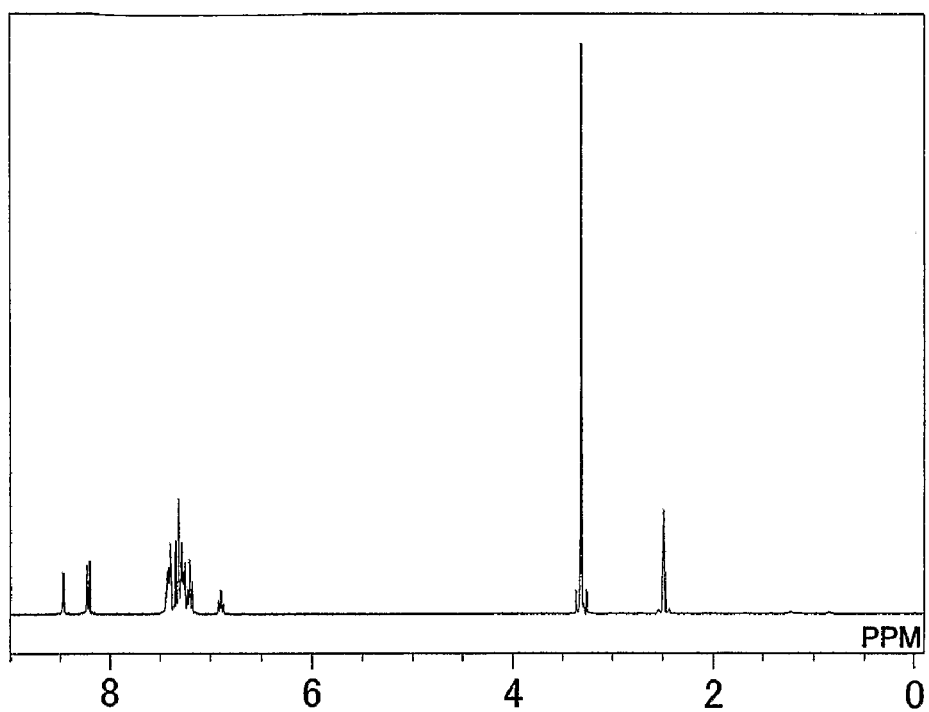
FIGS. 13A and 13B are $^1$H-NMR charts of YGA.
Figure 13B:
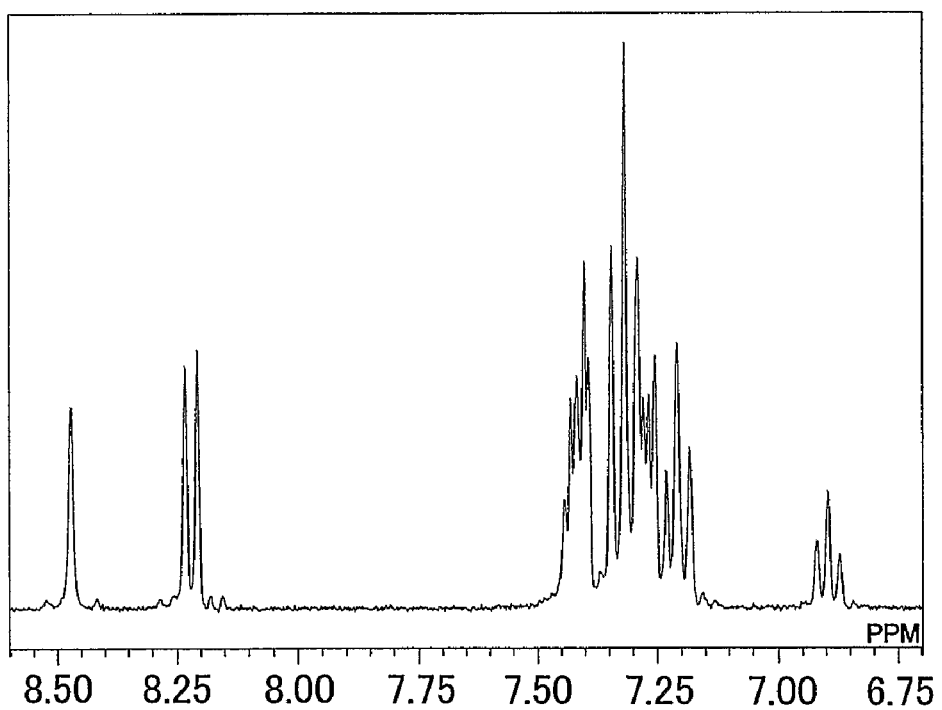

The $^1$H-NMR of the compound is shown below. A $^1$H-NMR chart is also shown in FIGS. 13A and 13B. Further, FIG. 13B is a chart showing an enlarged part in the range of 6.7 ppm to 8.6 ppm of FIG. 13A.

The $^1$H-NMR (300 MHz, DMSO-d$_6$): δ ppm=8.47 (s, 1H), 8.22 (d, δ=7.8 Hz, 2H), 7.44-7.16 (m, 14H), and 6.92-6.87 (m, 1H).

Further, a synthetic scheme (c-2) of 9-[4-(N-phenylamino)phenyl]carbazole is shown below.

Further, a synthetic scheme (d-1) of YGABPA is shown below.

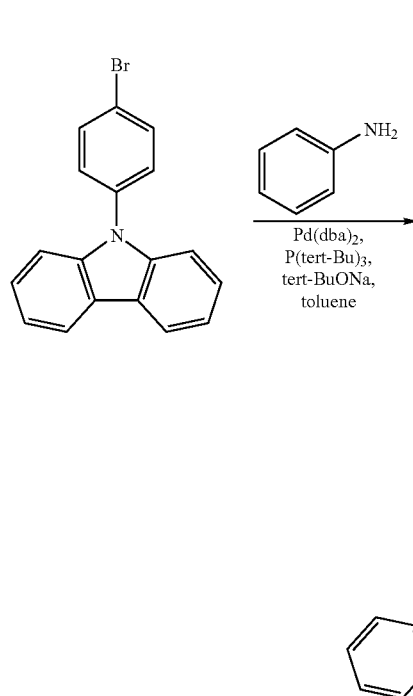

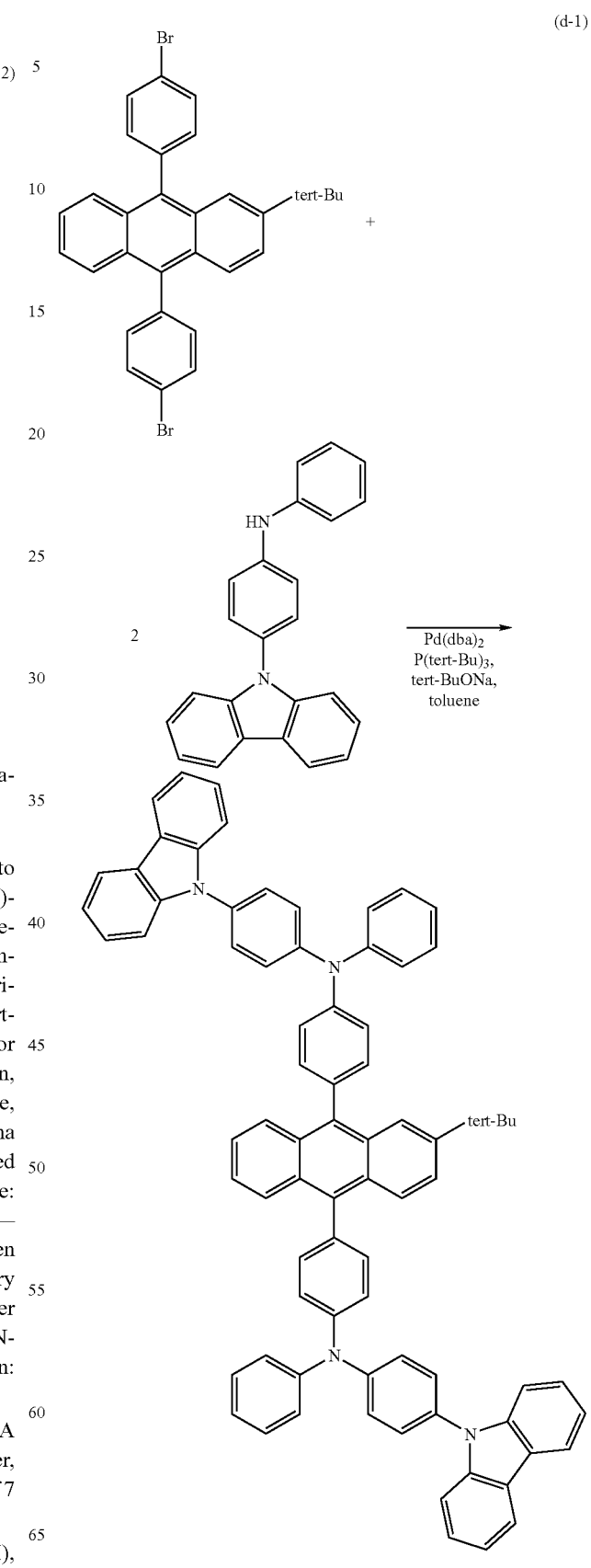

[Step 3]

A method for synthesizing 9,10-bis(4-{N-[4-(9-carbazolyl)phenyl]-N-phenylamino}phenyl)-2-tert-butylanthracene will be described.

Under nitrogen, 10 ml of dehydrated toluene was added to a mixture of 540 mg (1.0 mmol) of 9,10-bis(4-bromophenyl)-2-tert-butylanthracene, 670 mg (2.0 mmol) of 9-[4-(N-phenylamino)phenyl]carbazole, 12 mg (0.02 mmol) of dibenzylidene acetone palladium (0), 110 mg (0.2 mmol) of tri-tert-butylphosphine, and 600 mg (6.2 mmol) of sodium-tert-butoxide. This mixture was heated and stirred at 90° C. for five hours under a nitrogen atmosphere. After the reaction, about 100 ml of toluene was added to the reaction mixture, and then the mixture was filtered through Florisil, alumina and celite in order. The thus obtained filtrate was concentrated and purified by silica gel column chromatography (toluene:hexane=1:1) and then recrystallized by dichloromethane—hexane to obtain 500 mg (the yield: 48%) of a yellow green powder. By using a nuclear magnetic resonance spectrometry ($^1$H-NMR), it was confirmed that this yellow green powder was 9,10-bis(4-{N-[4-(9-carbazolyl)phenyl]-N-phenylamino}phenyl)-2-tert-butylanthracene (abbreviation: YGABPA).

Figure 14A:
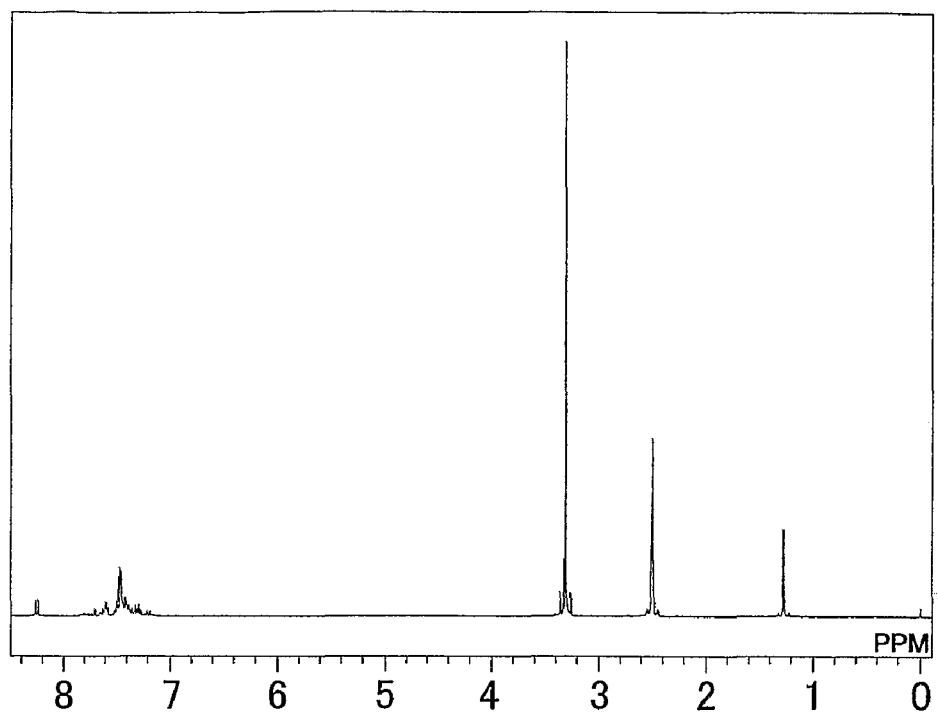
FIGS. 14A and 14B are $^1$H-NMR charts of YGABPA.
Figure 14B:
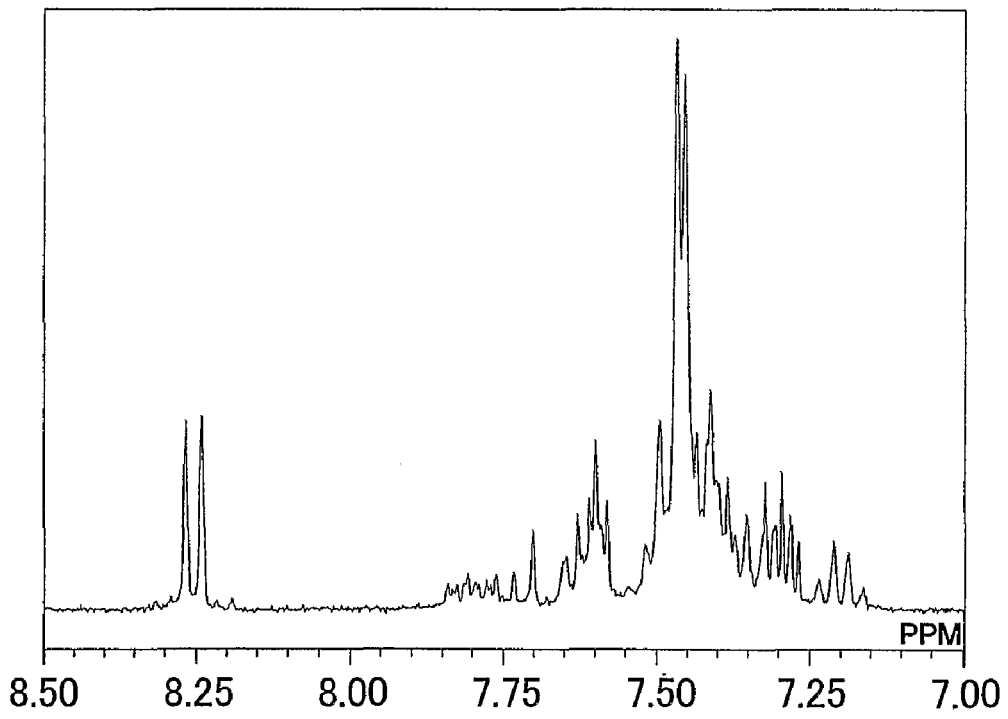

The $^1$H-NMR of the compound is shown below. A $^1$H-NMR chart is also shown in FIGS. 14A and 14B. Further, FIG. 14B is a chart showing an enlarged part in the range of 7 ppm to 8.5 ppm of FIG. 14A.

$^1$H-NMR (300 MHz, DMSO-$d_6$): δ ppm=8.25 (s, 4H), 7.87-7.16 (m, 35H), and 1.28 (s, 9H).

Figure 10:
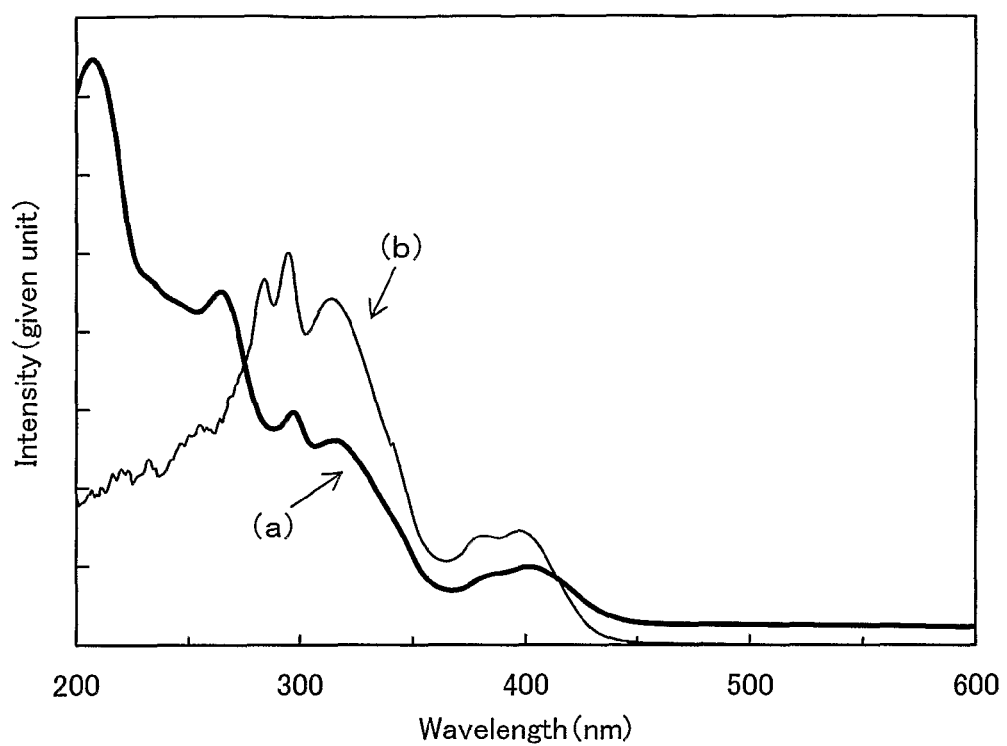
FIG. 10 is a graph showing absorption spectrum of an anthracene derivative of the present invention.
Figure 11:
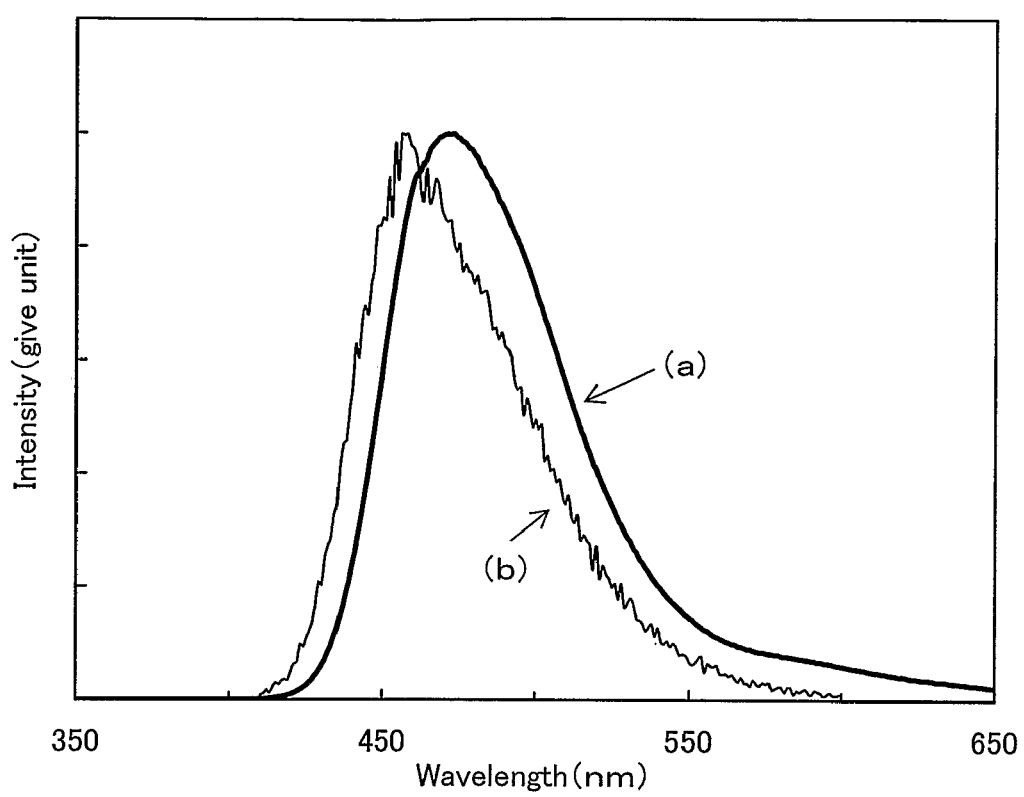
FIG. 11 is a graph showing absorption spectrum of an anthracene derivative of the present invention.

The absorption spectrum of the YGABPA is shown in FIG. 10. In FIG. 10, a horizontal axis represents a wavelength (nm) and a vertical axis represents intensity (absorption intensity). Further, a line (a) indicates the absorption spectrum in a state where the YGABPA is a single film whereas a line (b) indicates the absorption spectrum in a state where the YGABPA is dissolved in a toluene solution. The light emission spectrum of the YGABPA is shown in FIG. 11. In FIG. 11, a horizontal axis represents a wavelength (nm) and a vertical axis represents light emission intensity (given unit). A line (a) indicates the light emission spectrum (an excited wavelength: 358 nm) in a state where the YGABPA is a single film and a line (b) indicates the light emission spectrum (an excited wavelength: 358 nm) in a state where the YGABPA is dissolved in a toluene solution. It is known from FIG. 11 that light emission from the YGABPA has a peak at 474 nm in the single film state and has a peak at 460 nm in the dissolved state in the toluene solution. Moreover, the light emission is recognized as blue light. Thus, it is known that the YGABPA is suitable as a light-emitting substance which emits blue light.

When a film was formed with the thus obtained YGABPA by an evaporation method and the ionizing potential of the YGABPA in the thin film state was measured by using a photoelectron spectrometer (AC-2, manufactured by RIKEN KEIKI CO., LTD.), the ionizing potential was 5.44 eV. The absorption spectrum of the YGABPA in the thin film state was measured by using a UV and visible light spectrophotometer (V-550, manufactured by Japan Spectroscopy Corporation), and a wavelength of an absorption edge at a longer wavelength side of the absorption spectrum was set to be an energy gap (2.86 eV). Under these conditions, when the LUMO level was measured, it was −2.58 eV. It was understood from these results that the YGABPA is a substance having a large energy gap, in other words, large excitation energy, thereby being suitable to be used as a host material.

Further, when a decomposition temperature $T_d$ of the thus obtained YGABPA was measured by a thermo-gravimetric/differential thermal analyzer (TG/DTA 320, manufactured by Seiko Instruments Inc.), the $T_d$ was 500° C. or more, and therefore, it was understood that the YGABPA has an excellent heat resistant property.

In addition, an oxidation reaction characteristic and a reduction reaction characteristic of the YGABPA were measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF) was used as a solvent. Tetra-n-butylammonium perchlorate (n-$Bu_4NClO_4$), which was a supporting electrolyte, was dissolved in the solvent such that the concentration of the tetra-n-butylammonium perchlorate was 100 mmol/L. Moreover, the YGABPA, which was an object to be measured, was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode.

The oxidation reaction characteristic was measured as follows. After the electric potential of the work electrode with respect to the reference electrode was changed from 0.20 V to 0.80 V, a scan for changing the electric potential from 0.80 V to 0.20 V was set as one cycle, and 100 cycles were measured. Further, the scanning speed of the CV measurement was set to be 0.1 V/s.

The reduction reaction characteristic was measured as follows. After the electric potential of the work electrode with respect to the reference electrode was changed from −0.90 V to −2.60 V, a scan for changing the electric potential from −2.60 V to −0.90 V was set as one cycle, and 100 cycles were measured. Further, the scanning speed of the CV measurement was set to be 0.1 V/s.

Figure 12A:
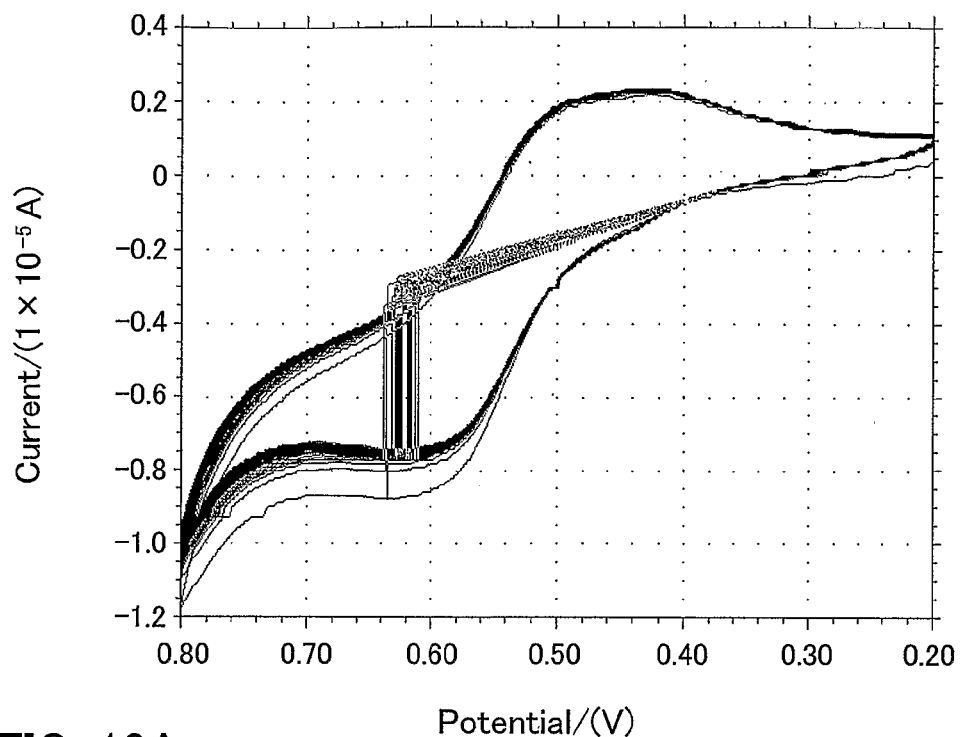
FIGS. 12A and 12B are graphs showing measurement results by cyclic voltammetry (CV) on an anthracene derivative of the present invention.
Figure 12B:
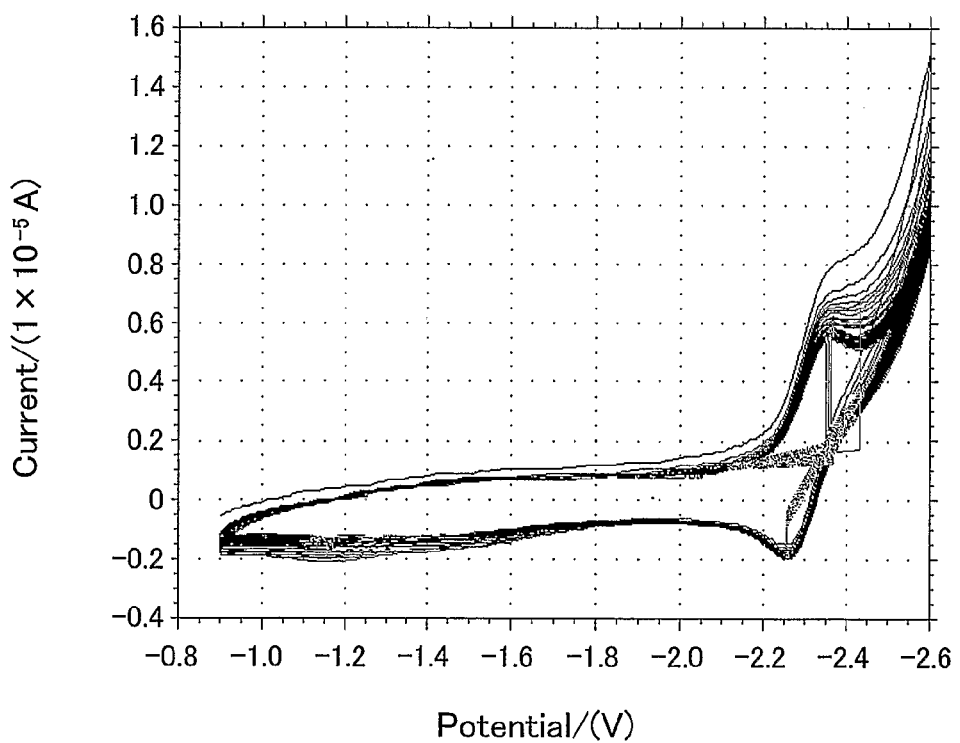

Results of measuring the oxidation reaction characteristic of the YGABPA are shown in FIG. 12A. Moreover, results of measuring the reduction reaction characteristic of the YGABPA are shown in FIG. 12B. In FIGS. 12A and 12B, a horizontal axis represents an electric potential (V) of the work electrode with respect to the reference electrode, while a vertical axis represents the amount of current flowing between the work electrode and the auxiliary electrode ($1 \times 10^{-5}$ A).

It was known from FIG. 12A that an oxidation potential was 0.61 V (vs. Ag/Ag$^+$ electrode). It was known from FIG. 12B that a reduction potential was −2.36 V (vs. Ag/Ag$^+$ electrode). Although the scan was repeated for 100 cycles, a peak position and a peak intensity of a CV curve were hardly changed in each of the oxidation reaction and the reduction reaction. Thus, it was also known that the anthracene derivative is absolutely stable with respect to the repetition of the oxidation reaction and the reduction reaction.

Synthetic Example 2

A method for synthesizing 9,10-bis(4'-{N-[4-(9-carbazolyl)phenyl]-N-phenylamino}biphenyl-4-yl)-2-tert-butylanthracene (abbreviation: YGABBA), which is an anthracene derivative represented by the structural formula (13), will be described in Synthetic Example 2.

[Step 1]

Firstly, a method for synthesizing 9,10-bis(4'-bromobiphenyl-4-yl)-2-tert-butylanthracene will be described.

Specifically, 6.55 g (21.0 mmol) of 4,4'-dibromobiphenyl was poured in a three-neck flask of 500 ml content, and substituted for nitrogen. Next, 200 ml of tetrahydrofuran was added thereto. The mixture was cooled down to −80° C., and then 14.5 ml (22.3 mmol) of n-butyllithium (1.54 mol/L of a hexane solution) was dripped therein and the mixture was stirred for one hour while keeping −80° C. While keeping −80° C., a mixed solution, in which 2.07 g (10.0 mmol) of anthraquinone was suspended in 20 ml of tetrahydrofuran (abbreviation: THF), was dripped in the reaction solution. After the dripping, the mixture was stirred for two hours while the temperature was increased from −80° C. to the room temperature. After the reaction, 110 ml of ethanol was added thereto and the mixture was stirred. Subsequently, the reaction solution was washed with water or saturated saline, and then dried with magnesium sulfate. The reaction mixture was naturally filtered and the filtrate was concentrated to obtain a light yellow solid. Further, a synthetic scheme (e-1) with respect to the above synthesis is shown below.

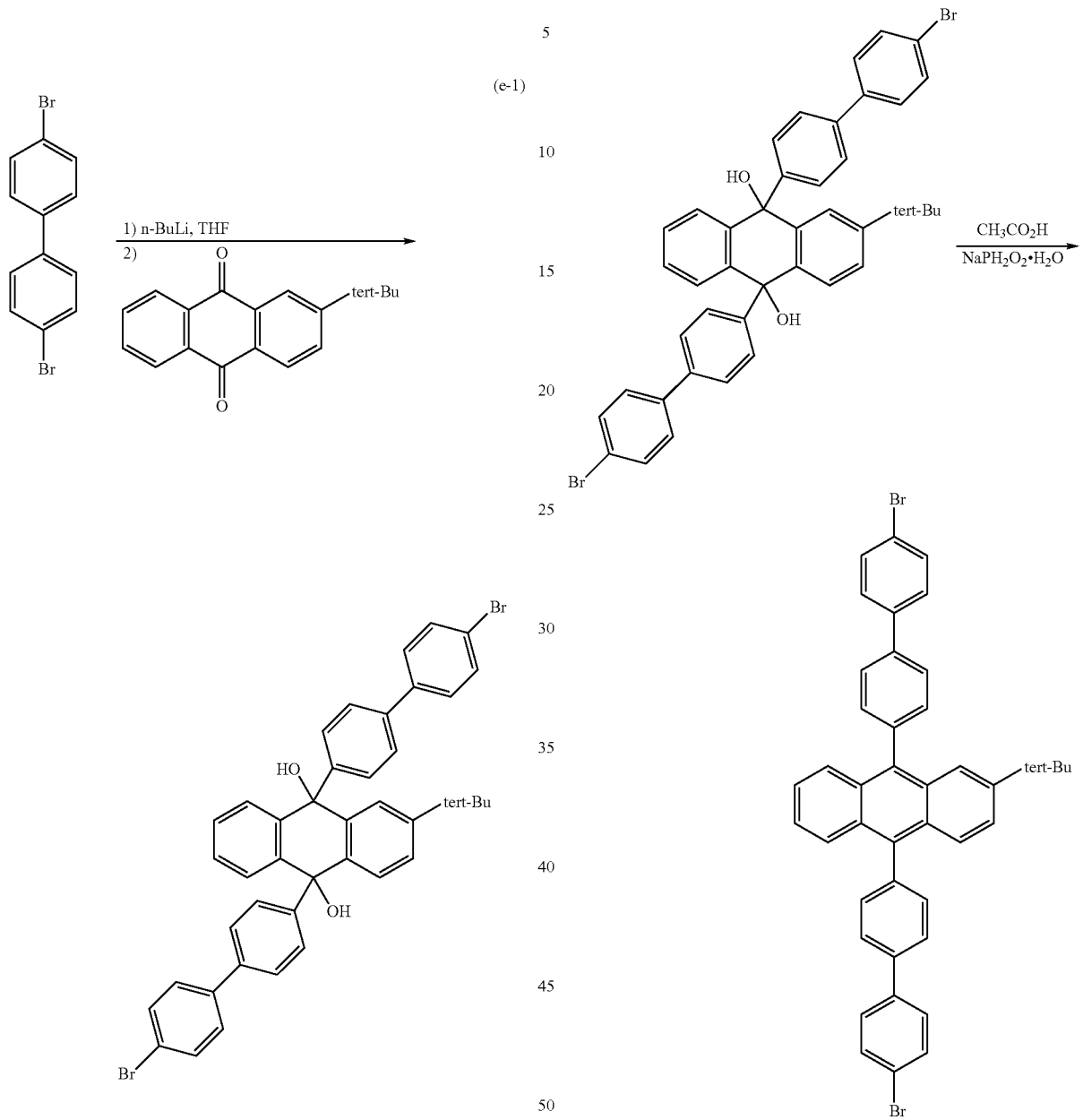

The thus obtained light yellow solid, 6.64 g (40 mmol) of potassium iodide, 12.7 g (120 mmol) of sodium phosphate acid monohydrate, and 120 ml of glacial acetic acid were poured in an eggplant-type flask of 500 ml content. The mixture was refluxed for two hours. After the reaction, the temperature of the mixture temperature, and then, the precipitated solid was collected by suction filtration. The solid was recrystallized by dichloromethane-ethanol to obtain 3.43 g (the yield: 51%) of a light yellow solid of 9,10-bis(4'-bromobiphenyl-4-yl)-2-tert-butylanthracene, which is an object matter. Further, a synthetic scheme (e-2) of 9,10-bis(4'-bromobiphenyl-4-yl)-2-tert-butylanthracene is shown below.

[Step 2]

Next, a method for synthesizing 9,10-bis(4'-{N-[4-(9-carbazolyl)phenyl]-N-phenylamino}biphenyl-4-yl)-2-tert-butylanthracene, which is represented by the structural formula (13), will be described.

Specifically, 151 mg (0.2 mmol) of the 9,10-bis(4'-bromobiphenyl-4-yl)-2-tert-butylanthracene, which was obtained in the Step 1 of this synthetic example, 150 mg (0.44 mmol) of the 9-[4-(N-phenylamino)phenyl]carbazole, which was obtained in the Step 2 of Synthetic Example 1, 10 mg (0.017 mmol) of bis(dibenzylideneacetone)palladium, and 200 mg (2.0 mmol) of sodiumtert-butoxide were poured in a three-necked flask of 100 ml content and substituted for nitrogen.

Then, 0.1 ml of tri-tert-butylphosphine (a 10 wt % hexane solution), and 20 ml of toluene were added to the mixture and refluxed for 8 hours at 110° C. After the reaction, the reaction solution was washed with water and then a water layer was abstracted with toluene. The abstract was washed with saturated saline together with an organic layer of the reaction solution and then dried with magnesium sulfate. After the obtained mixture is naturally filtered, the filtrate is concentrated to obtain a light brown compound. When the light brown compound is purified with silica gel column chromatography (hexane:toluene=1:1), 11 mg (the yield: 3%) of a light yellow solid of 9,10-bis(4'-{N-[4-(9-carbazolyl)phenyl]-N-phenylamino}biphenyl-4-yl)-2-tert-butylanthracene (abbreviation: YGABBA) was obtained, which is a target matter. Further, a synthetic scheme (f-1) of YGABBA is shown below.

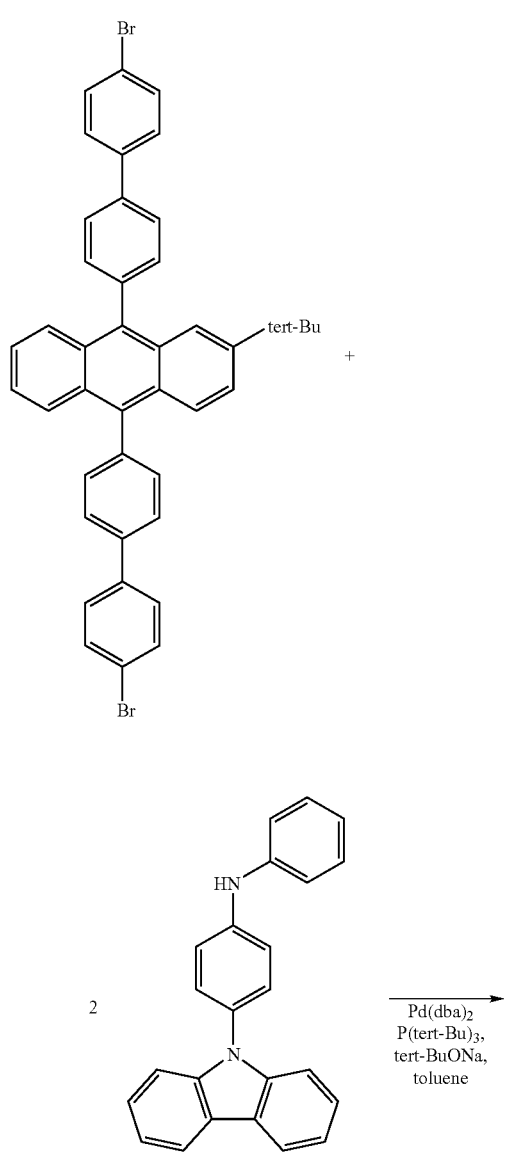

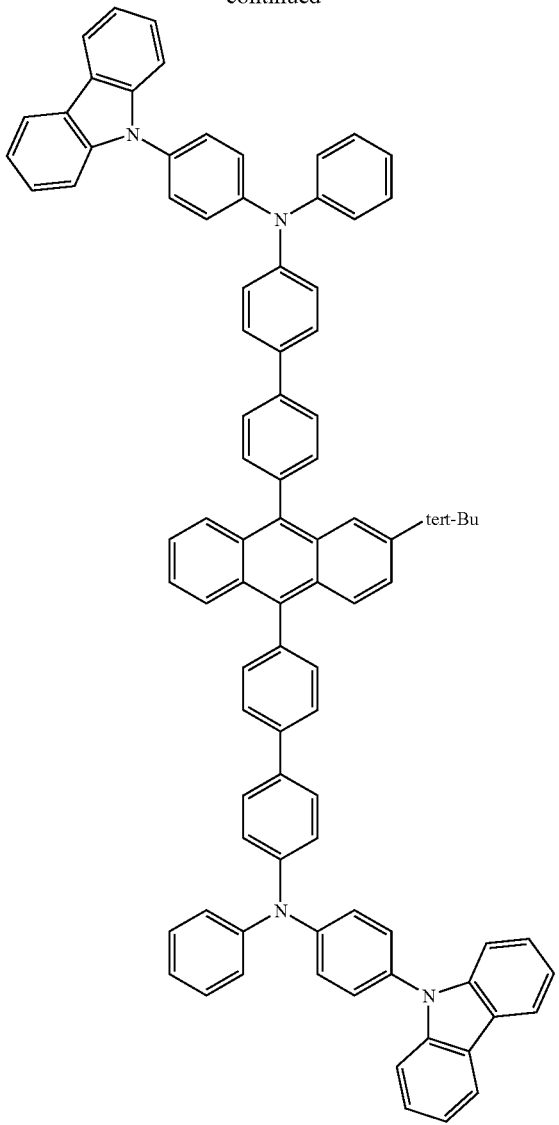

Results of $^1$H-NMR analysis on the light yellow solid (YGABBA) are shown below.

The $^1$H-NMR (300 MHz, CDCl$_3$): δ=8.16 (d, J=7.80 Hz, 4H), 7.89-7.73 (m, 13H), 7.59-7.30 (m, 40H), and 1.28 (s, 9H).

Figure 39:
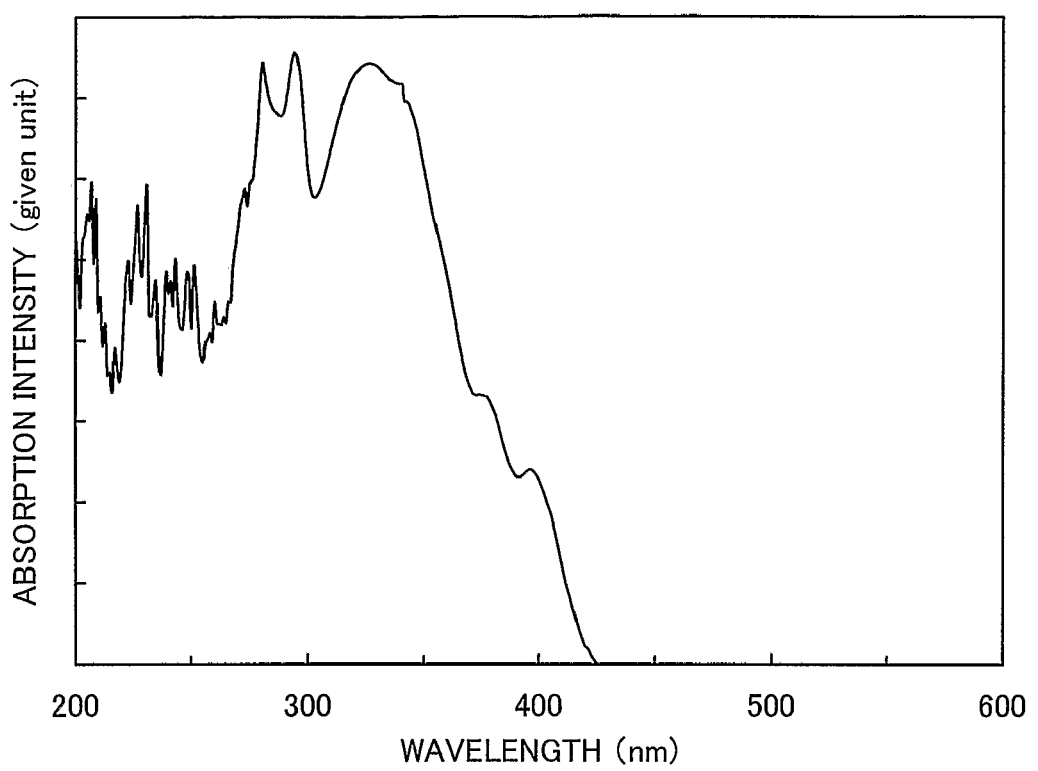
FIG. 39 is a graph showing absorption spectrum of an anthracene derivative of the present invention.
Figure 40:
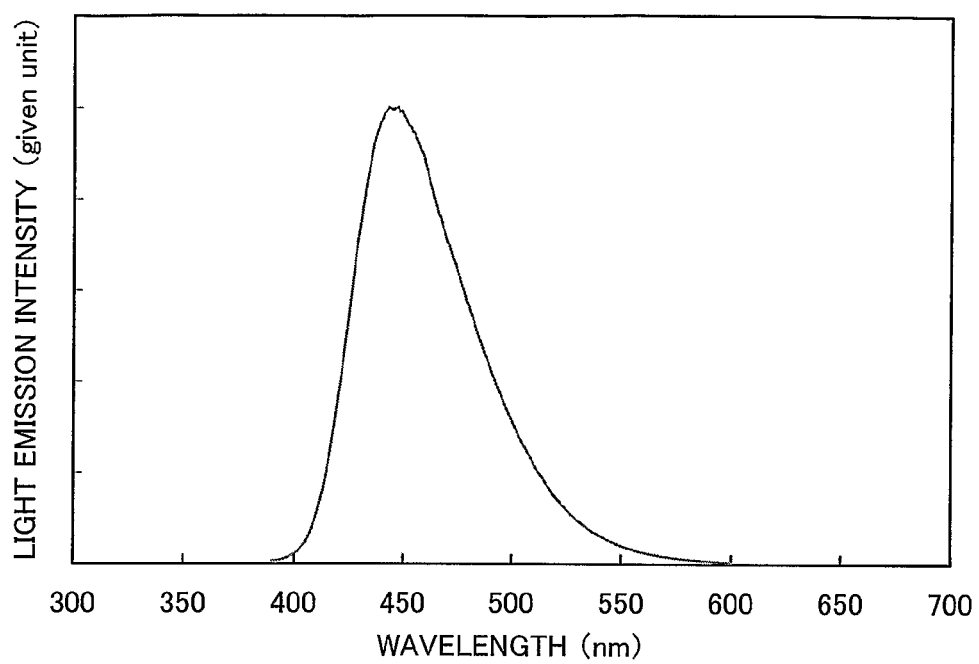
FIG. 40 is a graph showing light emission spectrum of an anthracene derivative of the present invention.

Further, the absorption spectrum of the YGABBA in a toluene solution is shown in FIG. 39. In FIG. 39, a horizontal axis represents a wavelength (nm) and a vertical axis represents absorption intensity (given unit). Moreover, light emission spectrum of the YGABBA in a toluene solution is shown in FIG. 40. In FIG. 40, a horizontal axis represents a wavelength (nm) and a vertical axis represents light emission intensity (given unit). According to FIG. 40, it is known that the light emission of the YGABBA has a peak at 447 nm in the toluene solution, and it was understood that the light emission was blue. Therefore, it was known that the YGABBA is a suitable substance as a light-emitting substance that emits blue light.

Embodiment 2

A method for manufacturing a light-emitting element that uses the YGABPA synthesized in Synthetic Example 1 as a light-emitting substance and an operational characteristic of the light-emitting element will be described in this embodiment.

Figure 15:
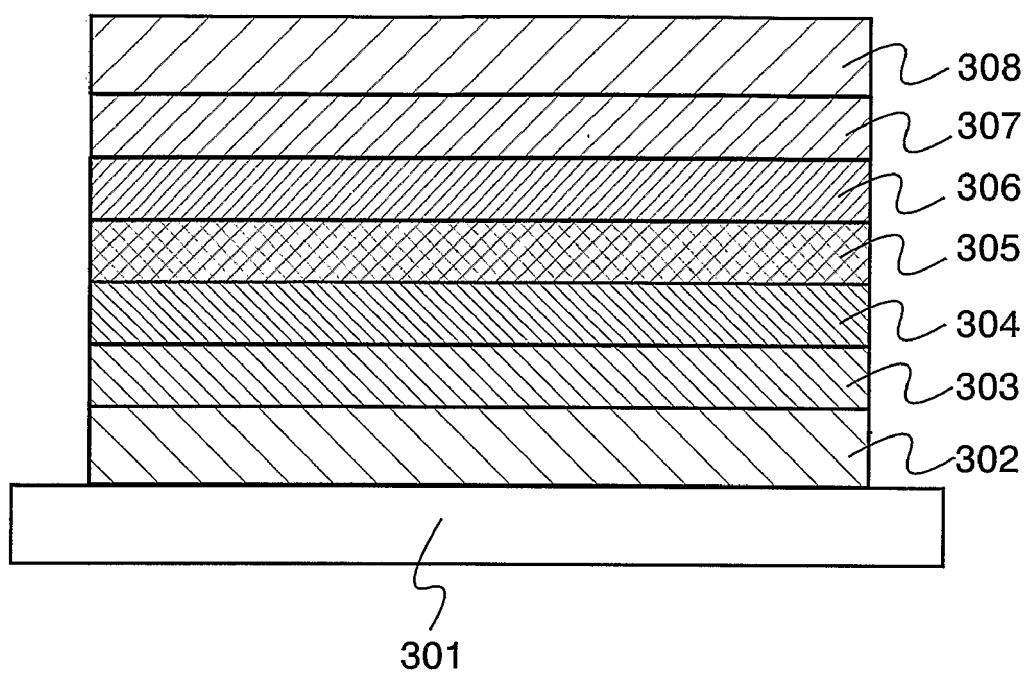
FIG. 15 explains a light-emitting element manufactured in an embodiment.

As shown in FIG. 15, indium tin oxide containing silicon oxide was formed over a glass substrate 301 by a sputtering method to form a first electrode 302. The thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1\times10^{-4}$ Pa. Then, a first layer 303 including copper phthalocyanine was formed over the first electrode 302 by an evaporation method. The thickness of the first layer 303 was set to be 20 nm. The first layer 303 serves as a hole-injecting layer when operating the light-emitting element.

Subsequently, a second layer 304 including NPB was formed over the first layer 303 by an evaporation method. The thickness of the second layer 304 was set to be 40 nm. The second layer 304 serves as a hole-transporting layer when operating the light-emitting element.

A third layer 305 including t-BuDNA and YGABPA was formed over the second layer 304 by a co-evaporation method. The thickness of the third layer 305 was set to be 40 nm. The t-BuDNA-YGABPA mass ratio was adjusted to be 1:0.05. Thus, the YGABPA was in such a state that the YGABPA is dispersed in the layer including t-BuDNA. The third layer 305 serves as a light-emitting layer when operating the light-emitting element. Further, the YGABPA serves as a light-emitting substance.

Next, a fourth layer 306 including $Alq_3$ was formed over the third layer 305 by an evaporation method. The thickness of the fourth layer 306 was set to be 20 nm. The fourth layer 306 serves as an electron-transporting layer when operating the light-emitting element.

A fifth layer 307 including calcium fluoride was formed over the fourth layer 306 by an evaporation method. The thickness of the fifth layer 307 was set to be 1 nm. The fifth layer 307 serves as an electron-injecting layer when operating the light-emitting element.

Next, a second electrode 308 including aluminum was formed over the fifth layer 307. The thickness of the second electrode 308 was set to be 200 nm.

When voltage is applied to the light-emitting element manufactured as above such that an electric potential of the first electrode 302 is higher than that of the second electrode 308, current flows through the light-emitting element. Holes and electrons are recombined at the third layer 305 serving as a light-emitting layer to generate excited energy. The excited YGABPA emits light when returning to a ground state.

This light-emitting element was sealed in a glove box under a nitrogen atmosphere without exposing it to the atmospheric air. Thereafter, an operational characteristic of the light-emitting element was measured. The measurement was carried out at room temperature (under an atmosphere maintaining 25° C.).

Figure 16:
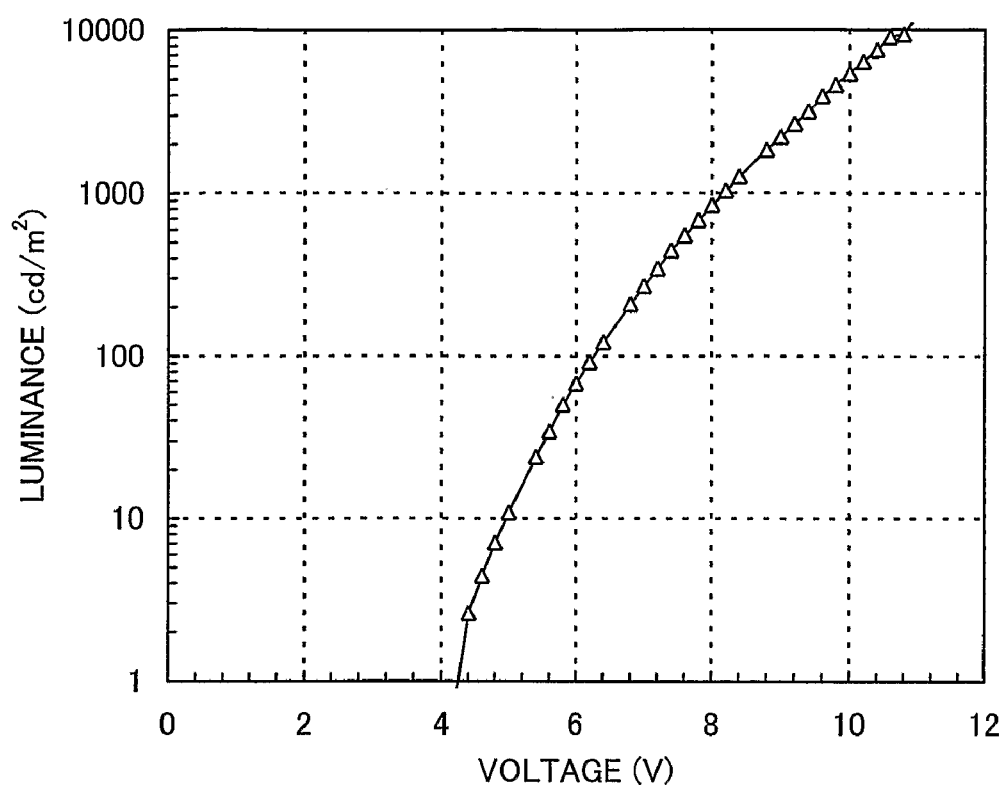
FIG. 16 is a graph showing a luminance-voltage characteristic of a light-emitting element manufactured in Embodiment 2.
Figure 17:
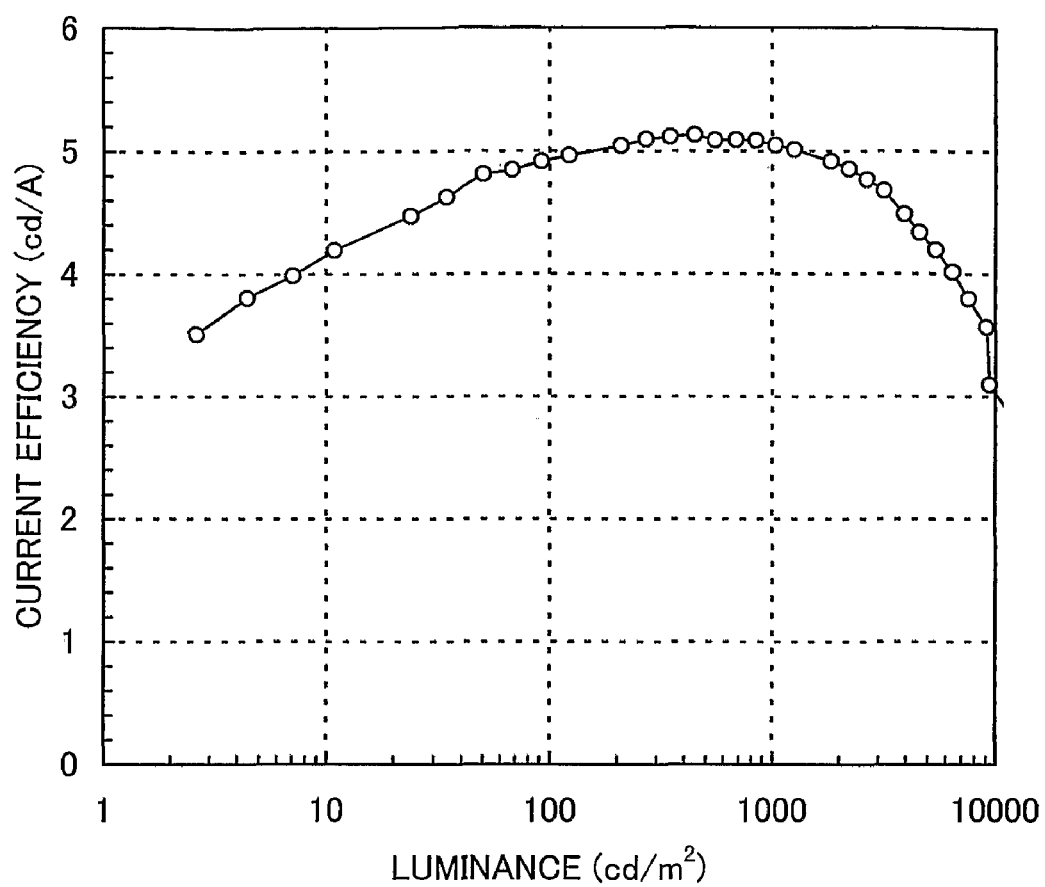
FIG. 17 is a graph showing a luminance-current efficiency characteristic of a light-emitting element manufactured in Embodiment 2.

Measurement results are shown in FIG. 16 and FIG. 17. FIG. 16 shows a measurement result of a voltage-luminance characteristic whereas FIG. 17 shows a measurement result of a luminance-current efficiency characteristic. In FIG. 16, a horizontal axis represents the voltage (V) and a vertical axis represents the luminance ($cd/m^2$). In FIG. 17, a horizontal axis represents the luminance ($cd/m^2$) and a vertical axis represents the current efficiency (cd/A).

Figure 18:
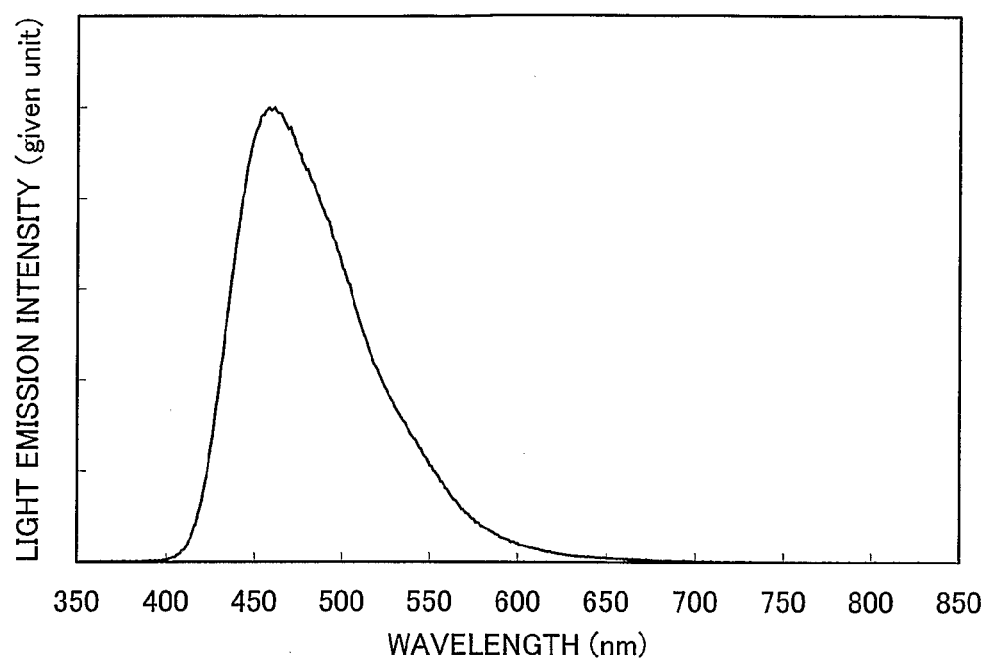
FIG. 18 is a graph showing light emission spectrum of a light-emitting element manufactured in Embodiment 2.

The light emission spectrum of the light-emitting element manufactured in this embodiment is shown in FIG. 18. In FIG. 18, a horizontal axis represents a wavelength (nm) and a vertical axis represents light emission intensity (given unit). According to FIG. 18, it is known that the light-emitting element of the present invention has a peak of light emission spectrum at 462 nm and emits blue light. Moreover, the CIE chromaticity coordinates were x=0.16, y=0.20. Consequently, it was known that the light-emitting element of the present embodiment emits blue light with good color purity.

Embodiment 3

A method for manufacturing a light-emitting element that uses the YGABPA synthesized in Synthetic Example 1 as a light-emitting substance and an operational characteristic of the light-emitting element will be described in this embodiment. Further, a light-emitting element of the present embodiment is similar to the light-emitting element of Embodiment 2 in point of having a structure in which five layers respectively having different substances and layers are stacked between a first electrode and a second electrode. Therefore, the present embodiment will be described with reference to FIG. 15 also used in the description of Embodiment 2.

As shown in FIG. 15, indium tin oxide containing silicon oxide was formed over a glass substrate 301 by a sputtering method to form a first electrode 302. The thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1\times10^{-4}$ Pa. Then, a first layer 303 including copper phthalocyanine was formed over the first electrode 302 by an evaporation method. The thickness of the first layer 303 was set to be 20 nm. The first layer 303 serves as a hole-injecting layer when operating the light-emitting element.

Subsequently, a second layer 304 including 4,4'-bis[N-(4-biphenylyl)-N-phenylamino]biphenyl (abbreviation: BBPB) was formed over the first layer 303 by an evaporation method. The thickness of the second layer 304 was set to be 40 nm. The second layer 304 serves as a hole-transporting layer when operating the light-emitting element.

A third layer 305 including t-BuDNA and YGABPA was formed over the second layer 304 by a co-evaporation method. The thickness of the third layer 305 was set to be 40 nm. The t-BuDNA-YGABPA mass ratio was adjusted to be 1:0.05. Thus, the YGABPA was in such a state that the YGABPA is dispersed in a layer including the t-BuDNA. The third layer 305 serves as a light-emitting layer when operating the light-emitting element. Further, the YGABPA serves as a light-emitting substance.

Next, a fourth layer 306 including $Alq_3$ was formed over the third layer 305 by an evaporation method. The thickness of the fourth layer 306 was set to be 20 nm. The fourth layer 306 serves as an electron-transporting layer when operating the light-emitting element.

A fifth layer 307 including calcium fluoride was formed over the fourth layer 306 by an evaporation method. The thickness of the fifth layer 307 was set to be 1 nm. The fifth layer 307 serves as an electron-injecting layer when operating the light-emitting element.

Next, a second electrode 308 including aluminum was formed over the fifth layer 307. The thickness of the second electrode 308 was set to be 200 nm.

When voltage is applied to the light-emitting element manufactured as above such that an electric potential of the first electrode 302 is higher than that of the second electrode 308, current flows through the light-emitting element. Holes and electrons are recombined at the third layer 305 serving as a light-emitting layer to generate excited energy. The excited YGABPA emits light when returning to a ground state.

This light-emitting element was sealed in a glove box under a nitrogen atmosphere without exposing it to the atmospheric air. Thereafter, an operational characteristic of the light-emitting element was measured. The measurement was carried out at room temperature (under an atmosphere maintaining 25° C.).

Figure 19:
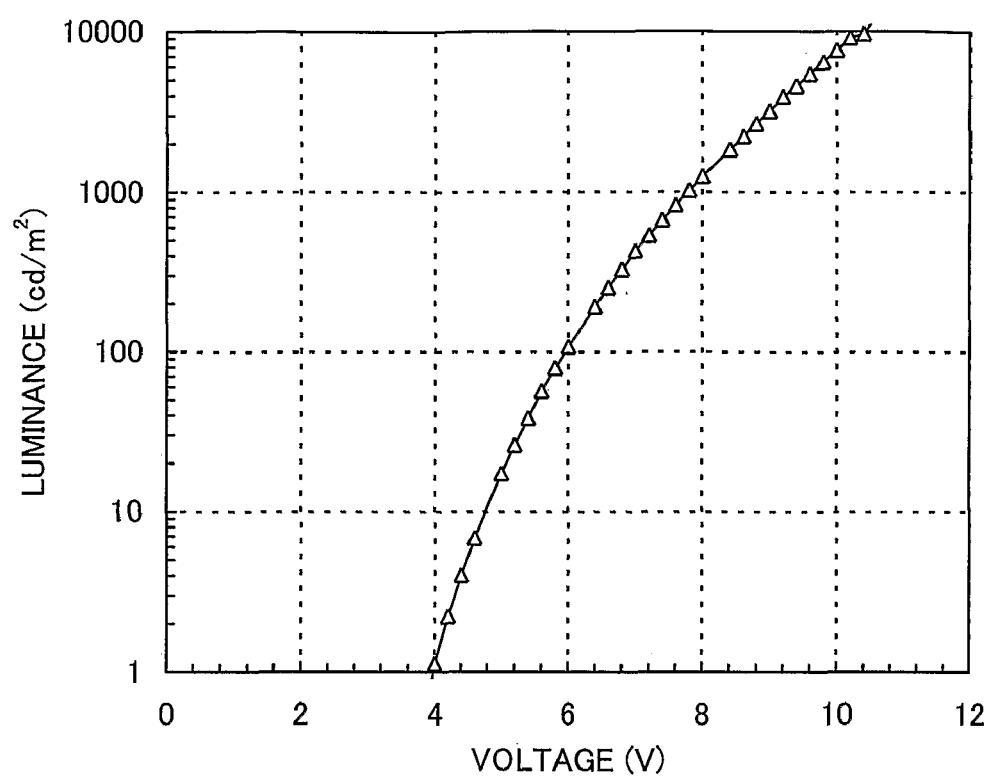
FIG. 19 is a graph showing a luminance-voltage characteristic of a light-emitting element manufactured in Embodiment 3.
Figure 20:
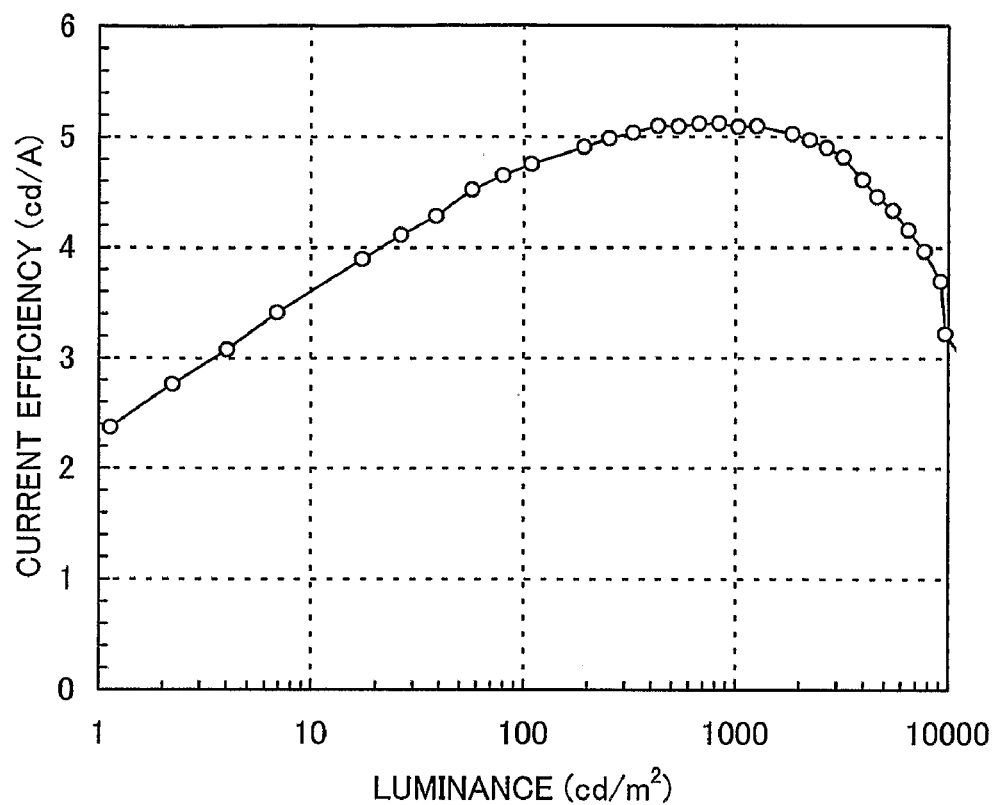
FIG. 20 is a graph showing a luminance-current efficiency characteristic of a light-emitting element manufactured in Embodiment 3.

Measurement results are shown in FIG. 19 and FIG. 20. FIG. 19 shows a measurement result of a voltage-luminance characteristic whereas FIG. 20 shows a measurement result of a luminance-current efficiency characteristic. In FIG. 19, a horizontal axis represents the voltage (V) and a vertical axis represents the luminance (cd/m$^2$). Moreover, in FIG. 20, a horizontal axis represents the luminance (cd/m$^2$) and a vertical axis represents the current efficiency (cd/A).

Figure 21:
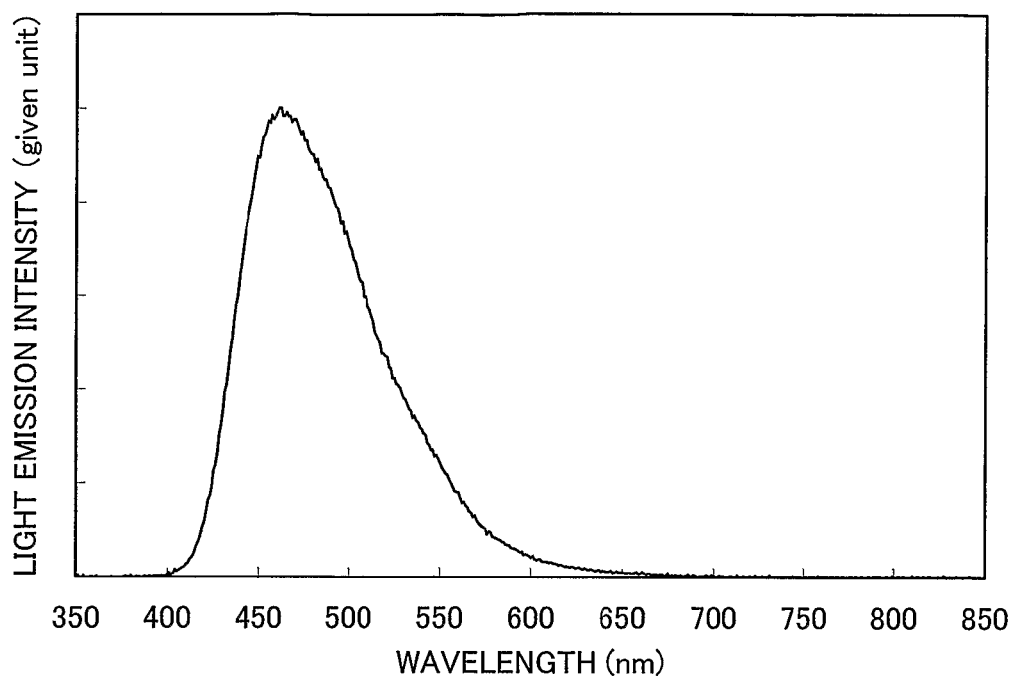
FIG. 21 is a graph showing light emission spectrum of a light-emitting element manufactured in Embodiment 3.

The light emission spectrum of the light-emitting element manufactured in this embodiment is shown in FIG. 21. In FIG. 21, a horizontal axis represents a wavelength (nm) and a vertical axis represents the light intensity (given unit). According to FIG. 21, it is known that the light-emitting element of the present invention has a peak of light emission spectrum at 465 nm, and emits blue light. Moreover, the CIE chromaticity coordinates were x=0.16, y=0.22. Consequently, it is known that the light-emitting element of the present embodiment emits blue light with good color purity.

Embodiment 4

A method for manufacturing a light-emitting element that uses the YGABPA synthesized in Synthetic Example 1 as a light-emitting substance and an operational characteristic of the light-emitting element will be described in this embodiment. Further, a light-emitting element of the present embodiment is similar to the light-emitting element of Embodiment 2 in point of having a structure in which five layers respectively having different substances and thicknesses are stacked between a first electrode and a second electrode. Therefore, the present embodiment will be described with reference to FIG. 15 also used in the description of Embodiment 2.

As shown in FIG. 15, indium tin oxide containing silicon oxide was formed over a glass substrate 301 by a sputtering method to form a first electrode 302. The thickness of the first electrode 302 was set to be 110 nm. The first electrode was formed to have a square shape with a size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to 1×10$^{-4}$ Pa. Then, a first layer 303 including DNTPD was formed over the first electrode 302 by an evaporation method. The thickness of the first layer 303 was set to be 50 nm. The first layer 303 serves as a hole-injecting layer when operating the light-emitting element.

Subsequently, a second layer 304 including NPB was formed over the first layer 303 by an evaporation method. The thickness of the second layer 304 was set to be 10 nm. The second layer 304 serves as a hole-transporting layer when operating the light-emitting element.

A third layer 305 including t-BuDNA and YGABPA was formed over the second layer 304 by a co-evaporation method. The thickness of the third layer 305 was set to be 40 nm. The t-BuDNA-YGABPA mass ratio was adjusted to be 1:0.1. Thus, the YGABPA was in such a state that the YGABPA is dispersed in a layer including the t-BuDNA. The third layer 305 serves as a light-emitting layer when operating the light-emitting element. The YGABPA serves as a light-emitting substance.

Next, a fourth layer 306 including Alq$_3$ was formed over the third layer 305 by an evaporation method. The thickness of the fourth layer 306 was set to be 20 nm. The fourth layer 306 serves as an electron-transporting layer when operating the light-emitting element.

A fifth layer 307 including calcium fluoride was formed over the fourth layer 306 by an evaporation method. The thickness of the fifth layer 307 was set to be 1 nm. The fifth layer 307 serves as an electron-injecting layer when operating the light-emitting element.

Next, a second electrode 308 including aluminum was formed over the fifth layer 307. The thickness of the second electrode 308 was set to be 200 nm.

When voltage is applied to the light-emitting element manufactured as above such that an electric potential of the first electrode 302 is higher than that of the second electrode 308, current flows through the light-emitting element. Holes and electrons are recombined at the third layer 305 serving as a light-emitting layer to generate excited energy. The excited YGABPA emits light when returning to a ground state.

This light-emitting element was sealed in a glove box under a nitrogen atmosphere without exposing it to the atmospheric air. Thereafter, an operational characteristic of the light-emitting element was measured. The measurement was carried out at room temperature (under an atmosphere maintaining 25° C.).

Figure 22:
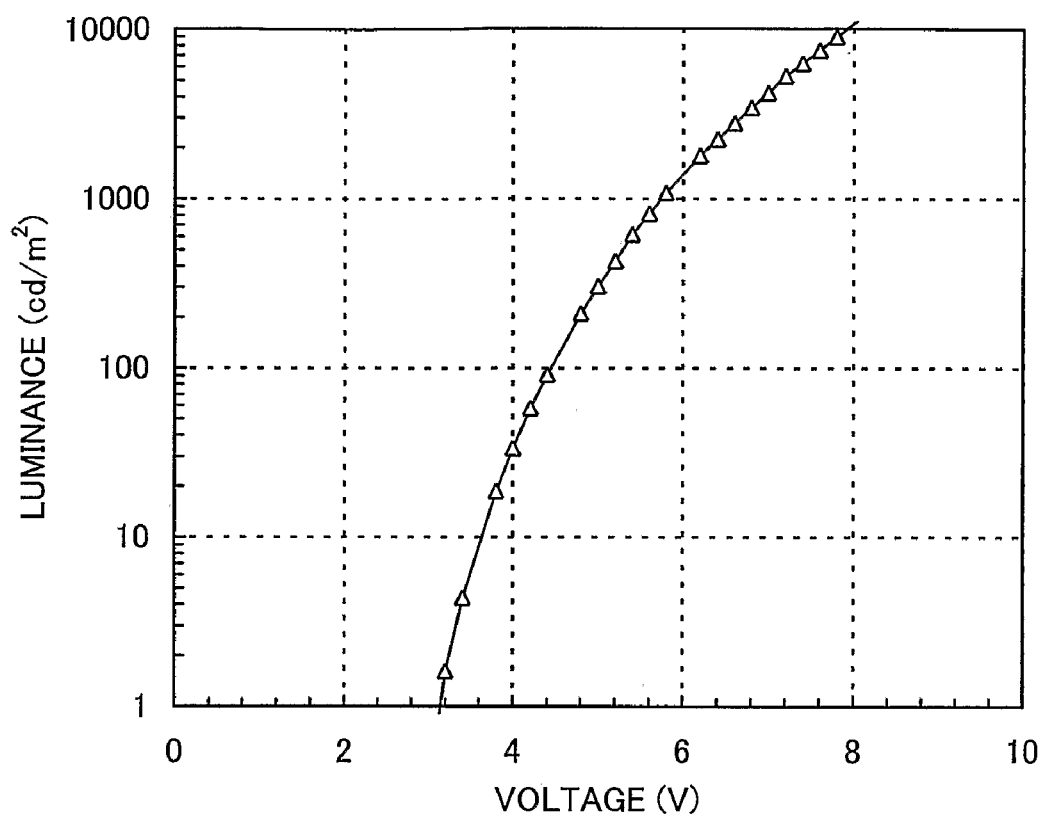
FIG. 22 is a graph showing a luminance-voltage characteristic of a light-emitting element manufactured in Embodiment 4.
Figure 23:
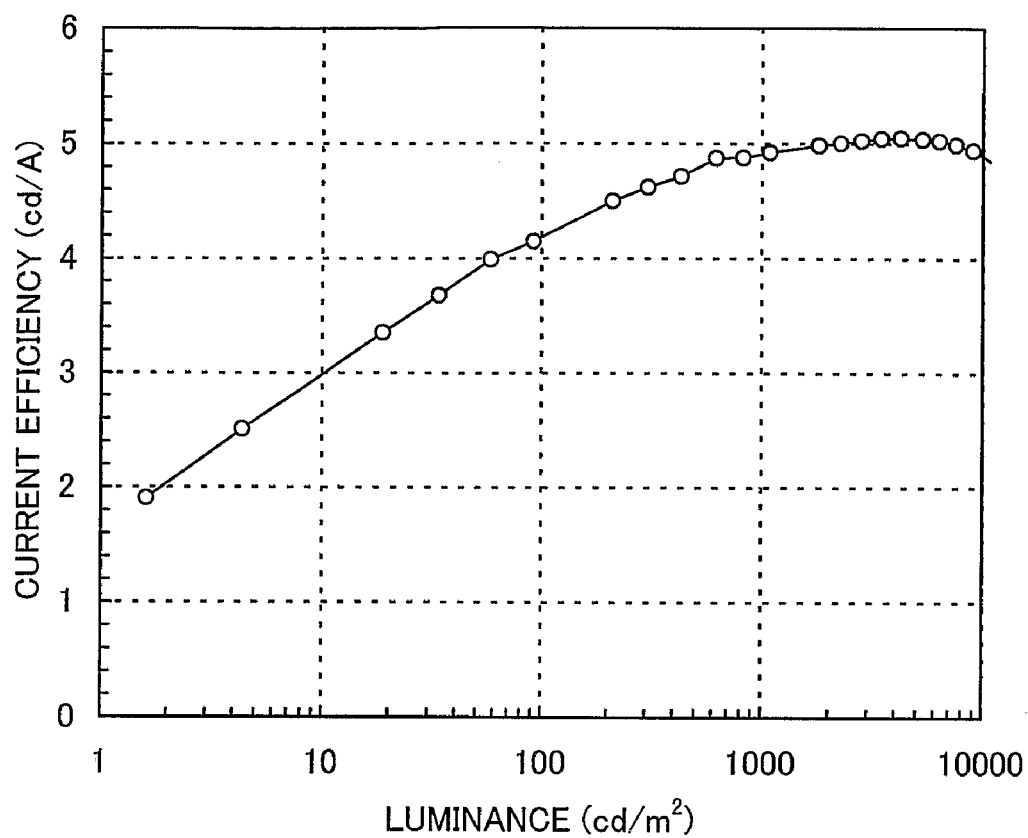
FIG. 23 is a graph showing a luminance-current efficiency characteristic of a light-emitting element manufactured in Embodiment 4.

Measurement results are shown in FIG. 22 and FIG. 23. FIG. 22 shows a measurement result of a voltage-luminance characteristic, whereas FIG. 23 shows a measurement result of a luminance-current efficiency characteristic. In FIG. 22, a horizontal axis represents the voltage (V) and a vertical axis represents the luminance (cd/m$^2$). Moreover, in FIG. 23, a horizontal axis represents the luminance (cd/m$^2$) and a vertical axis represents the current efficiency (cd/A).

Figure 24:
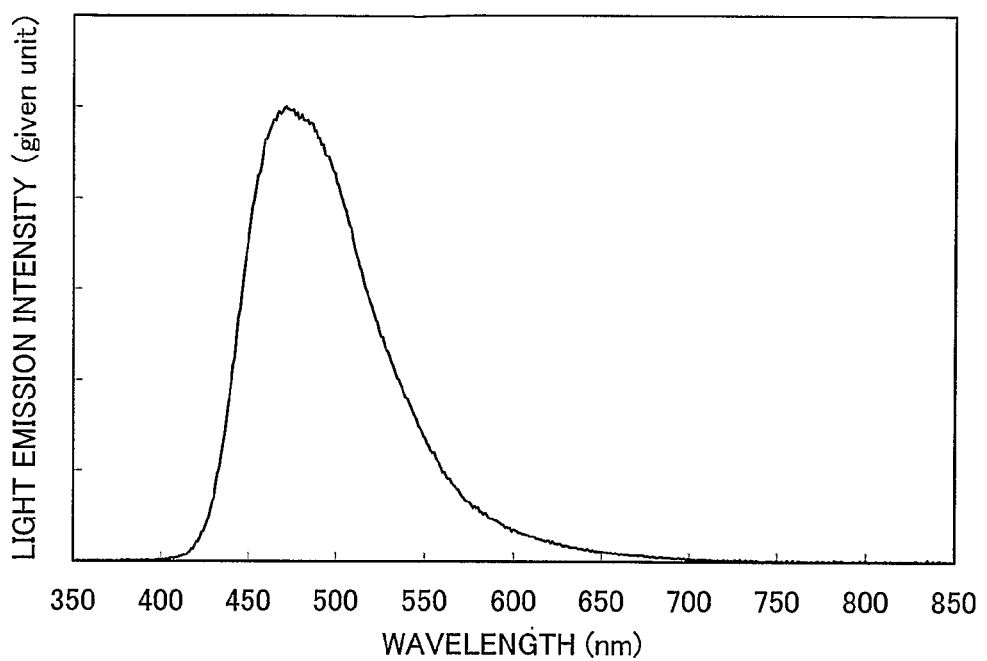
FIG. 24 is a graph showing light emission spectrum of a light-emitting element manufactured in Embodiment 4.

The light emission spectrum of the light-emitting element manufactured in this embodiment is shown in FIG. 24. In FIG. 24, a horizontal axis represents a wavelength (nm) and a vertical axis represents the intensity (given unit). According to FIG. 24, it is known that the light-emitting element of the present invention has a peak of light emission spectrum at 475 nm, and emits blue light. Moreover, the CIE chromaticity coordinates were x=0.18, y=0.27. Consequently, it was known that the light-emitting element of the present embodiment emits blue light with good color purity.

Embodiment 5

A method for manufacturing a light-emitting element that uses the YGABPA synthesized in Synthetic Example 1 as a light-emitting substance and an operational characteristic of the light-emitting element will be described in this embodiment. Further, a light-emitting element of the present embodiment is similar to the light-emitting element of Embodiment 2 in point of having a structure in which five layers respectively having different substances and thicknesses are stacked between a first electrode and a second electrode. Therefore, the present embodiment will be described with reference to FIG. 15 also used in the description of Embodiment 2.

As shown in FIG. 15, indium tin oxide containing silicon oxide was formed over a glass substrate 301 by a sputtering method to form a first electrode 302. The thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1\times10^{-4}$ Pa. Then, a first layer 303 including NPB and molybdenum oxide was formed over the first electrode 302 by an evaporation method. The thickness of the first layer 303 was set to be 50 nm. The NPB-molybdenum oxide mass ratio was adjusted to be 4:2. It is to be noted that molybdenum trioxide was particularly used as the evaporation material. The first layer 303 serves as a hole-generating layer when operating the light-emitting element.

Subsequently, a second layer 304 including NPB was formed over the first layer 303 by an evaporation method. The thickness of the second layer 304 was set to be 10 nm. The second layer 304 serves as a hole-transporting layer when operating the light-emitting element.

A third layer 305 including t-BuDNA and YGABPA was formed over the second layer 304 by a co-evaporation method. The thickness of the third layer 305 was set to be 40 nm. The t-BuDNA-YGABPA mass ratio was adjusted to be 1:0.1. Thus, the YGABPA was in such a state that the YGABPA is dispersed in a layer including the t-BuDNA. The third layer 305 serves as a light-emitting layer when operating the light-emitting element. Further, the YGABPA serves as a light-emitting substance.

Next, a fourth layer 306 including Alq$_3$ was formed over the third layer 305 by an evaporation method. The thickness of the fourth layer 306 was set to be 20 nm. The fourth layer 306 serves as an electron-transporting layer when operating the light-emitting element.

A fifth layer 307 including calcium fluoride was formed over the fourth layer 306 by an evaporation method. The thickness of the fifth layer 307 was set to be 1 nm. The fifth layer 307 serves as an electron-injecting layer when operating the light-emitting element.

Next, a second electrode 308 including aluminum was formed over the fifth layer 307. The thickness of the second electrode 308 was set to be 200 nm.

When voltage is applied to the light-emitting element manufactured as above such that an electric potential of the first electrode 302 is higher than that of the second electrode 308, current flows through the light-emitting element. Holes and electrons are recombined at the third layer 305 serving as a light-emitting layer to generate excited energy. The excited YGABPA emits light when returning to a ground state.

This light-emitting element was sealed in a glove box under a nitrogen atmosphere without exposing it to the atmospheric air. Thereafter, an operational characteristic of the light-emitting element was measured. The measurement was carried out at room temperature (under an atmosphere maintaining 25° C.).

Figure 25:
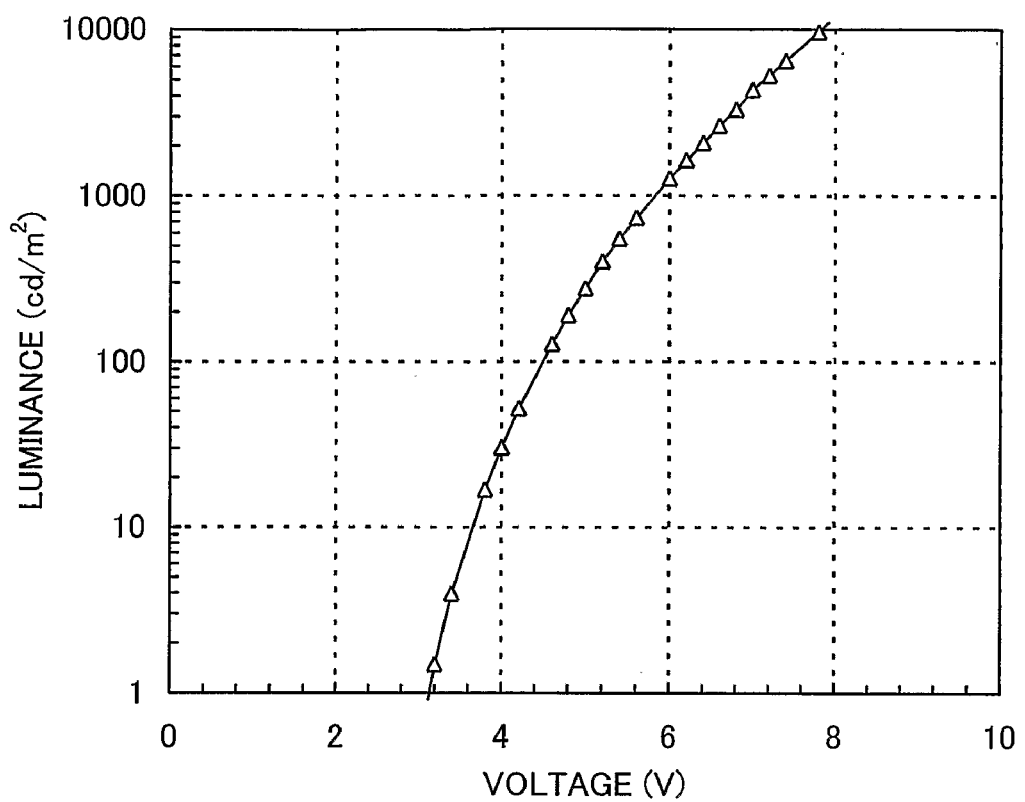
FIG. 25 is a graph showing a luminance-voltage characteristic of a light-emitting element manufactured in Embodiment 5.
Figure 26:
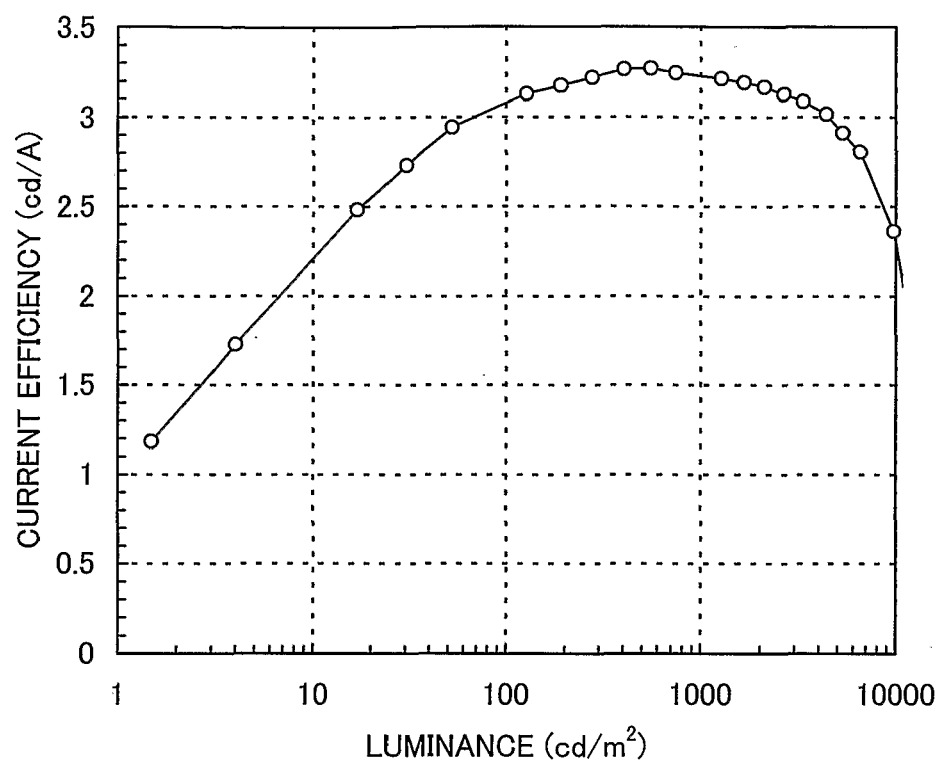
FIG. 26 is a graph showing a luminance-current efficiency characteristic of a light-emitting element manufactured in Embodiment 5.

Measurement results are shown in FIG. 25 and FIG. 26. FIG. 25 shows a measurement result of a voltage-luminance characteristic whereas FIG. 26 shows a measurement result of a luminance-current efficiency characteristic. In FIG. 25, a horizontal axis represents the voltage (V) and a vertical axis represents the luminance (cd/m$^2$). Moreover, in FIG. 26, a horizontal axis represents the luminance (cd/m$^2$) and a vertical axis represents the current efficiency (cd/A).

Figure 27:
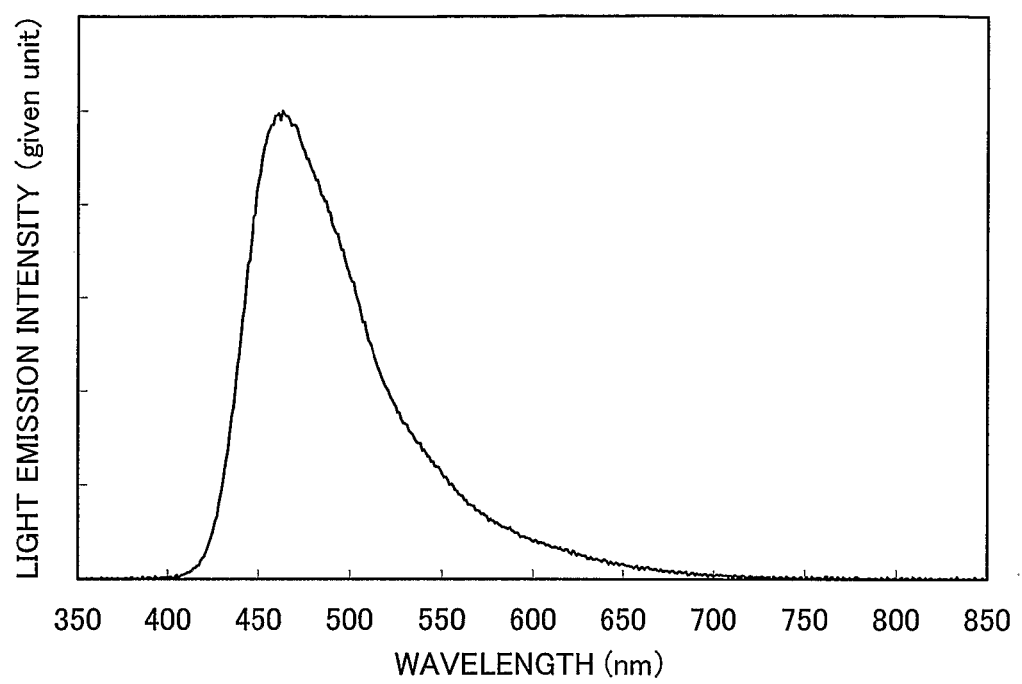
FIG. 27 is a graph showing light emission spectrum of a light-emitting element manufactured in Embodiment 5.

The light emission spectrum of the light-emitting element manufactured in this embodiment is shown in FIG. 27. In FIG. 27, a horizontal axis represents a wavelength (nm) and a vertical axis represents the intensity (given unit). According to FIG. 27, it is known that the light-emitting element of the present invention has a peak of light emission spectrum at 465 nm, and emits blue light. Moreover, the CIE chromaticity coordinates were x=0.18, y=0.22. Consequently, it was known that the light-emitting element of the present embodiment emits blue light with good color purity.

Embodiment 6

A method for manufacturing a light-emitting element that uses the YGABPA synthesized in Synthetic Example 1 as a light-emitting substance and an operational characteristic of the light-emitting element will be described in this embodiment. Further, a light-emitting element of the present embodiment is similar to the light-emitting element of Embodiment 2 in point of having a structure in which five layers respectively having different substances and thicknesses are stacked between a first electrode and a second electrode. Therefore, the present embodiment will be described with reference to FIG. 15 also used in the description of Embodiment 2.

As shown in FIG. 15, indium tin oxide containing silicon oxide was formed over a glass substrate 301 by a sputtering method to form a first electrode 302. The thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to $1\times10^{-4}$ Pa. Then, a first layer 303 including copper phthalocyanine was formed over the first electrode 302 by an evaporation method. The thickness of the first layer 303 was set to be 20 nm. The first layer 303 serves as a hole-injecting layer when operating the light-emitting element.

Subsequently, a second layer 304 including BSPB was formed over the first layer 303 by an evaporation method. The thickness of the second layer 304 was set to be 40 nm. The second layer 304 serves as a hole-transporting layer when operating the light-emitting element.

A third layer 305 including t-BuDNA and YGABPA was formed over the second layer 304 by a co-evaporation method. The thickness of the third layer 305 was set to be 40 nm. The t-BuDNA-YGABPA mass ratio was adjusted to be 1:0.1. Thus, the YGABPA was in such a state that the YGABPA is dispersed in a layer including the t-BuDNA. The third layer 305 serves as a light-emitting layer when operating the light-emitting element. Further, the YGABPA serves as a light-emitting substance.

Next, a fourth layer 306 including Alq$_3$ was formed over the third layer 305 by an evaporation method. The thickness of the fourth layer 306 was set to be 20 nm. The fourth layer 306 serves as an electron-transporting layer when operating the light-emitting element.

A fifth layer 307 including calcium fluoride was formed over the fourth layer 306 by an evaporation method. The thickness of the fifth layer 307 was set to be 1 nm. The fifth layer 307 serves as an electron-injecting layer when operating the light-emitting element.

Next, a second electrode 308 including aluminum was formed over the fifth layer 307. The thickness of the second electrode 308 was set to be 200 nm.

When voltage is applied to the light-emitting element manufactured as above such that an electric potential of the first electrode 302 is higher than that of the second electrode 308, current flows through the light-emitting element. Holes and electrons are recombined at the third layer 305 serving as a light-emitting layer to generate excited energy. The excited YGABPA emits light when returning to a ground state.

This light-emitting element was sealed in a glove box under a nitrogen atmosphere without exposing it to the atmospheric air. Thereafter, an operational characteristic of the light-emitting element was measured. The measurement was carried out at room temperature (under an atmosphere maintaining 25° C.).

Figure 28:
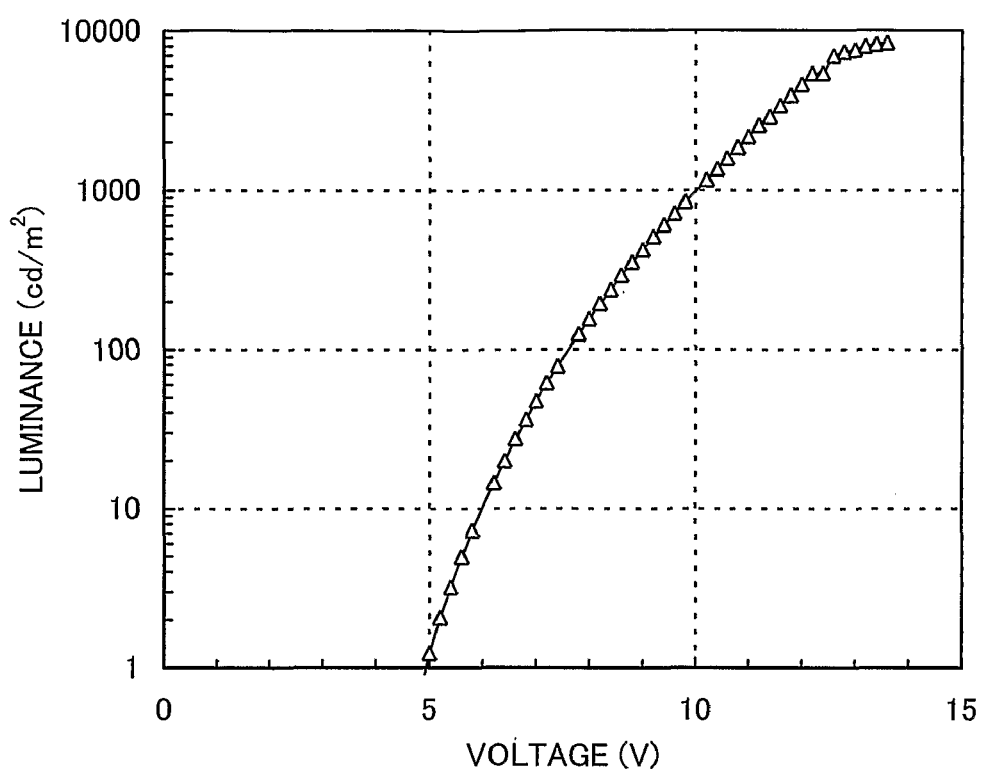
FIG. 28 is a graph showing a luminance-voltage characteristic of a light-emitting element manufactured in Embodiment 6.
Figure 29:
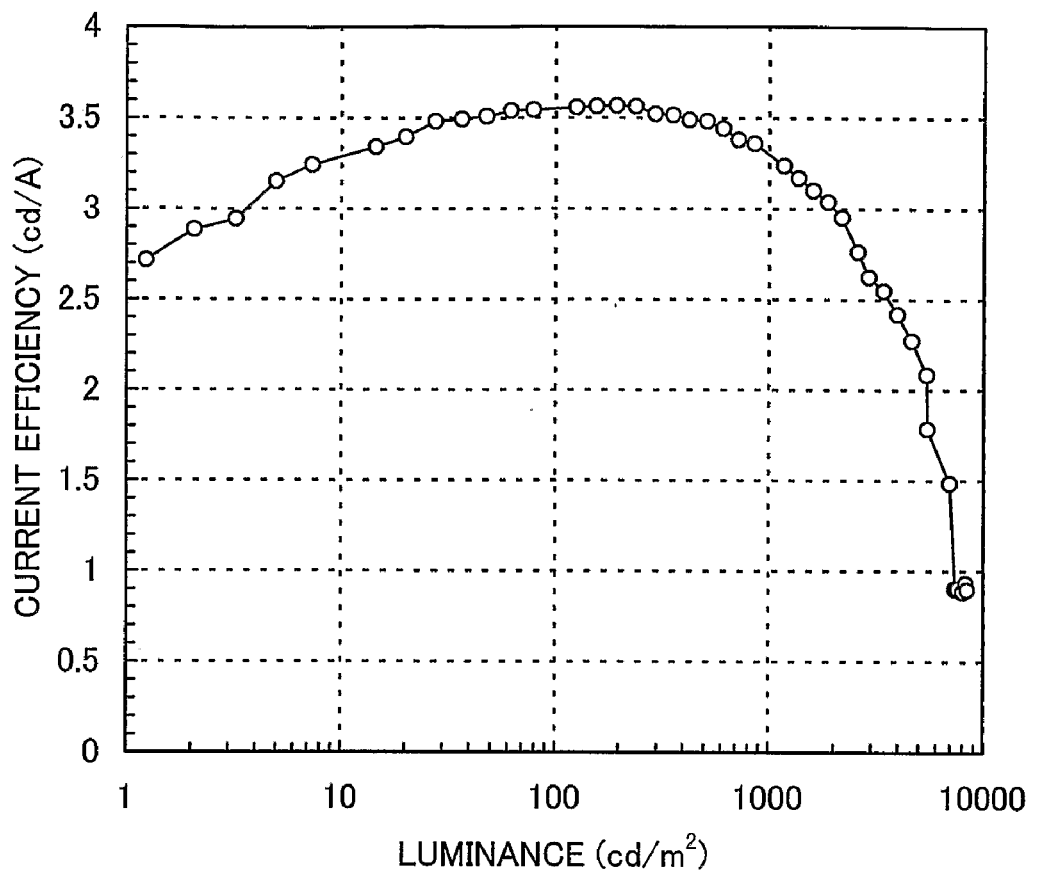
FIG. 29 is a graph showing a luminance-current efficiency characteristic of a light-emitting element manufactured in Embodiment 6.

Measurement results are shown in FIG. 28 and FIG. 29. FIG. 28 shows a measurement result of a voltage-luminance characteristic whereas FIG. 29 shows a measurement result of a luminance-current efficiency characteristic. In FIG. 28, a horizontal axis represents the voltage (V) and a vertical axis represents the luminance (cd/m$^2$). Moreover, in FIG. 29, a horizontal axis represents the luminance (cd/m$^2$) and a vertical axis represents the current efficiency (cd/A).

Figure 30:
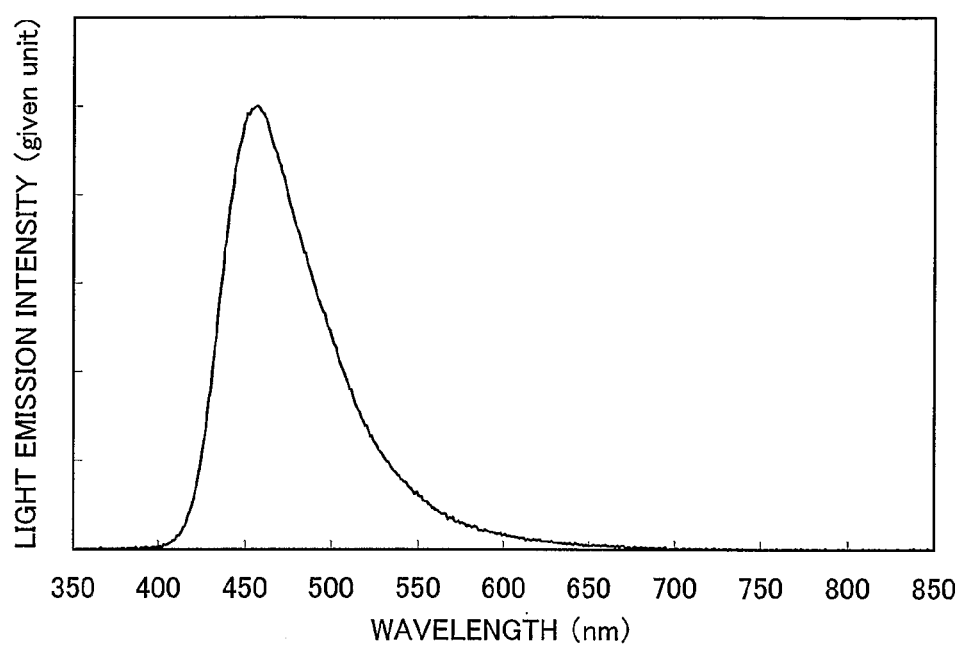
FIG. 30 is a graph showing light emission spectrum of a light-emitting element manufactured in Embodiment 6.

The light emission spectrum of the light-emitting element manufactured in this embodiment is shown in FIG. 30. In FIG. 30, a horizontal axis represents a wavelength (nm) and a vertical axis represents the intensity (given unit). According to FIG. 30, it is known that the light-emitting element of the present invention has a peak of light emission spectrum at 459 nm, and emits blue light. Moreover, the CIE chromaticity coordinates were x=0.15, y=0.15. Consequently, it was known that the light-emitting element of the present embodiment emits blue light with good color purity.

Embodiment 7

A method for manufacturing a light-emitting element that uses the YGABPA synthesized in Synthetic Example 1 as a light-emitting substance and an operational characteristic of the light-emitting element will be described in this embodiment. Further, a light-emitting element of the present embodiment is similar to the light-emitting element of Embodiment 2 in point of having a structure in which five layers respectively having different substances and thicknesses are stacked between a first electrode and a second electrode. Therefore, the present embodiment will be described with reference to FIG. 15 also used in the description of Embodiment 2.

As shown in FIG. 15, indium tin oxide containing silicon oxide was formed over a glass substrate 301 by a sputtering method to form a first electrode 302. The thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to 1×10$^{-4}$ Pa. Then, a first layer 303 including DNTPD was formed over the first electrode 302 by an evaporation method. The thickness of the first layer 303 was set to be 50 nm. The first layer 303 serves as a hole-injecting layer when operating the light-emitting element.

Subsequently, a second layer 304 including NPB was formed over the first layer 303 by an evaporation method. The thickness of the second layer 304 was set to be 10 nm. The second layer 304 serves as a hole-transporting layer when operating the light-emitting element.

A third layer 305 including CzPA and YGABPA was formed over the second layer 304 by a co-evaporation method. The thickness of the third layer 305 was set to be 40 nm. The CzPA-YGABPA mass ratio was adjusted to be 1:0.1. Thus, the YGABPA was in such a state that the YGABPA is dispersed in a layer including the CzPA. The third layer 305 serves as a light-emitting layer when operating the light-emitting element. The YGABPA serves as a light-emitting substance. The CzPA is a substance represented by the following structural formula (29).

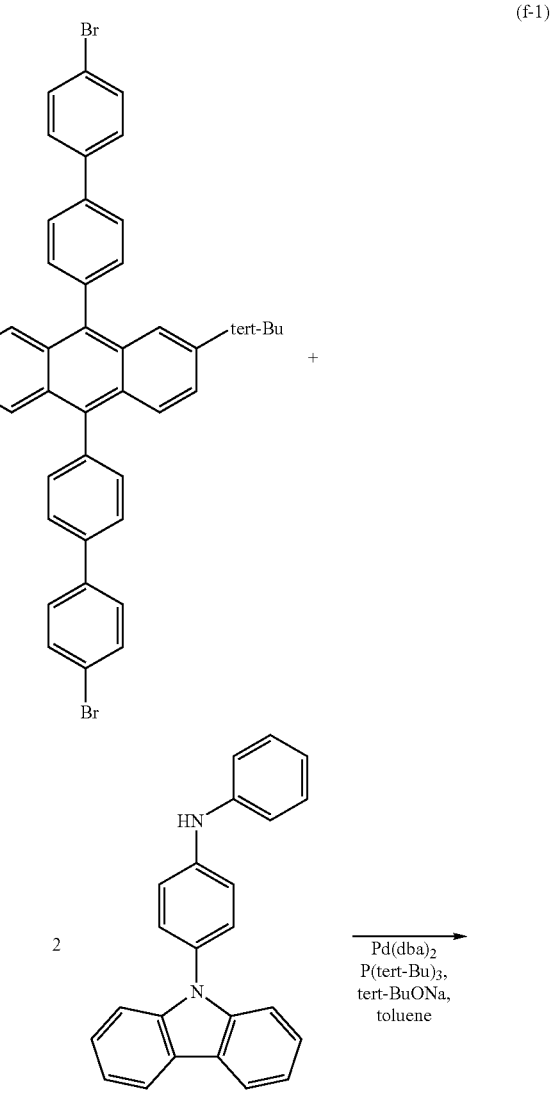

-continued

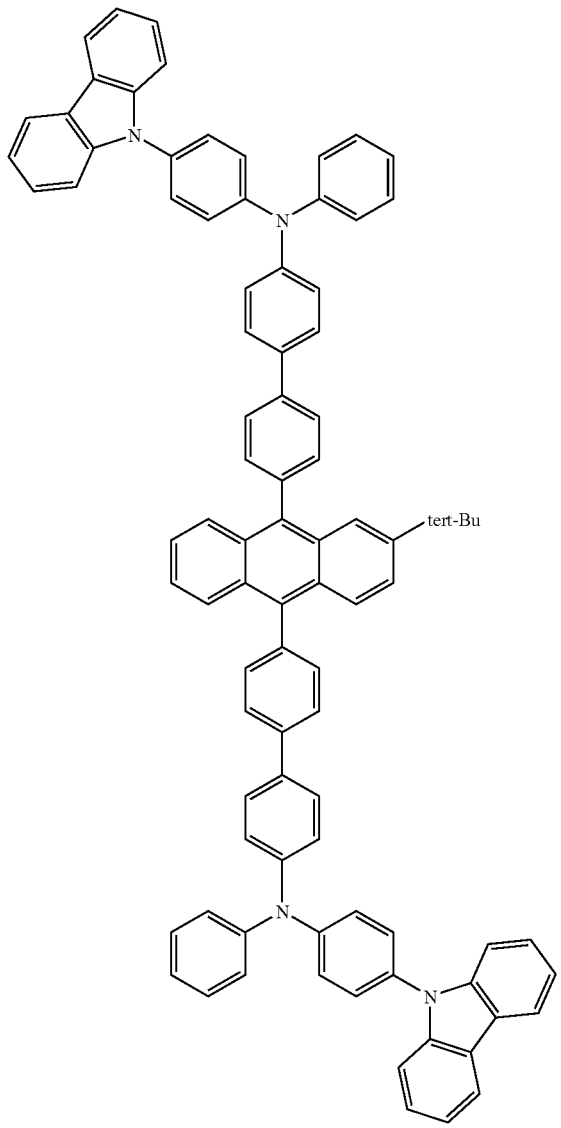

Next, a fourth layer 306 including Alq₃ was formed over the third layer 305 by an evaporation method. The thickness of the fourth layer 306 was set to be 20 nm. The fourth layer 306 serves as an electron-transporting layer when operating the light-emitting element.

A fifth layer 307 including calcium fluoride was formed over the fourth layer 306 by an evaporation method. The thickness of the fifth layer 307 was set to be 1 nm. The fifth layer 307 serves as an electron-injecting layer when operating the light-emitting element.

Next, a second electrode 308 including aluminum was formed over the fifth layer 307. The thickness of the second electrode 308 was set to be 200 nm.

When voltage is applied to the light-emitting element manufactured as above such that an electric potential of the first electrode 302 is higher than that of the second electrode 308, current flows through the light-emitting element. Holes and electrons are recombined at the third layer 305 serving as a light-emitting layer to generate excited energy. The excited YGABPA emits light when returning to a ground state.

This light-emitting element was sealed in a glove box under a nitrogen atmosphere without exposing it to the atmospheric air. Thereafter, an operational characteristic of the light-emitting element was measured. Further, the measurement was carried out at room temperature (under an atmosphere maintaining 25° C.).

Figure 31:
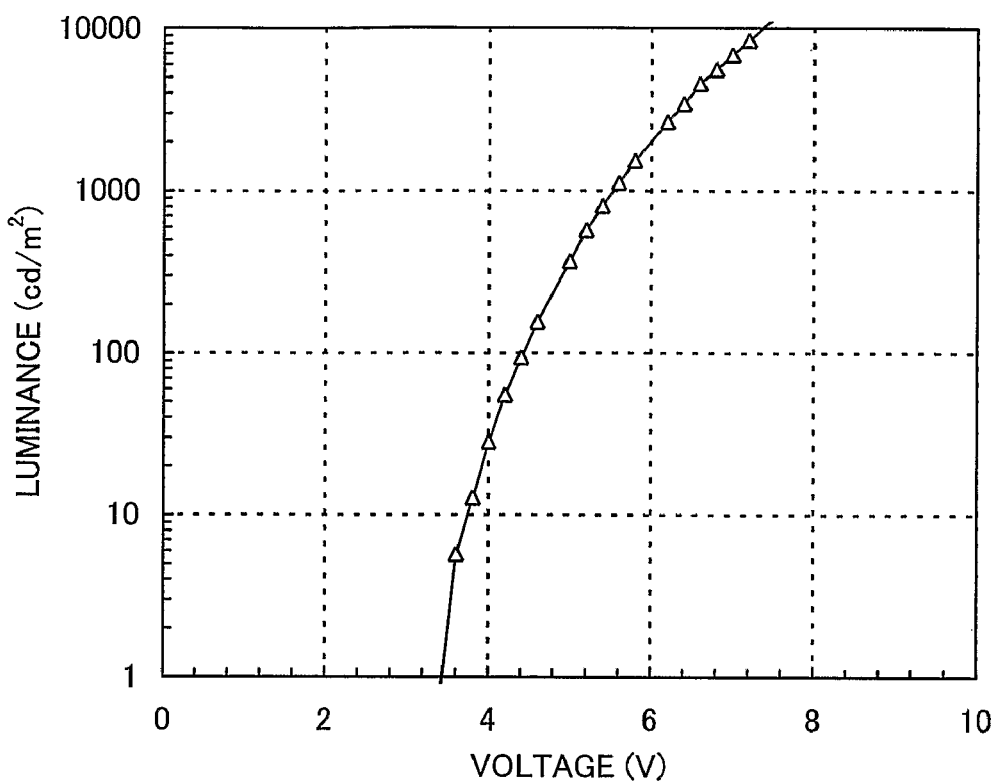
FIG. 31 is a graph showing a luminance-voltage characteristic of a light-emitting element manufactured in Embodiment 7.
Figure 32:
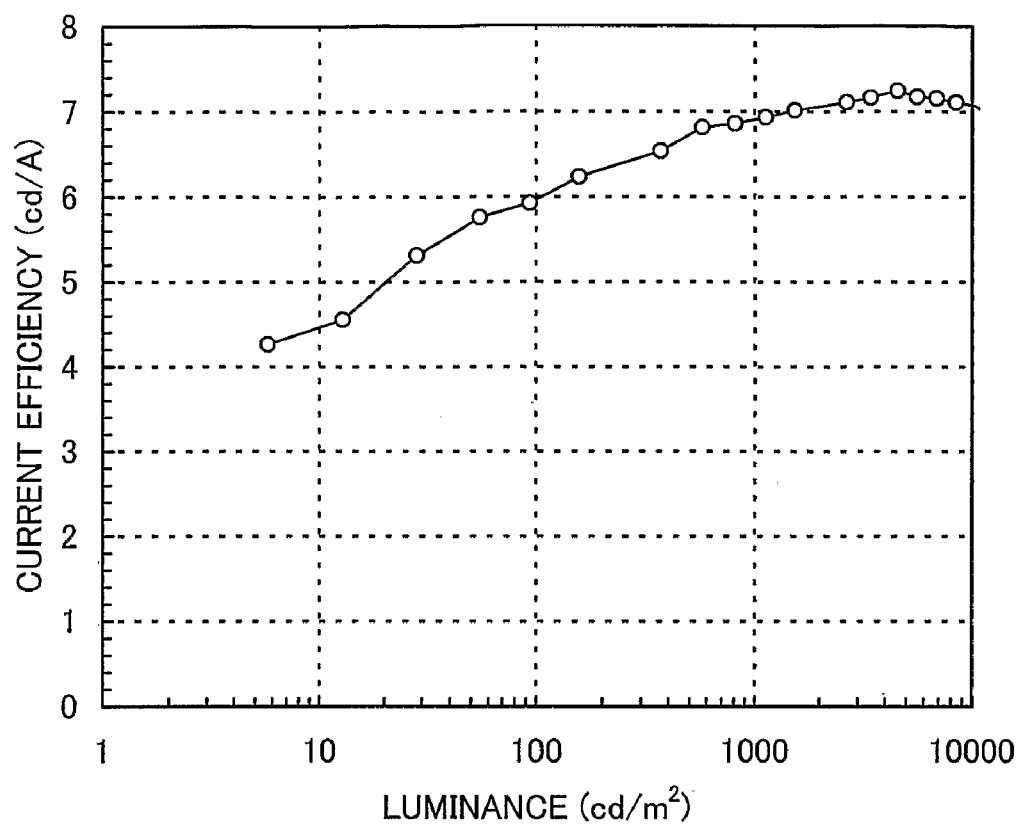
FIG. 32 is a graph showing a luminance-current efficiency characteristic of a light-emitting element manufactured in Embodiment 7.

Measurement results are shown in FIG. 31 and FIG. 32. FIG. 31 shows a measurement result of a voltage-luminance characteristic whereas FIG. 32 shows a measurement result of a luminance-current efficiency characteristic. In FIG. 31, a horizontal axis represents the voltage (V) and a vertical axis represents the luminance (cd/m²). Moreover, in FIG. 32, a horizontal axis represents the luminance (cd/m²) and a vertical axis represents the current efficiency (cd/A).

Figure 33:
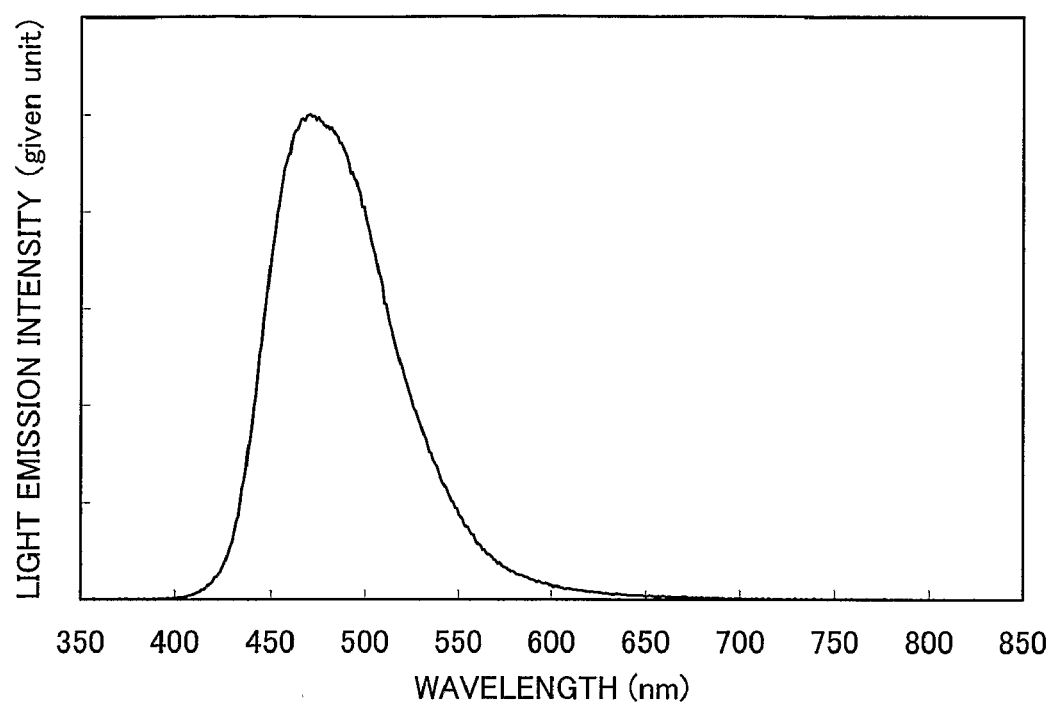
FIG. 33 is a graph showing light emission spectrum of a light-emitting element manufactured in Embodiment 7.

The light emission spectrum of the light-emitting element manufactured in this embodiment is shown in FIG. 33. In FIG. 33, a horizontal axis represents a wavelength (nm) and a vertical axis represents the intensity (given unit). According to FIG. 33, it is known that the light-emitting element of the present invention has a peak of light emission spectrum at 474 nm, and emits blue light. Moreover, the CIE chromaticity coordinates were x=0.15, y=0.24. Consequently, it is known that the light-emitting element of the present embodiment emits blue light with good color purity.

Embodiment 8

A method for manufacturing a light-emitting element that uses the YGABPA synthesized in Synthetic Example 1 as a light-emitting substance and an operational characteristic of the light-emitting element will be described in this embodiment. Further, a light-emitting element of the present embodiment is similar to the light-emitting element of Embodiment 2 in point of having a structure in which five layers respectively having different substances and thicknesses are stacked between a first electrode and a second electrode. Therefore, the present embodiment will be described with reference to FIG. 15 also used in the description of Embodiment 2.

As shown in FIG. 15, indium tin oxide containing silicon oxide was formed over a glass substrate 301 by a sputtering method to form a first electrode 302. The thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus.

The inside of the vacuum evaporation apparatus was evacuated so that the pressure was reduced to 1×10⁻⁴ Pa. Then, a first layer 303 including NPB and molybdenum oxide was formed over the first electrode 302 by a co-evaporation method. The thickness of the first layer 303 was set to be 50 nm. The NPB-molybdenum oxide mass ratio is set to be 4:2. It is to be noted that molybdenum trioxide was particularly used as the evaporation material. The first layer 303 serves as a hole-generating layer when operating the light-emitting element.

Subsequently, a second layer 304 including NPB was formed over the first layer 303 by an evaporation method. The thickness of the second layer 304 was set to be 10 nm. The second layer 304 serves as a hole-transporting layer when operating the light-emitting element.

A third layer 305 including CzPA and YGABPA was formed over the second layer 304 by a co-evaporation method. The thickness of the third layer 305 was set to be 40 nm. The CzPA-YGABPA mass ratio was adjusted to be 1:0.1. Thus, the YGABPA was in such a state that the YGABPA is dispersed in a layer including the t-BuDNA. The third layer 305 serves as a light-emitting layer when operating the light-emitting element. Further, the YGABPA serves as a light-emitting substance.

Next, a fourth layer 306 including Alq$_3$ was formed over the third layer 305 by an evaporation method. The thickness of the fourth layer 306 was set to be 20 nm. The fourth layer 306 serves as an electron-transporting layer when operating the light-emitting element.

A fifth layer 307 including calcium fluoride was formed over the fourth layer 306 by an evaporation method. The thickness of the fifth layer 307 was set to be 1 nm. The fifth layer 307 serves as an electron-injecting layer when operating the light-emitting element.

Next, a second electrode 308 including aluminum was formed over the fifth layer 307. The thickness of the second electrode 308 was set to be 200 nm.

When voltage is applied to the light-emitting element manufactured as above such that an electric potential of the first electrode 302 is higher than that of the second electrode 308, current flows through the light-emitting element. Holes and electrons are recombined at the third layer 305 serving as a light-emitting layer to generate excited energy. The excited YGABPA emits light when returning to a ground state.

This light-emitting element was sealed in a glove box under a nitrogen atmosphere without exposing it to the atmospheric air. Thereafter, an operational characteristic of the light-emitting element was measured. The measurement was carried out at room temperature (under an atmosphere maintaining 25° C.).

Figure 34:
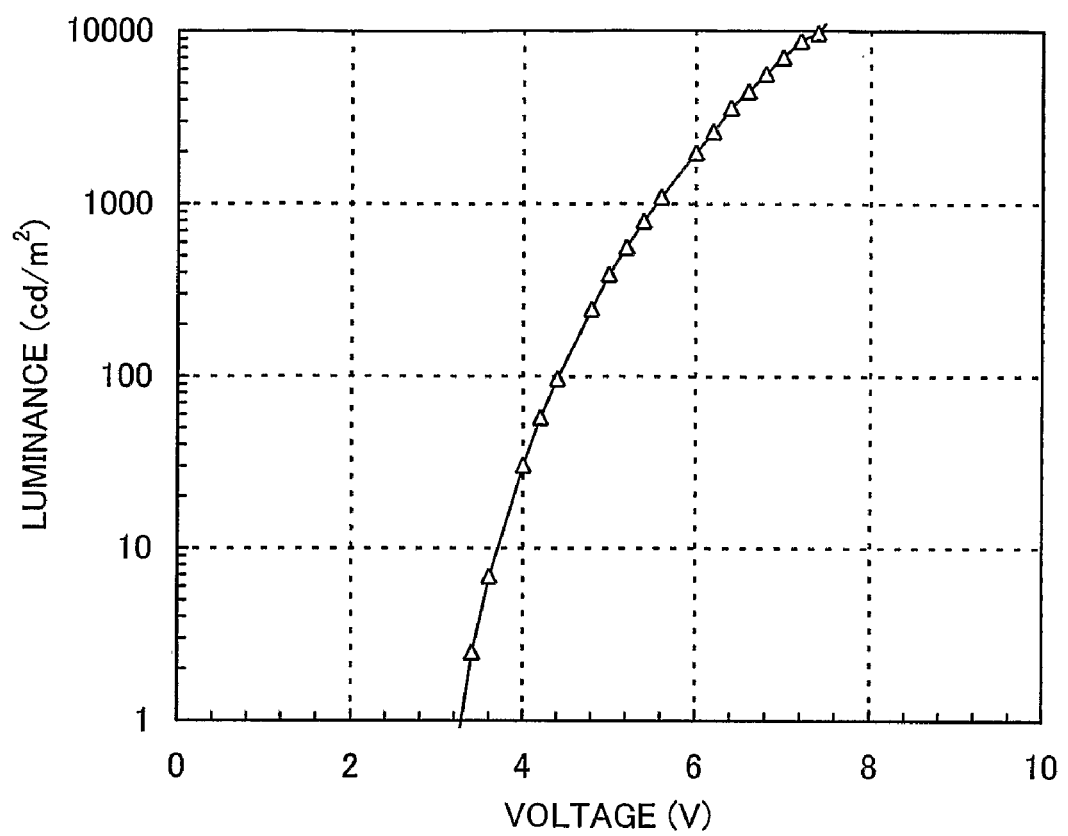
FIG. 34 is a graph showing a luminance-voltage characteristic of a light-emitting element manufactured in Embodiment 8.
Figure 35:
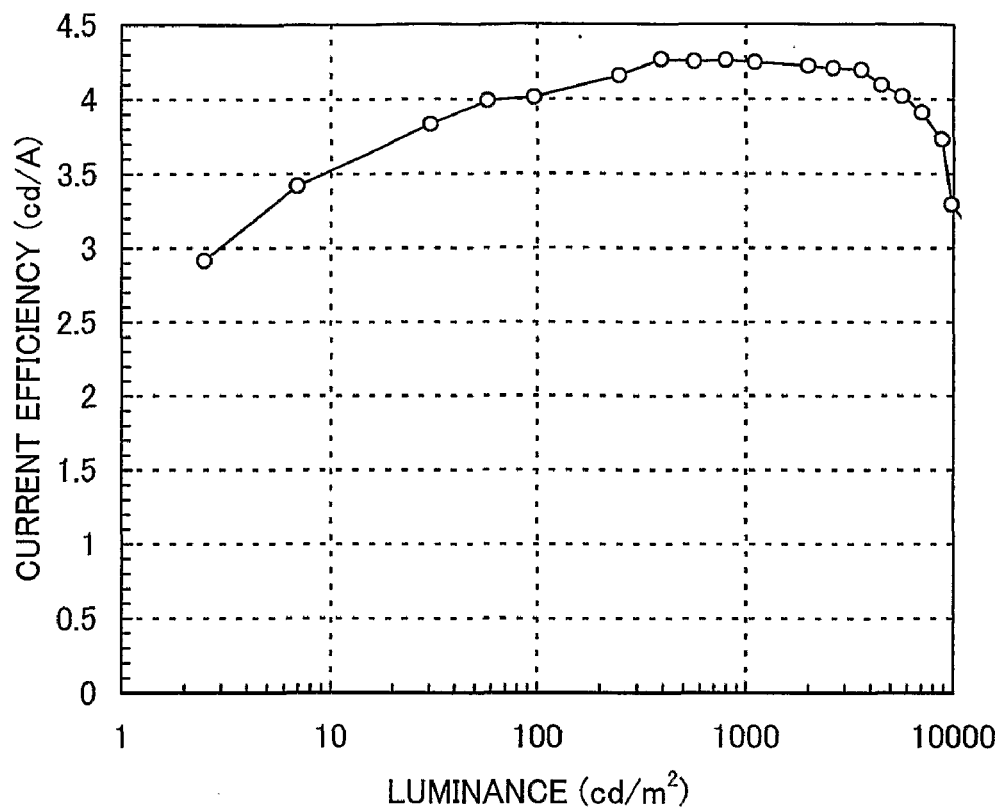
FIG. 35 is a graph showing a luminance-current efficiency characteristic of a light-emitting element manufactured in Embodiment 8.

Measurement results are shown in FIG. 34 and FIG. 35. FIG. 34 shows a measurement result of a voltage-luminance characteristic whereas FIG. 34 shows a measurement result of a luminance-current efficiency characteristic. In FIG. 34, a horizontal axis represents the voltage (V) and a vertical axis represents the luminance (cd/m$^2$). Also, in FIG. 35, a horizontal axis represents the luminance (cd/m$^2$) and a vertical axis represents the current efficiency (cd/A).

Figure 36:
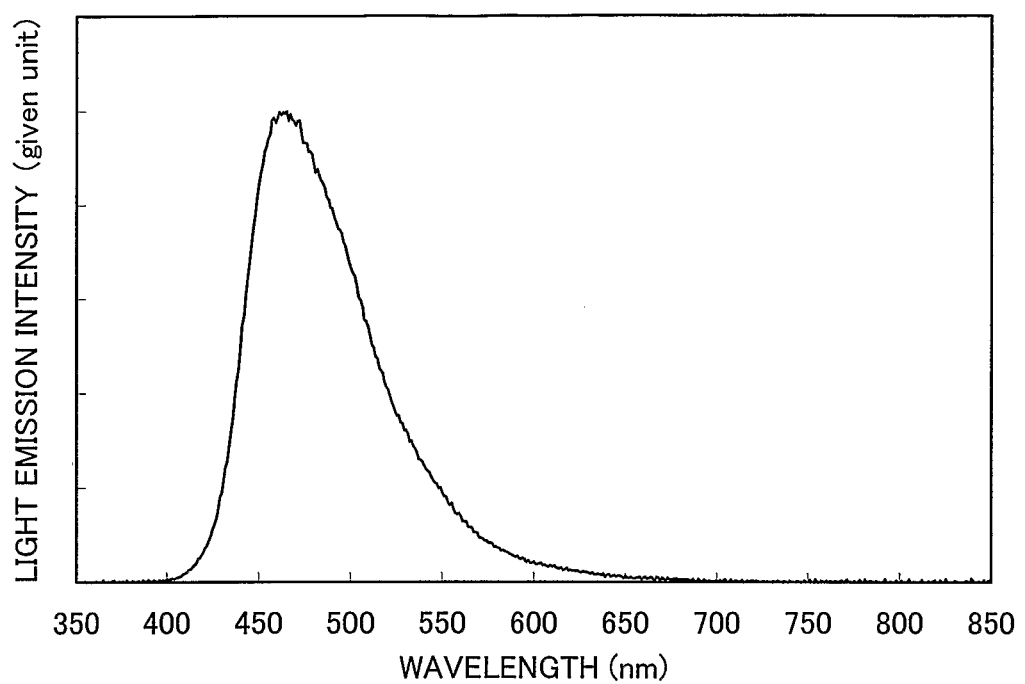
FIG. 36 is a graph showing light emission spectrum of a light-emitting element manufactured in Embodiment 8.

The light emission spectrum of the light-emitting element manufactured in this embodiment is shown in FIG. 36. In FIG. 36, a horizontal axis represents a wavelength (nm) and a vertical axis represents the intensity (given unit). According to FIG. 36, it is known that the light-emitting element of the present invention has a peak of light emission spectrum at 466 nm, and emits blue light. Moreover, the CIE chromaticity coordinates were x=0.16, y=0.21. Consequently, it is known that the light-emitting element of the present embodiment emits blue light with good color purity.

Figure 38:
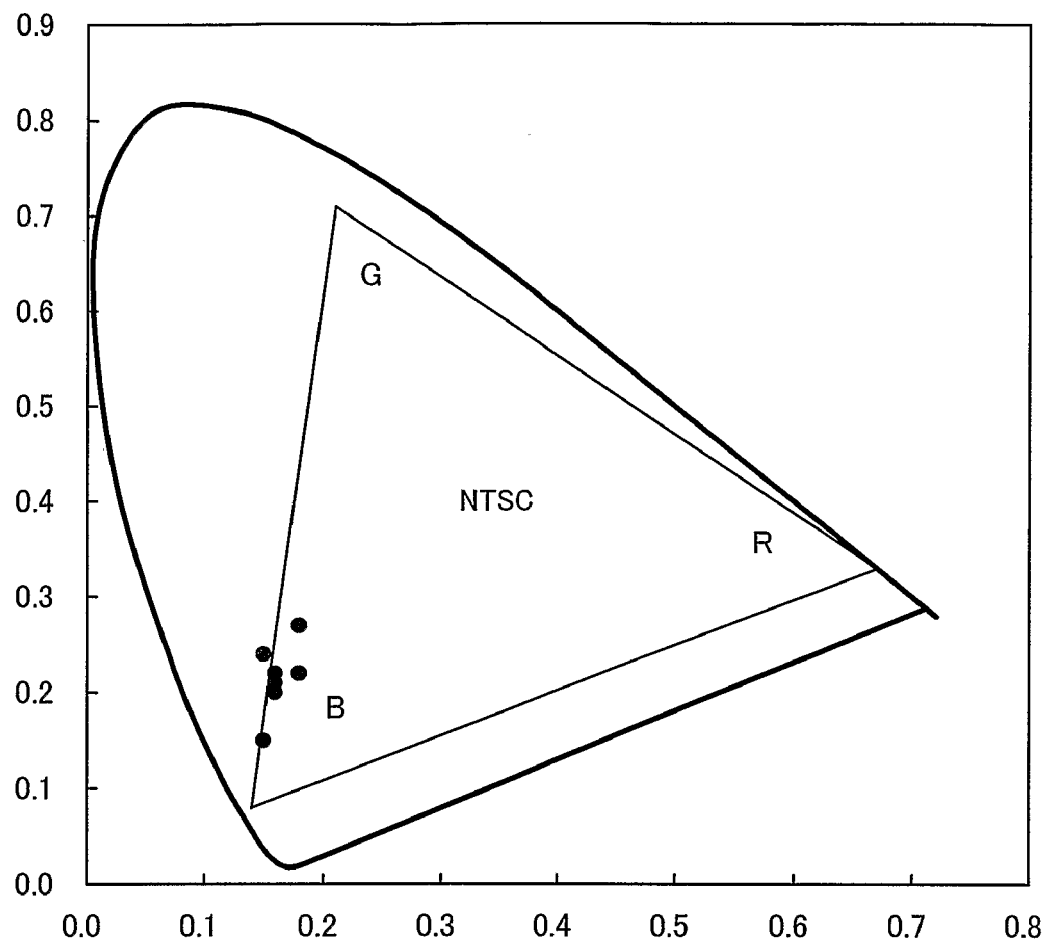
FIG. 38 is a chromaticity diagram in which chromaticity of each of the light-emitting elements manufactured in Embodiments 2 to 8 is plotted.

FIG. 38 shows a chromaticity diagram in the CIE chromaticity in which the chromaticity of each of the light-emitting elements manufactured in Embodiments 2 to 8 is plotted. Moreover, FIG. 38 shows a color reproduction area in accordance with an NTSC method in a triangle frame. It is understood from FIG. 38 that each of the light-emitting elements manufactured in Embodiments 2 to 8 emits fine blue light and is effective as a blue pixel in a light-emitting device for displaying an image by an NTSC method.

The invention claimed is:

1. An anthracene derivative represented by a general formula (1):

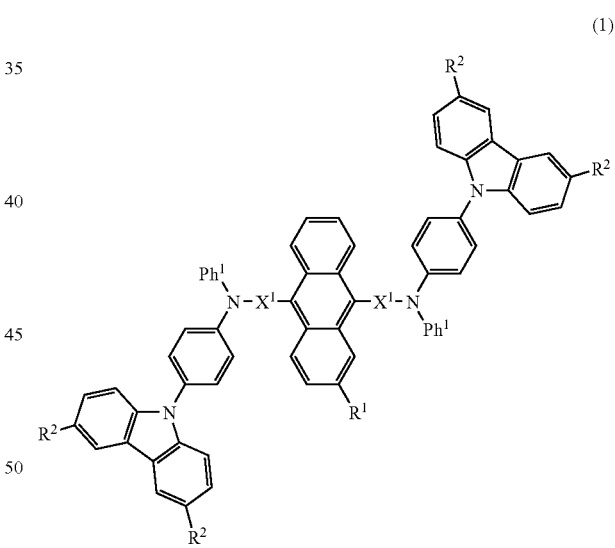

(1)

wherein R$^1$ represents hydrogen or an alkyl group having 1 to 4 carbon atoms, wherein R$^2$ represents any one of hydrogen, an alkyl group having 1 to 4 carbon atoms, and an aryl group having 6 to 12 carbon atoms, wherein Ph$^1$ represents a phenyl group, and wherein X$^1$ represents an arylene group having 6 to 15 carbon atoms.

2. An anthracene derivative represented by a general formula (2):

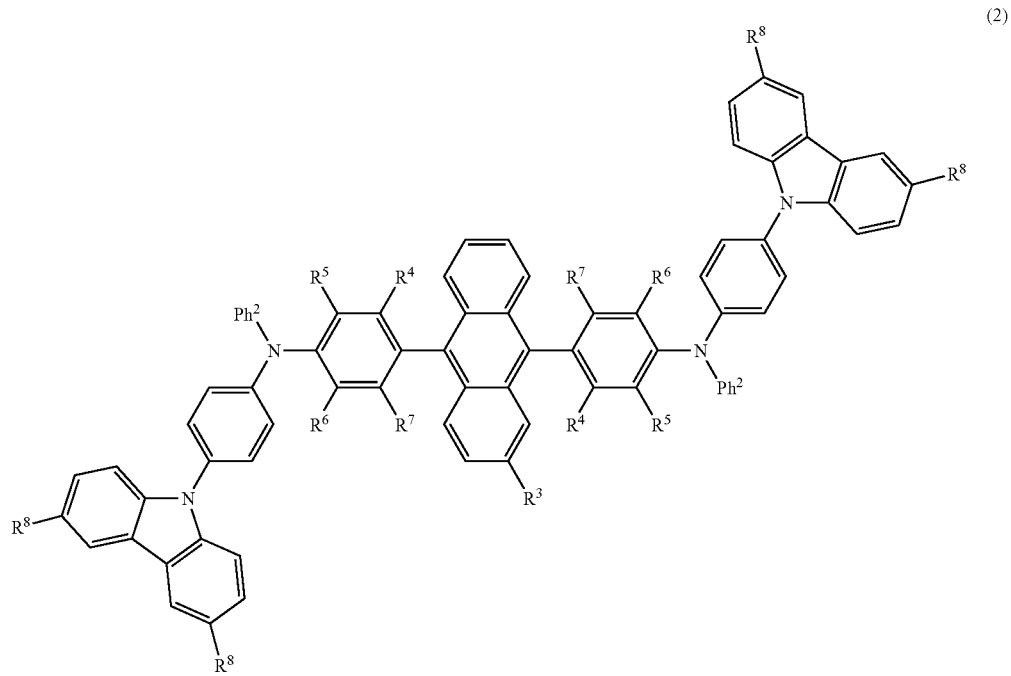

(2)

wherein $R^3$ represents hydrogen or an alkyl group having 1 to 4 carbon atoms, wherein $R^4$ to $R^7$ represent hydrogen, or $R^4$ and $R^5$ represent aromatic rings which are bonded to each other and $R^6$ and $R^7$ represent aromatic rings which are bonded to each other, $R^8$ represents any one of hydrogen, an alkyl group having 1 to 4 carbon atoms, and an aryl group having 6 to 12 carbon atoms, and $Ph^2$ represents a phenyl group.

3. An anthracene derivative represented by a general formula (3):

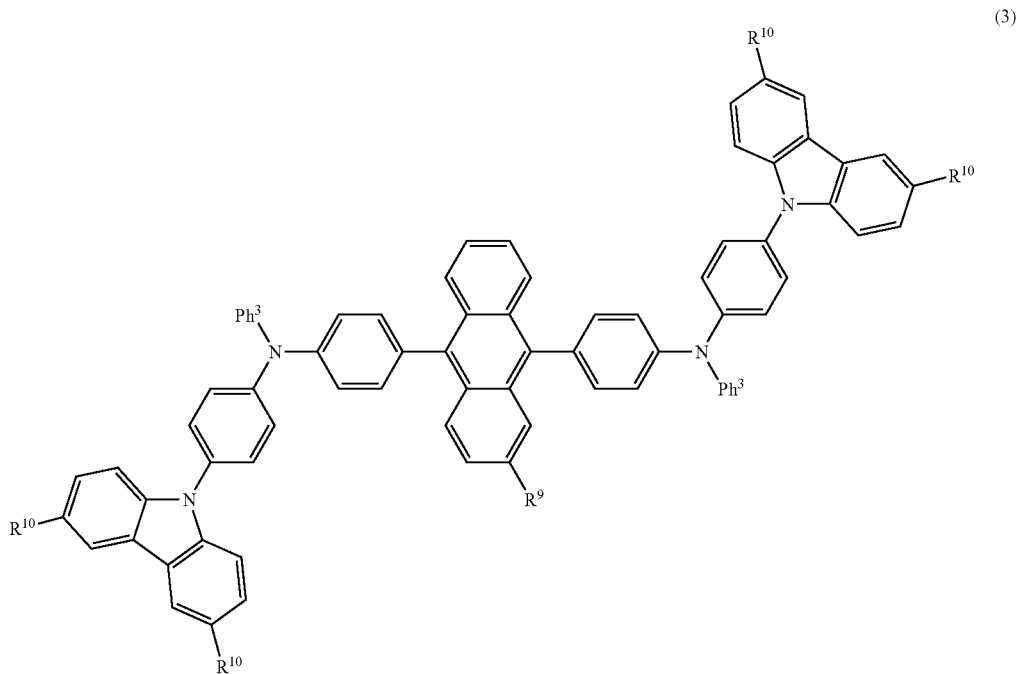

(3)

wherein, $R^9$ represents hydrogen or an alkyl group having 1 to 4 carbon atoms, wherein $R^{10}$ represents any one of hydrogen, an alkyl group having 1 to 4 carbon atoms, and an aryl group having 6 to 12 carbon atoms, and wherein $Ph^3$ represents a phenyl group.

4. An anthracene derivative represented by a general formula (4):

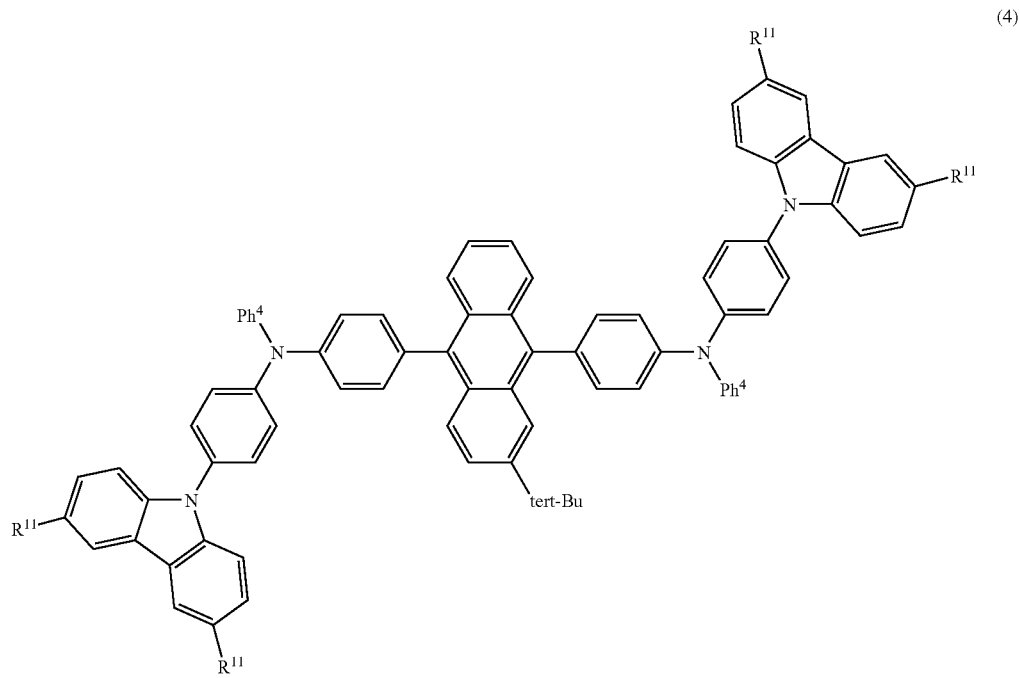

(4)

wherein $R^{11}$ represents any one of hydrogen, an alkyl group having 1 to 4 carbon atoms, and an aryl group having 6 to 12 carbon atoms, and wherein $Ph^4$ represents a phenyl group.

5. An anthracene derivative represented by a general formula (5):

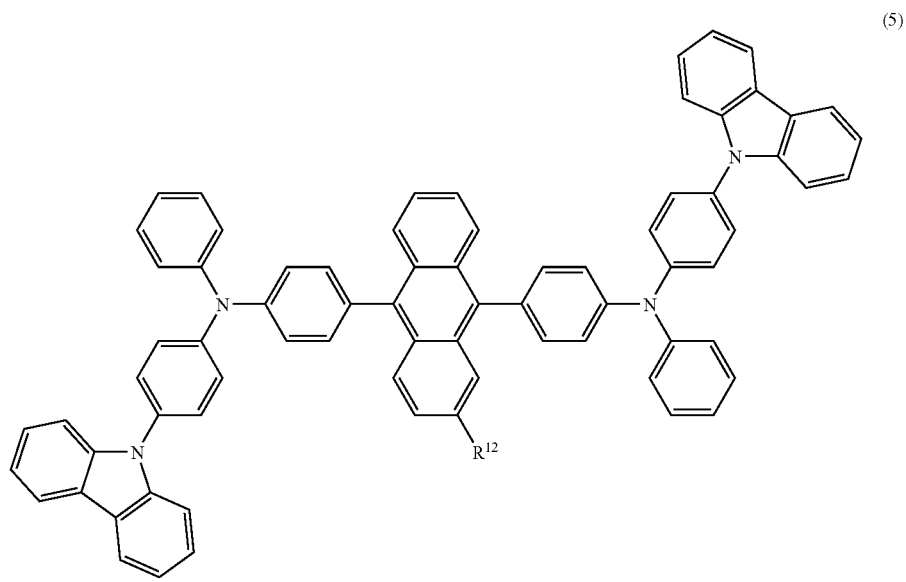

(5)

wherein R$^{12}$ represents hydrogen or an alkyl group having 1 to 4 carbon atoms.
6. An anthracene derivative represented by a general formula (6):
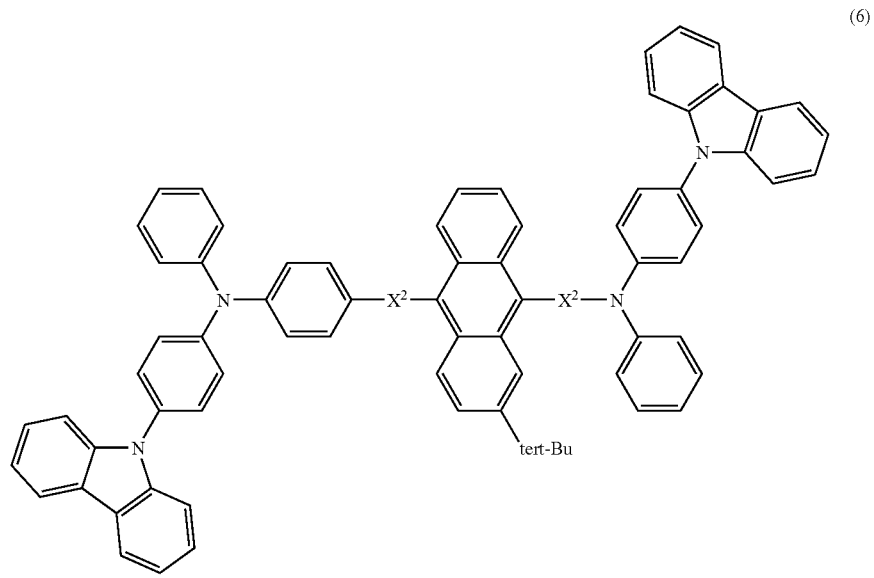
(6)
wherein X$^2$ represents an arylene group having 6 to 15 carbon atoms.
7. An anthracene derivative represented by a general formula (7):
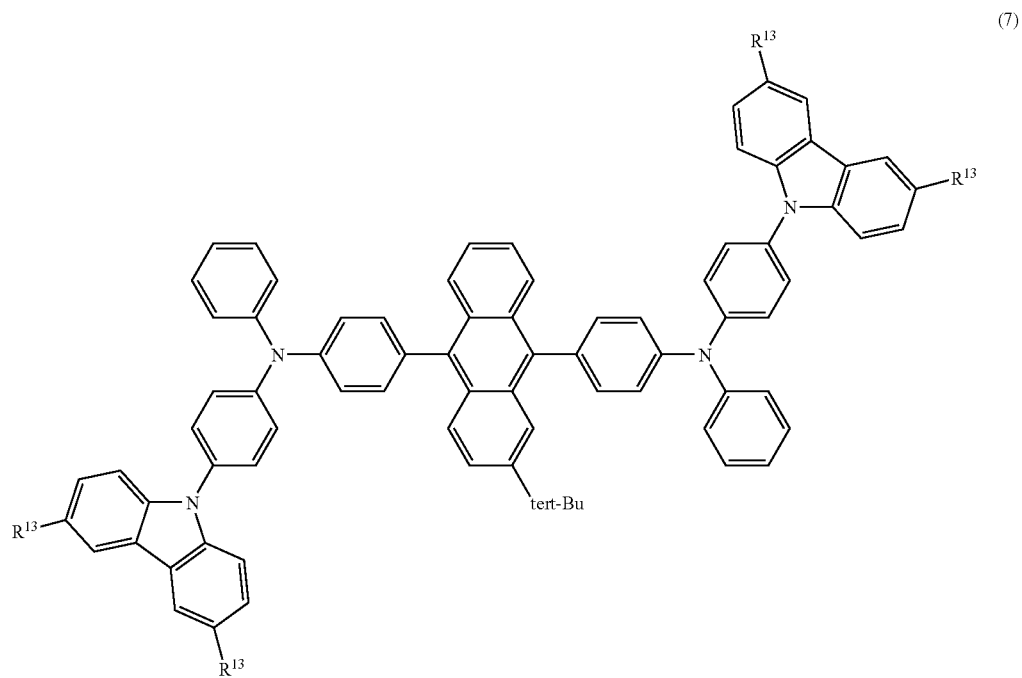
(7)

wherein $R^{13}$ represents any one of hydrogen, an alkyl group having 1 to 4 carbon atoms, and an aryl group having 6 to 12 carbon atoms.

8. A light-emitting element comprising a layer including the anthracene derivative according to any one of claims 1 to 7 between electrodes.

9. A light-emitting element comprising the anthracene derivative according to any one of claims 1 to 7 as a light-emitting substance.

10. A light-emitting element comprising the anthracene derivative according to any one of claims 1 to 7 as a host.

11. A light-emitting device comprising the light-emitting element according to claim 9 or 10 in a pixel portion.

12. An electronic appliance using the light-emitting device according to claim 11 in a display portion.

* * * * *